United States Patent

Yamada et al.

Patent Number: 5,667,936
Date of Patent: Sep. 16, 1997

[54] SILVER HALIDE PHOTOGRAPHIC MATERIAL

[75] Inventors: Kohzaburoh Yamada; Hiroshi Takeuchi; Takashi Hoshimiya; Toshiaki Kubo; Shigeo Hirano, all of Kanagawa, Japan

[73] Assignee: Fuji Photo Film Co., Ltd., Kanagawa, Japan

[21] Appl. No.: 627,998

[22] Filed: Apr. 4, 1996

[30] Foreign Application Priority Data

| Apr. 6, 1995 | [JP] | Japan | 7-104624 |
| Apr. 6, 1995 | [JP] | Japan | 7-104626 |
| Apr. 6, 1995 | [JP] | Japan | 7-104648 |

[51] Int. Cl.$^6$ ............ G03C 1/295
[52] U.S. Cl. ............ 430/264; 430/598
[58] Field of Search ............ 430/264, 598

[56] References Cited

U.S. PATENT DOCUMENTS

| 5,155,007 | 10/1992 | Hara et al. | 430/264 |
| 5,252,426 | 10/1993 | Chan | 430/264 |
| 5,284,732 | 2/1994 | Nii et al. | 430/264 |
| 5,382,496 | 1/1995 | Sakai et al. | 430/264 |
| 5,478,697 | 12/1995 | Sakai et al. | 430/264 |
| 5,496,681 | 3/1996 | Ezoe et al. | 430/264 |

FOREIGN PATENT DOCUMENTS

| 0670516 | 9/1995 | European Pat. Off. |
| 3125134 | 5/1991 | Japan. |
| 682944 | 3/1994 | Japan. |
| 9303414 | 2/1993 | WIPO. |

*Primary Examiner*—Richard L. Schilling
*Attorney, Agent, or Firm*—Sughrue, Mion, Zinn, Macpeak & Seas

[57] ABSTRACT

A silver halide photographic material comprising at least one of hydrazide compounds represented by formula (1), (2) or (3):

$$X_1-(R_3)_{m3}-(L_2-R_2)_{m2}-L_1-A_1-NHNH-CO-R_1 \quad (1)$$

$$X_{21}-(R_{23})_{m23}-(L_{22}-R_{22})_{m22}-L_{21}-Ar-NHNH-CO-R_{21} \quad (2)$$

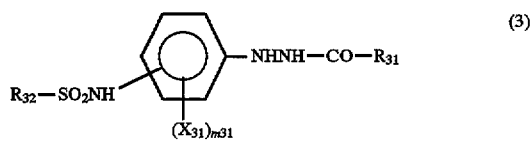

The substituents in formulae (1), (2) and (3) are defined in the specification.

4 Claims, No Drawings

SILVER HALIDE PHOTOGRAPHIC MATERIAL

FIELD OF THE INVENTION

This invention relates to a negative or direct positive silver halide photographic material containing a hydrazine compound of specific structure.

BACKGROUND OF THE INVENTION

In the field of graphic arts, an image formation system providing ultrahigh contrast (especially γ (gamma) exceeding 10) is required for achieving satisfactory reproduction of a continuous tone with a dot image or reproduction of a line image. An image formation system for obtaining ultra-high contrast photographic properties using a stable developing solution has been demanded. To meet this demand, an image formation system for obtaining a hard negative having a γ exceeding 10 has been proposed, in which a surface latent image type silver halide photographic material containing a specific acylhydrazine compound is developed with a developer adjusted to pH 11.0 to 12.3 and containing 0.15 mol/l or more of a sulfite preservative, as disclosed in U.S. Pat. Nos. 4,166,742, 4,168,977, 4,221,857, 4,224,401, 4,243, 739, 4,272,606, and 4,311,781. While conventional ultra-high contrast image formation systems were applicable only to a silver chlorobromide emulsion having a high silver chloride content, the new system has an advantage of applicability to a silver iodobromide emulsion and a silver chloroiodobromide emulsion. Furthermore, the developer used in this system permits addition of a high concentration of a sulfite preservative and therefore has improved preservation stability over lith developers which are allowed to contain only a little amount of a sulfite preservative. However, a developer at pH 11 or higher as used in the above system is instable due to the susceptibility to air oxidation and cannot withstand long-term preservation or use. Attempts have been made to obtain a high contrast image by developing a silver halide light-sensitive material containing a hydrazine compound with a developer having a lower Ph. For example, JP-A-1-179939 and JP-A-1-179940 (the term "JP-A" as used herein means an "unexamined published Japanese patent application") disclose development processing of a light-sensitive material containing a nucleation development accelerator having a group which can be adsorbed on silver halide grains and a nucleating agent containing a similar group by using a developer having a pH of pH 11.0 or lower. However, the emulsion used is a silver bromide emulsion or a silver iodobromide emulsion, and the system is not sufficient in providing stable photographic properties against variation of development progress or variation of the composition of a processing solution.

U.S. Pat. Nos. 4,998,604, 4,994,365, and 4,975,354 disclose hydrazine compounds having an ethylene oxide repeating unit and hydrazine compounds having a pyridinium group. Judging from the description of Examples, these inventions do not provide sufficiently high contrast, and it is difficult to secure high contrast and a necessary maximum density under practical development processing conditions. Furthermore, light-sensitive materials having hard gradation enhanced through nucleation by a hydrazine derivative show large variation in photographic properties with pH change of a developer; the pH of a developer largely varies, for example, it rises due to air oxidation and thickening through evaporation of water and falls due to absorption of carbon dioxide in air. Therefore, various attempts to reduce the dependence of photographic properties on pH of a developer have been made.

On the other hand, light-sensitive materials for dot-to-dot work which are generally handled in a lighted room occupy a large proportion in the field of photomechanical processing. In this field, high reproducibility in formation of superimposed letters even with a fine line width is demanded. To meet the demand, development of a nucleating agent having improved activity has been long awaited. The expectation for a nucleating agent with higher activity is particularly high for use in light-sensitive materials having such low sensitivity as to be handled in a lighted room because hard gradation enhancement by a nucleating agent hardly occurs in these materials.

In order to achieve these objects, highly active hydrazine nucleating agents have been developed as disclosed in JP-A-6-148828, JP-A-6-180477, and JP-A-6-194774.

In particular, nucleating agents having, as acyl group, an alkyl group substituted with at least one electron attracting group are excellent in that a very high contrast can be secured even with a developer at pH 11 or lower and that the variation of photographic properties due to exhaustion of a developer can be suppressed. Nevertheless, some of them are susceptible to oxidation and require further improvement in preservability.

Methods for obtaining a direct positive image which comprise surface developing an internal latent image type silver halide photographic emulsion in the presence of a nucleating agent and photographic emulsions or light-sensitive materials used therefor are known, e.g., from U.S. Pat. Nos. 2,456,953, 2,497,875, 2,497,876, 2,588,982, 2,592,250, 2,675,318, 3,227,552, and 3,317,322, British Patents 1,011,062, 1,151,363, 1,269,640, and 2,011,391, JP-B-43-29405 (the term "JP-B" as used herein means an "examined published Japanese patent application"), JP-B-49-38164, JP-A-53-16623, JP-A-53-137133, JP-A-54-37732, JP-A-54-40629, JP-A-54-74536, JP-A-54-74729, JP-A-55-52055, and JP-A-55-90940.

In the above-described methods for obtaining a direct positive image, the nucleating agent may be added to a developer but, it is more common to add it to a photographic emulsion layer or any other appropriate layers of a light-sensitive material.

Hydrazine compounds are the most well known of the nucleating agents that can be added to a direct positive silver halide light-sensitive material. Examples of the hydrazine compounds are described in *Research Disclosure*, No. 23510 (November, 1953), ibid, Vol. 151, No. 15162 (November, 1976), and ibid, Vol. 176, No. 17626 (December, 1978). In general, although hydrazine nucleating agents are the most excellent in discrimination, providing a large difference between a maximum density (Dmax) and a minimum density (Dmin), they are disadvantageous in that a high pH (pH 11 or higher) is required in processing, and improvement in this respect has been desired.

U.S. Pat. No. 5,252,426 discloses an arylhydrazide compound having a difluoroacetyl group or a monofluoroacetyl group as an acyl group. The U.S. patent also has a mention of compounds having directly bonded to the aryl group thereof a group which can be adsorbed to silver halide. However, any of the compounds disclosed does not exhibit sufficient performance for hard gradation enhancement by nucleation.

JP-A-3-125134 discloses a hydrazide compound having a difluoroacetyl group, but the compound disclosed turned out to fail to exhibit sufficient nucleating activity.

Highly active hydrazine nucleating agents disclosed in JP-A-63-234244, JP-A-63-234245, and the above-cited JP-A-6-148828, JP-A-6-180477, and JP-A-6-194774 are known as nucleating agents having a group accelerating adsorption to silver halide. However, many of them tend to be oxidized and require improvement in preservability. Thus, further enhancement of nucleating activity has been awaited for not only improved preservability but improved dot quality.

SUMMARY OF THE INVENTION

An object of the present invention is to provide a silver halide photographic material which can be processed with a stable developer to provide very high contrast photographic properties having a γ exceeding 10.

Another object of the present invention is to provide a silver halide photographic material for photomechanical processing which exhibits high processing stability and excellent preservability.

A further object of the present invention is to provide a direct positive light-sensitive material containing a reduced amount of a hydrazine nucleating agent, which exhibits sufficient reversal processability even when processed with a low pH processing solution.

These and other objects of the present invention are accomplished by a silver halide light-sensitive material, which comprises at least one of hydrazide compounds represented by formula (1), (2) or (3):

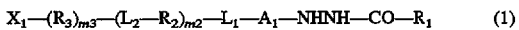

wherein $R_1$ represents a difluoromethyl group or a monofluoromethyl group; $A_1$ represent a divalent aromatic group; $X_1$ represents a group accelerating adsorption to silver halide; $R_2$ and $R_3$ each represents a divalent aliphatic or aromatic group; $L_1$ and $L_2$ each represents a divalent linking group; and $m_2$ and $m_3$ each represents 0 or 1,

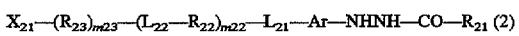

wherein $R_{21}$ represents a difluoromethyl group or a monofluoromethyl group; Ar represent a divalent aromatic group; $R_{22}$ and $R_{23}$ each represents a divalent aliphatic or aromatic group; $L_{21}$ and $L_{22}$ each represents a divalent linking group; $m_{22}$ and $m_{23}$ each represents 0 or 1; and $X_{21}$ represents an alkylthio group, an arylthio group, a heterocyclic thio group, a quaternary ammonium group, a nitrogen-containing heterocyclic group containing a quaternarized nitrogen atom, an alkoxy group containing an ethyleneoxy or propyleneoxy unit, or a saturated heterocyclic group containing a sulfide or disulfide linkage,

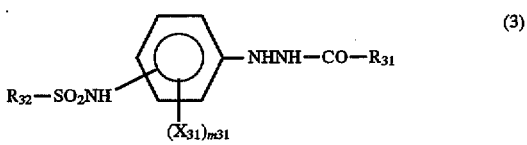

wherein $R_{31}$ represents a difluoromethyl group or a monofluoromethyl group; $R_{32}$ represents an aliphatic group, an aromatic group or a heterocyclic group, provided that a substituted phenyl group which may be represented by $R_{32}$ does not contain an aralkylamino group as a substituent; $X_{31}$ represents a substituent; and $m_{31}$ represents an integer of 0 to 4.

DETAILED DESCRIPTION OF THE INVENTION

The compounds represented by formula (1) will be explained below.

In formula (1), the divalent aromatic group as represented by $A_1$ is a monocyclic or bicyclic arylene group or a divalent aromatic heterocyclic group. The ring forming the divalent aromatic group $A_1$ includes a benzene ring, a naphthalene ring, a pyridine ring, a quinoline ring, an isoquinoline ring, a pyrrole ring, a furan ring, a thiophene ring, a thiazole ring, and an indole ring.

The divalent aromatic group as $A_1$ may have a substituent(s) other than $X_1-(R_3)_{m3}-(L_2-R_2)_{m2}-L_1$.

The substituent on $A_1$ includes a halogen atom or a group which is bonded to a ring or a main chain via a carbon atom, an oxygen atom, a nitrogen atom or a sulfur atom possessed by itself. Groups which are bonded at their carbon atom include an alkyl group, an alkenyl group, an alkynyl group, an aryl group, a carbamoyl group, an alkoxycarbonyl group, an aryloxycarbonyl group, an acyl group, an acylcarbamoyl group, a sulfonylcarbamoyl group, a carboxyl group, a cyano group, and a heterocyclic group. Groups which are bonded at their oxygen atom include a hydroxyl group, an alkoxy group, an aryloxy group, a heterocyclic oxy group, an acyloxy group, a carbamoyloxy group, and a sulfonyloxy group. Groups which are bonded at their nitrogen atom include an acylamino group, an amino group, an alkylamino group, an arylamino group, a heterocyclic amino group, a ureido group, a sulfamoylamino group, an alkoxycarbonylamino group, an aryloxycarbonylamino group, a sulfonamido group, an imido group, an oxamoylamino group, and a heterocyclic group. Groups which are bonded at their sulfur atom include an alkylthio group, an arylthio group, a heterocyclic thio group, a sulfamoyl group, an acylsulfamoyl group, an alkoxysulfonyl group, an aryloxysulfonyl group, a sulfonyl group, a sulfo group, and a sulfinyl group. These group may further be substituted with these substituents.

Going into details of the above-described substituents, the halogen atom includes a fluorine atom, a chlorine atom, and a bromine atom. The alkyl group includes a straight-chain, branched or cyclic alkyl group having 1 to 16 carbon atoms, preferably 1 to 10 carbon atoms, such as methyl, ethyl, isopropyl, t-butyl, benzyl, and cyclopentyl groups. The alkenyl group includes one containing 2 to 16 carbon atoms, such as vinyl, 1-propenyl, 1-hexenyl, and styryl groups. The alkynyl group includes one containing 2 to 16 carbon atoms, such as ethynyl, 1-butynyl, 1-dodecenyl, and phenylethynyl groups. The aryl group includes one having 6 to 24 carbon atoms, such as phenyl, naphthyl and p-methoxyphenyl groups. The carbamoyl group includes one having 1 to 18 carbon atoms, such as carbamoyl, N-ethylcarbamoyl, N-octylcarbamoyl, and N-phenylcarbamoyl groups. The alkoxycarbonyl group includes one having 2 to 18 carbon atoms, such as methoxycarbonyl and benzyloxycarbonyl groups. The aryloxycarbonyl group includes one having 7 to 18 carbon atoms, such as a phenoxycarbonyl group. The acyl group includes one having 1 to 18 carbon atoms, such as acetyl and benzoyl groups. The heterocyclic group which is bonded at the carbon atom of its ring includes a 5- or 6-membered saturated or unsaturated hetero ring containing 1 to 5 carbon atoms and one or more hetero atoms selected from an oxygen atom, a nitrogen atom and a sulfur atom (the two or more hetero atoms may be the same or different), such as 2-furyl, 2-thienyl, 2-pyridyl, and 2-imidazolyl groups. The acylcarbamoyl group includes one having 1 to 18 carbon atoms, such as N-acetylcarbamoyl and N-benzoylcarbamoyl groups. The sulfonylcarbamoyl group includes one having 1 to 18 carbon atoms, such as N-methanesulfonylcarbamoyl and N-benzenesulfonylcarbamoyl groups. The alkoxy group include one having 1 to 16 carbon atoms, preferably 1 to 10 carbon atoms, such as methoxy, 2-methoxyethoxy, and 2-methanesulfonylethoxy groups. The aryloxy group includes one having 6 to 24 carbon atoms, such as phenoxy, p-methoxyphenoxy, and m-(3-hydroxypropionamido) phenoxy groups. The heterocyclic oxy group includes a 5- or 6-membered saturated or unsaturated heterocyclic oxy group containing 1 to 5 carbon atoms and one or more hetero atoms selected from an oxygen atom, a nitrogen atom and a sulfur atom (the two or more hetero atoms may be the same or different), such as 1-phenyltetrazolyl-5-oxy, 2-tetrahydropyranyloxy and 2-pyridyloxy groups. The acyloxy group includes one having 1 to 16 carbon atoms, preferably 1 to 10 carbon atoms, such as acetoxy, benzoyloxy, and 4-hydroxybutacarbamoyloxy groups. The carbamoyloxy group includes one having 1 to 16 carbon atoms, preferably 1 to 10 carbon atoms, such as N,N-dimethylcarbamoyloxy, N-hexylcarbamoyloxy, and N-phenylcarbamoyloxy groups. The sulfonyloxy group includes one having 1 to 16 carbon atoms, such as methanesulfonyloxy and benzenesulfonyloxy groups. The acylamino group includes one having 1 to 16 carbon atoms, preferably 1 to 10 carbon atoms, such as acetamido and p-chlorobenzoylamido groups. The alkylamino group includes one having 1 to 16 carbon atoms, preferably 1 to 10 carbon atoms, such as N,N-dimethylamino and N-(2-hydroxyethyl)amino groups. The arylamino group include one having 6 to 24 carbon atoms, such as anilino and N-methylanilino groups. The heterocyclic amino group includes a 5- or 6-membered saturated or unsaturated heterocyclic amino group containing 1 to 5 carbon atoms and one or more hetero atoms selected from an oxygen atom, a nitrogen atom and a sulfur atom (the two or more hetero atoms may be the same or different), such as 2-oxazolylamino, 2-tetrahydropyranylamino, and 4-pyridylamino groups. The ureido group include one having 1 to 16 carbon atoms, preferably 1 to 10 carbon atoms, such as ureido, methylureido, N,N-diethylureido, and 2-methanesulfonamidoethylureido groups. The sulfamoylamino group includes one having 0 to 16 carbon atoms, preferably up to 10 carbon atoms, such as methylsulfamoylamino and 2-methoxyethylsulfamoylamino groups. The alkoxycarbonylamino group includes one having 2 to 16 carbon atoms, preferably 2 to 10 carbon atoms, such as methoxycarbonylamino group. The aryloxycarbonylamino group includes one having 7 to 24 carbon atoms, such as phenoxycarbonylamino and 2,6-dimethoxyphenoxycarbonylamino group. The sulfonamido group includes one having 1 to 16 carbon atoms, preferably 1 to 10 carbon atoms, such as methanesulfonamido and p-toluenesulfonamido groups. The imido group includes one having 4 to 16 carbon atoms, such as N-succinimido and N-phthalimido groups. The oxamoylamino group includes one having 2 to 16 carbon atoms, preferably 2 to 10 carbon atoms, such as N-ethyloxamoylamino group. The heterocyclic group which is bonded at the nitrogen atom of its ring includes a 5- or 6-membered heterocyclic ring containing a nitrogen atom and at least one of a carbon atom, an oxygen atom and a sulfur atom, such as pyrrolidino, morpholino and imidazolino groups. The alkylthio group includes one having 1 to 16 carbon atoms, preferably 1 to 10 carbon atoms, such as methylthio and 2-phenoxyethylthio groups. The arylthio group includes one having 6 to 24 carbon atoms, such as phenylthio and 2-carboxyphenylthio groups. The heterocyclic thio group includes a 5- or 6-membered saturated or unsaturated heterocyclic thio group containing 1 to 5 carbon atoms and one or more hetero atoms selected from an oxygen atom, a nitrogen atom and a sulfur atom (the two or more hetero atoms may be the same or different), such as 2-benzothiazolylthio and 2-pyridylthio groups. The sulfamoyl group includes one having 0 to 16 carbon atoms, preferably up to 10 carbon atoms, such as sulfamoyl, methylsulfamoyl, and phenylsulfamoyl groups. The alkoxysulfonyl group includes one having 1 to 16 carbon atoms, preferably 1 to 10 carbon atoms, such as a methoxysulfonyl group. The aryloxysulfonyl group includes one having 6 to 24 carbon atoms, preferably 6 to 12 carbon atoms, such as a phenoxysulfonyl group. The sulfonyl group includes one having 1 to 16 carbon atoms, preferably 1 to 10 carbon atoms, such as methanesulfonyl and benzenesulfonyl groups. The sulfinyl group includes one having 1 to 16 carbon atoms, preferably 1 to 10 carbon atoms, such as methanesulfinyl and benzenesulfinyl groups. The acylsulfamoyl group includes one having 1 to 18 carbon atoms, preferably 1 to 16 carbon atoms, such as N-acetylsulfamoyl and N-benzoylsulfamoyl groups.

The aromatic group as $A_1$ is preferably a monocyclic arylene group, still preferably a phenylene group.

As stated above, a phenylene group as $A_1$ may have a substituent(s) other than $X_1-(R_3)_{m3}-(L_2-R_2)_{m2}-L_1$. Preferred of the above-enumerated substituents are an alkyl group, an alkoxy group, a hydroxyl group, an amino group, an alkylamino group, an acylamino group, a sulfonamido group, a ureido group, a halogen atom, a carboxyl group, and a sulfo group.

In formula (1), $X_1$ represents a group accelerating adsorption onto silver halide (hereinafter simply referred to as an adsorption accelerating group).

Preferred examples of the adsorption accelerating group are a thioamido group, a mercapto group, and a 5- or 6-membered nitrogen-containing heterocyclic group.

The thioamido adsorption accelerating group is a divalent group represented by:

which may be part of a cyclic structure. An acyclic thioamido group is preferred. Suitable thioamido adsorption accelerating groups are selected from those described in U.S. Pat. Nos. 4,030,925, 4,031,127, 4,080,207, 4,245,037, 4,255,511, 4,266,013, and 4,276,364 and *Research Disclosure*, Vol. 151, No. 15162 (November, 1976), and ibid, Vol. 176, No. 17626 (December, 1978). Thioamido groups represented by formula (A) shown below are particularly preferred.

wherein either E or E' represents $-N(R^{62})-$, and the other represents $-O-$, $-S-$ or $-N(R^{62})-$, wherein $R^{62}$ represents a hydrogen atom, an aliphatic group or an aromatic group; and $R^{61}$ represents a hydrogen atom, an aliphatic group or an aromatic group, or $R^{62}$ is taken together with E or E' to form a 5- or 6-membered ring.

Thioamides providing the thioamido group of formula (A) include thioureas, thiourethanes, and dithiocarbamic esters. Cyclic thioamides providing the thioamido group of formula (A) in which E or E' and $R^{62}$ are taken together to form a ring include those used as acidic nucleus of merocyanine dyes, such as 4-thiazoline-2-thione, thiazolidine-2-thione, 4-oxazoline-2-thione, oxazolidine-2-thione, 2-pyrazoline-5- thione, 4-imidazoline-2-thione, 2-thiohydantoin, rhodanine, isorhodanine, 2-thio-2,4-oxazolidinedione, thiobarbituric acid, tetrazoline-5-thione, 1,2,4-triazoline-3-thione, 1,3,4-thiadiazoline-2-thione, 1,3,4-oxadiazoline-2-thione, benzimidazoline-2-thione, benzoxazoline-2-thione, and benzothiazoline-2-thione. These compounds may be substituted.

The mercapto adsorption accelerating group includes an aliphatic mercapto group, an aromatic mercapto group, and a heterocyclic mercapto group (a heterocyclic mercapto group in which SH is bonded to a carbon atom next to a nitrogen atom is included under the above-mentioned ring-forming thioamido group as tautomers). The aliphatic mercapto group includes a mercaptoalkyl group (e.g., mercaptoethyl, mercaptopropyl), a mercaptoalkenyl group (e.g., mercaptopropenyl), and a mercaptoalkynyl group (e.g., mercaptobutynyl). The aromatic mercapto group includes a mercaptophenyl group and a mercaptonaphthyl group. The heterocyclic mercapto group includes those mentioned above as ring-forming thioamide group and a 4-mercaptopyridyl group, a 5-mercaptoquinolinyl group, and a 6-mercaptobenzothiazolyl group.

The 5- or 6-membered nitrogen-containing heterocyclic adsorption accelerating group includes a 5- or 6-membered heterocyclic group made up of a combination of nitrogen, oxygen, sulfur and carbon atoms. Preferred are those derived from benzotriazole, triazole, tetrazole, indazole, benzimidazole, imidazole, benzothiazole, thiazole, benzoxazole, oxazole, thiadiazole, oxadiazole, and triazine. These groups may have an appropriate substituent(s). Still preferred are those capable of forming imino silver, such as those derived from benzotriazole, triazole, tetrazole, and indazole. A benzotriazole residue is particularly preferred.

Specific examples of preferred nitrogen-containing heterocyclic groups are benzotriazol-5-yl, 6-chlorobenzotriazol-5-yl, benzotriazole-5-carbonyl, 5-phenyl-1,3,4-triazol-2-yl, 4-(5-methyl-1,3,4-triazol-2-yl)benzoyl, 1H-tetrazol-5-yl, and 3-cyanoindazol-5-yl.

$X_1$ is preferably a cyclic thioamido group (i.e., a mercapto-substituted nitrogen-containing heterocyclic group, e.g., 2-mercaptothiadiazole, 3-mercapto-1,2,4-triazole, 5-mercaptotetrazole, 2-mercapto-1,3,4-oxadiazole, 2-mercaptobenzoxazole) or a nitrogen-containing heterocyclic group (e.g., benzotriazole, benzimidazole, indazole).

$X_1$ still preferably represents a 5-mercaptotetrazole group, a 3-mercapto-1,2,4-triazole group or a benzotriazole group, with a 3-mercapto-1,2,4-triazole group and a 5-mercaptotetrazole group being particularly preferred.

The terminology "adsorption accelerating group" as used herein is also intended to include a precursor of an adsorption accelerating group. The terminology "precursor" as referred to above denotes such a group as has a precursor group capable of producing an adsorption accelerating group rapidly on being processed with a development processing solution at the time of development processing.

The precursor group is preferably such that is hydrolyzed with a nucleophilic species present in a developer, such as a hydroxide ion (OH⁻) or a sulfite ion ($SO_3^{2-}$), or decomposed with a development processing solution (cross-oxidation reaction with an imagewise occurring oxidation product of a developing agent acts as a trigger).

Precursor groups of the former type include those described in JP-A-2-285344, such as an alkoxycarbonyl group, an aryloxycarbonyl group, a carbamoyl group, an acyl group, a 1,3,3a,7-tetrazainden-4-yl group, a uracil group, a 3-oxo-1-cyclopentenyl group, a triazin-1-yl group, and a group represented by the following formula:

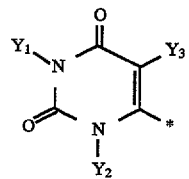

wherein * indicates the position to bond to an adsorption accelerating group; $Y_1$ and $Y_2$ each represents a hydrogen atom, a substituted or unsubstituted alkyl or aryl group; $Y_3$ represents a hydrogen atom, a halogen atom, an alkylthio group, an arylthio group, a sulfonyl group, a sulfinyl group, an alkoxy group, an aryloxy group, or an alkyl group.

Precursor groups of the latter type include those having a hydroquinone skeleton which are represented by formula:

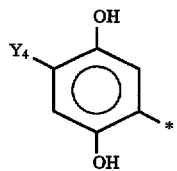

wherein * indicates the position to bond to an adsorption accelerating group; $Y_4$ represents a substituent, preferably an N'-substituted ureido group, an acylamino group, a sulfonamido group, an alkylthio group or an arylthio group.

In formula (1), $R_2$ and $R_3$ each represents a divalent aliphatic or aromatic group.

The divalent aliphatic group is a substituted or unsubstituted and straight-chain, branched or cyclic alkylene, alkenylene or alkynylene group, and the divalent aromatic group is a monocyclic or bicyclic arylene group.

$R_2$ or $R_3$ preferably represents an alkylene or arylene group. Still preferably $R_2$ is a phenylene group, and $R_3$ is a phenylene group or an alkylene group.

The aliphatic or aromatic group as $R_2$ or $R_3$ may have a substituent(s) selected from those described as the substituents $A_1$ may have. Preferred substituents on $R_2$ or $R_3$ include a halogen atom, an alkyl group, an aryl group, a carbamoyl group, an alkoxycarbonyl group, an aryloxycarbonyl group, an acyl group, a cyano group, an alkoxy group, an aryloxy group, a carbamoyloxy group, an acylamino group, a ureido group, a sulfamoylamino group, an alkoxycarbonylamino group, a sulfonamido group, a sulfamoyl group, and a sulfonyl group. An alkyl group, an aryl group, a carbamoyl group, an alkoxy group, an acylamino group, a ureido group, a sulfonamido group, and a sulfamoyl group are still preferred substituents.

In formula (1), the divalent linking group represented by $L_1$ or $L_2$ includes —O—, —S—, —N($R_{N1}$)— (wherein $R_{N1}$ represents a hydrogen atom, an alkyl group or an aryl group), —CO—, —SO₂—, and groups made up of a combination of these linking atoms or groups. Examples of linking groups made up of a combination are —CON($R_{N1}$)—, —SO₂N($R_{N1}$)—, —COO—, —N($R_{N1}$)CON($R_{N1}$)—, —SO₂N($R_{N1}$)CO—, —SO₂N($R_{N1}$)CON($R_{N1}$)—, —N($R_{N1}$)COCON($R_{N1}$)—, and —N($R_{N1}$)SO₂N($R_{N1}$)—. The plurality of $R_{N1}$'s may be the same or different.

$L_1$ is preferably —SO₂NH—, —NHCONH—, —O—, —S— or —N($R_{N1}$)—, still preferably —SO₂NH— or —NHCONH—.

$L_2$ is preferably —CON($R_{N1}$)—, —SO₂NH—, —NHCONH—, —N($R_{N1}$)CONH— or —COO—. When $L_2$ is —CON($R_{N1}$)— or —N($R_{N1}$)CONH—, $R_{N1}$ may represent —$R_3$—X in formula (1) as a substituted alkyl group.

Of the compounds of formula (1) preferred are those represented by formula (11):

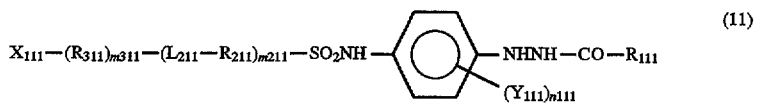
(11)

wherein $X_{111}$, $R_{111}$, $R_{211}$, $R_{311}$, $L_{211}$, $m_{211}$, and $m_{3111}$ have the same meaning as $X_1$, $R_1$, $R_2$, $R_3$, $L_2$, $m_2$, and $m_3$ of formula (1), respectively; $Y_{111}$ represents a substituent; and $n_{111}$ represents an integer of 0 to 4.

In formula (11), the substituent as $Y_{111}$ includes those enumerated as the substituents $A_1$ can have. The preferred substituents described for $A_1$ also apply to the substituents on $Y_{111}$. $n_{111}$ preferably represents 0 or 1, still preferably 0.

Specific examples of the hydrazine compounds of formula (1) which can be used in the invention are listed below for illustrative purposes but not for limitation.

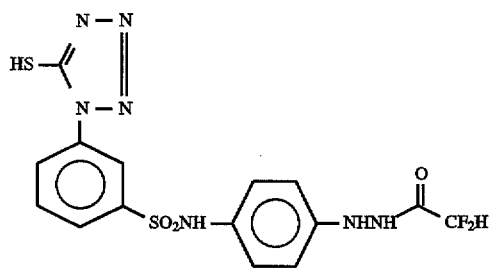

1-1

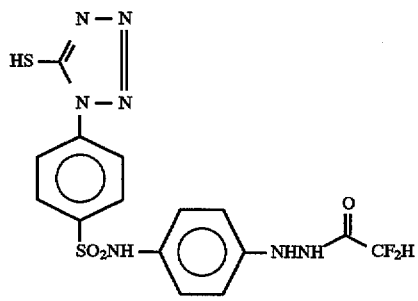

1-2

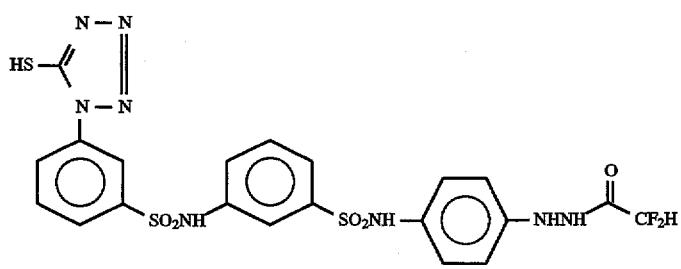

1-3

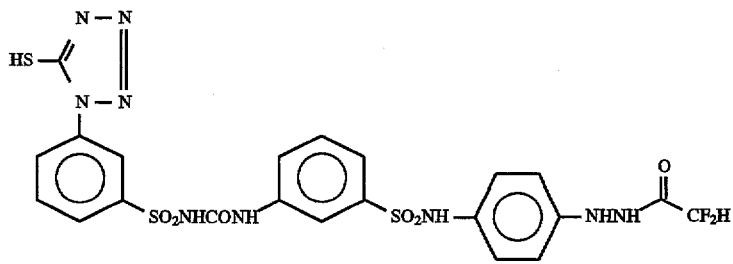

1-4

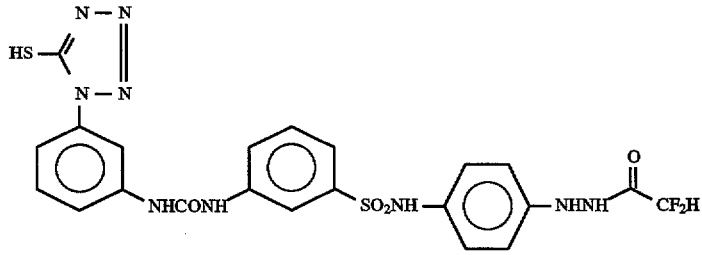

1-5

-continued
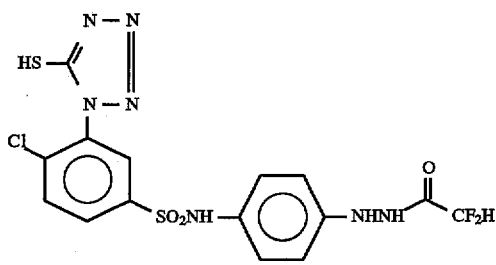
1-6
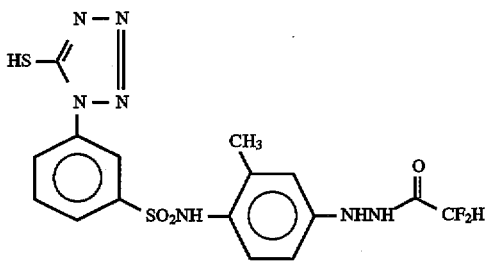
1-7
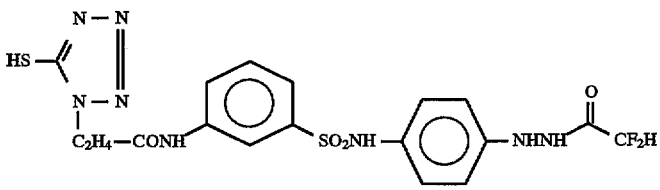
1-8
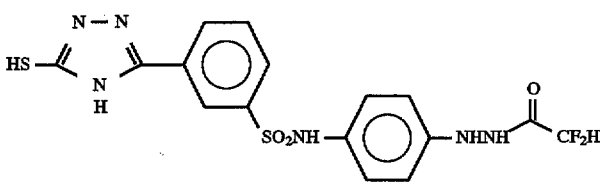
1-9
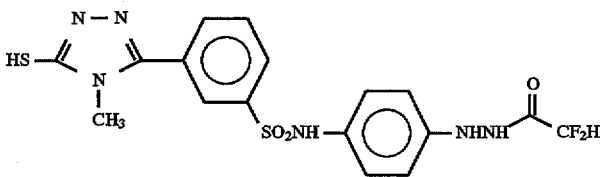
1-10
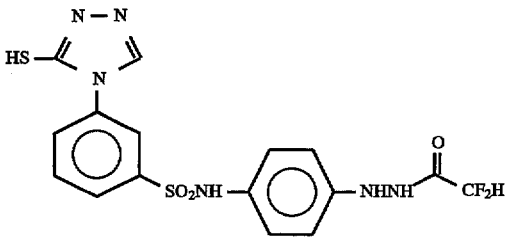
1-11
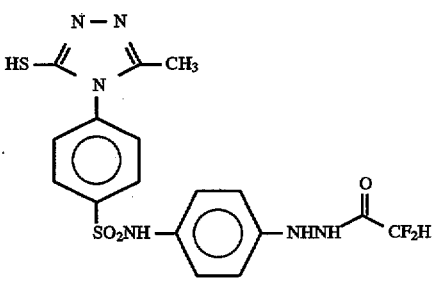
1-12

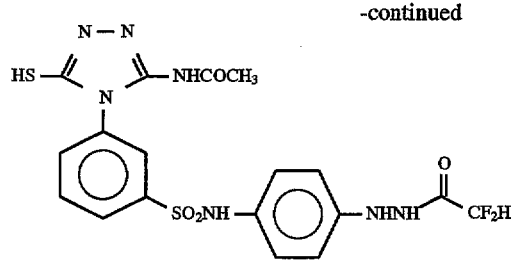
1-13
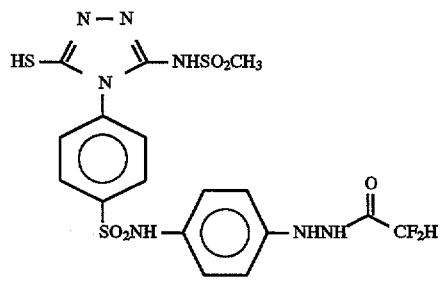
1-14
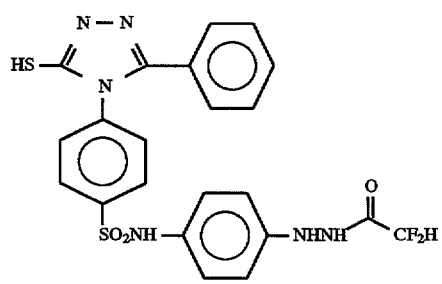
1-15
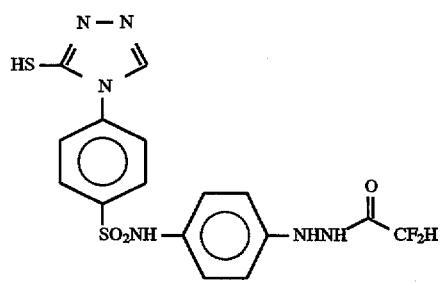
1-16
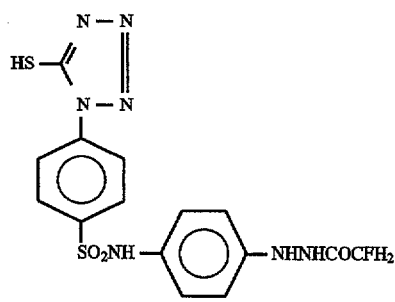
1-17
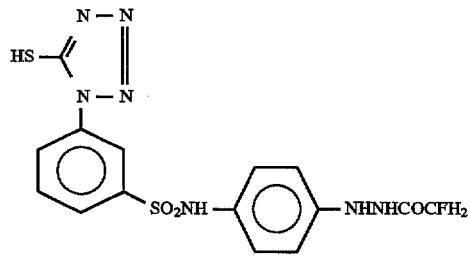
1-18

-continued
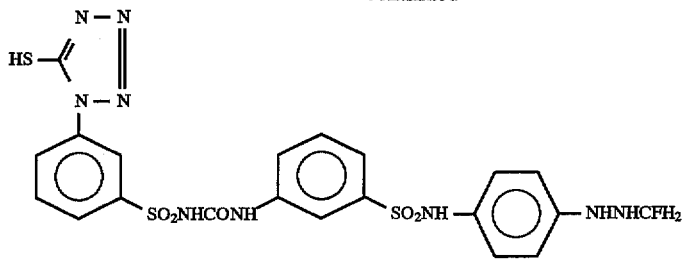
1-19
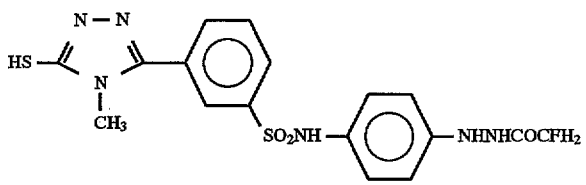
1-20
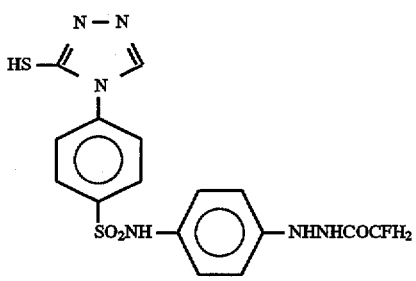
1-21
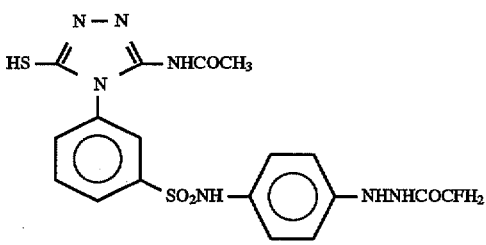
1-22
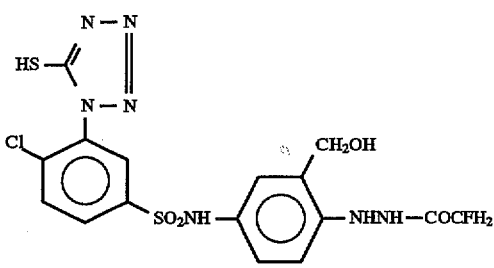
1-23
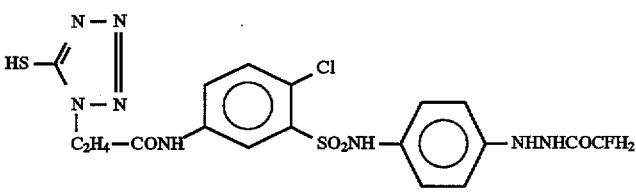
1-24
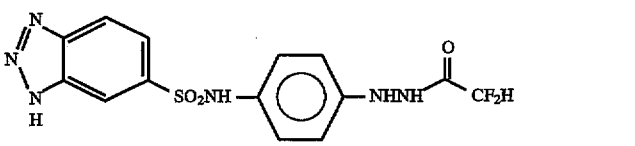
1-25

-continued
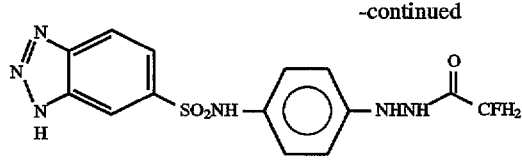
1-26
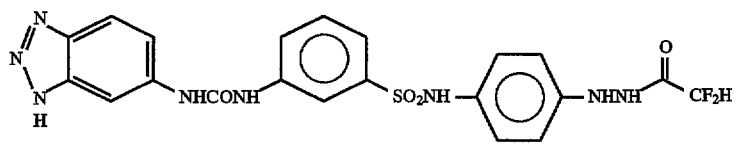
1-27
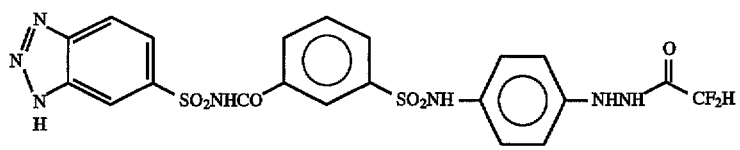
1-28
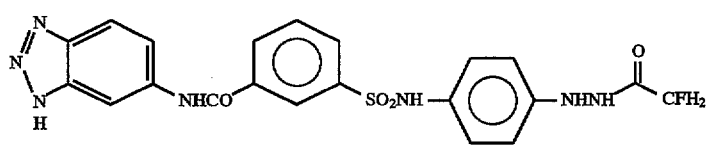
1-29
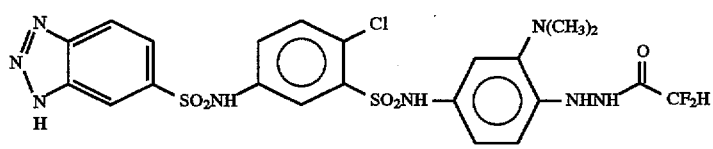
1-30
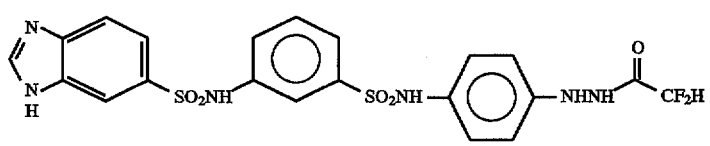
1-31
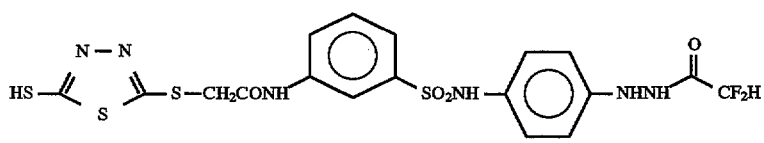
1-32
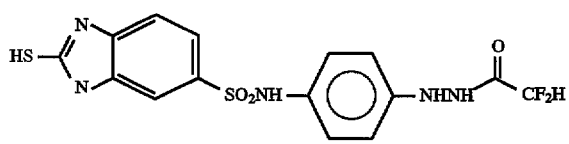
1-33
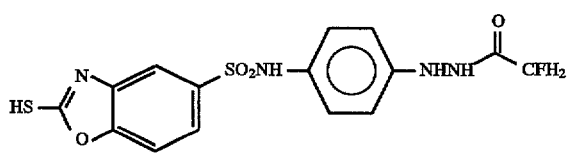
1-34
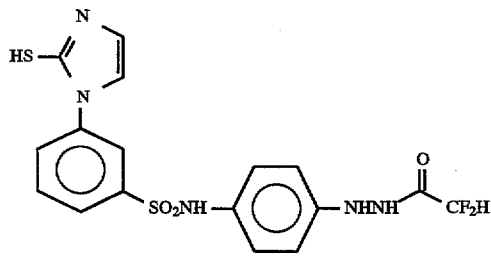
1-35

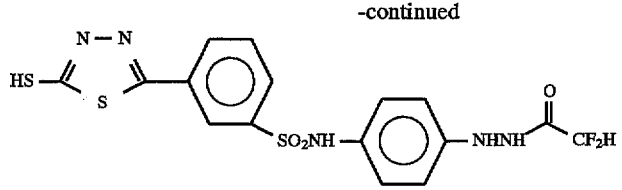
1-36
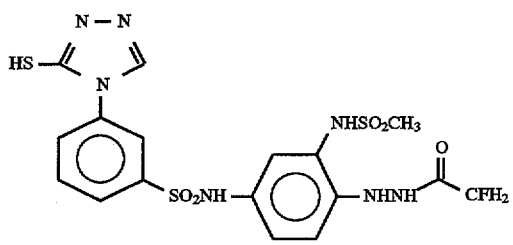
1-37
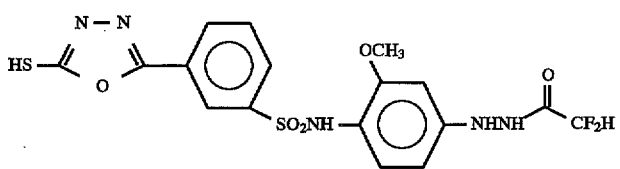
1-38
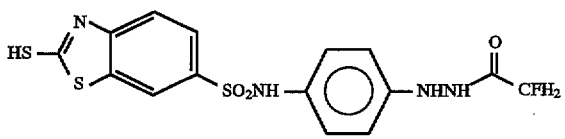
1-39
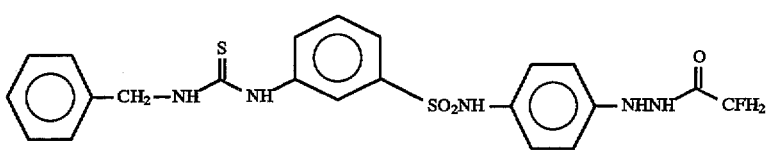
1-40
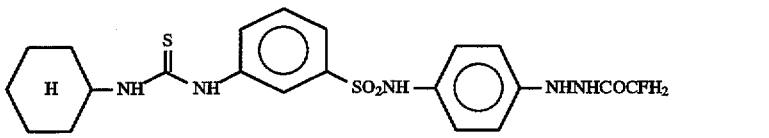
1-41
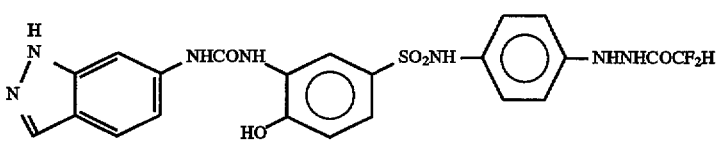
1-42
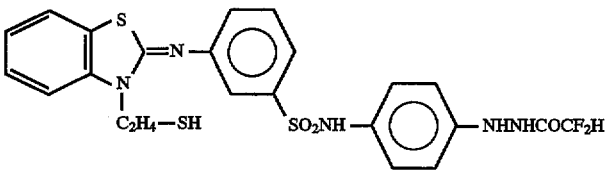
1-43
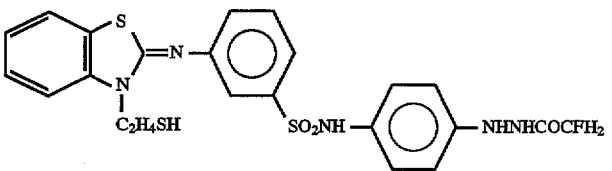
1-44

-continued
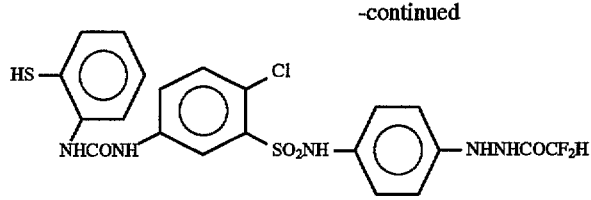 1-45
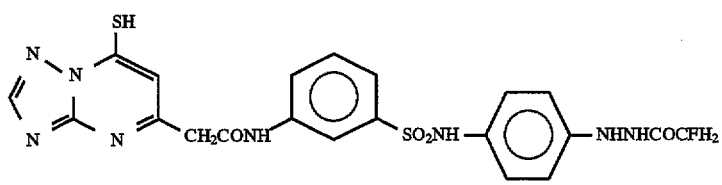 1-46
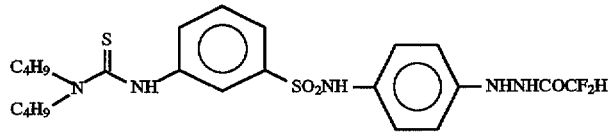 1-47
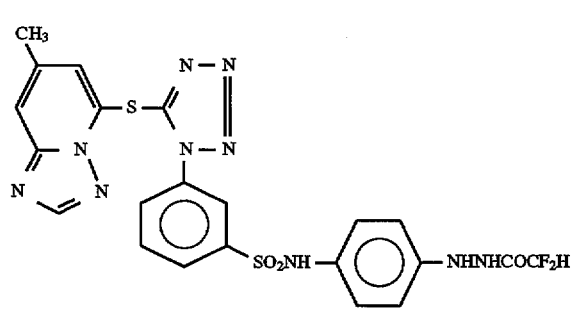 1-48
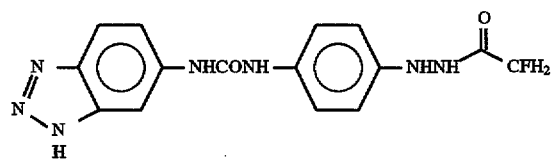 1-49
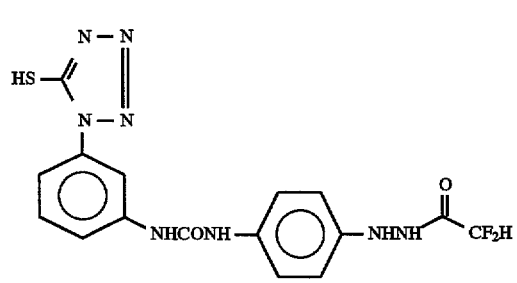 1-50
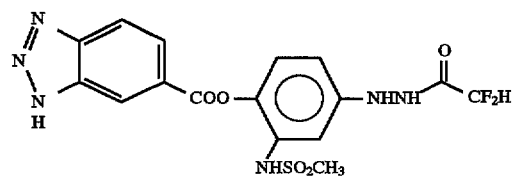 1-51
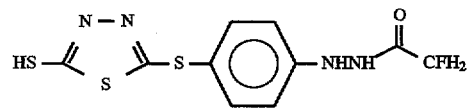 1-52

-continued
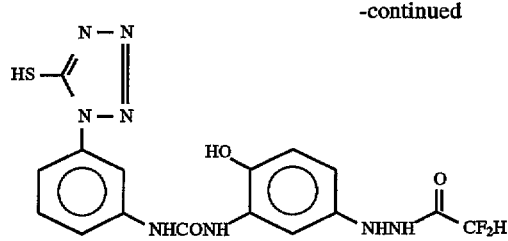
1-53
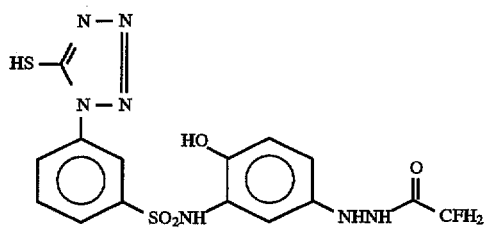
1-54
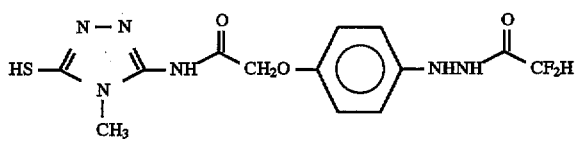
1-55
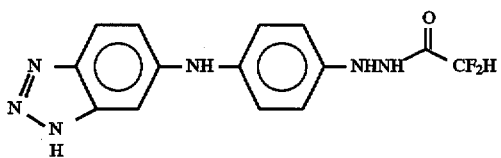
1-56
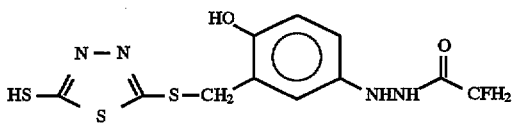
1-57
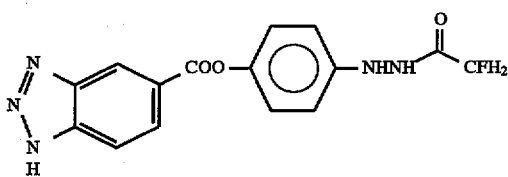
1-58
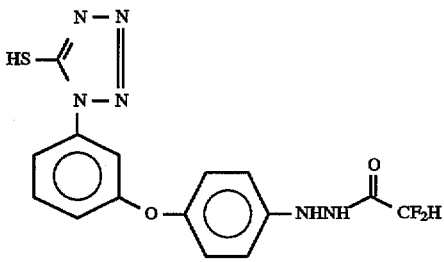
1-59
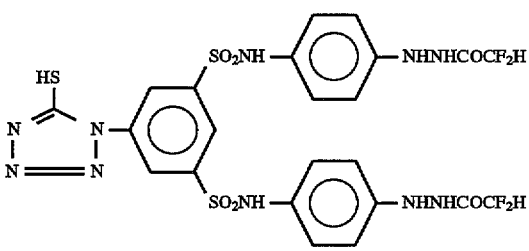
1-60

-continued
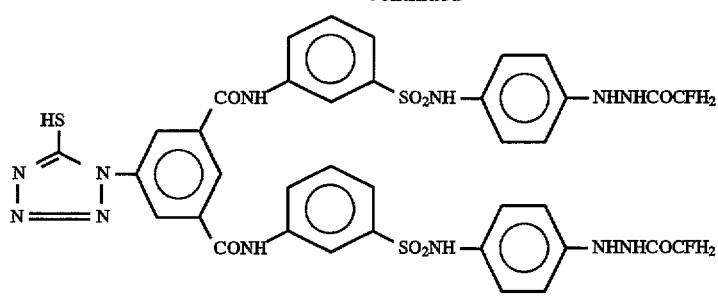
1-61
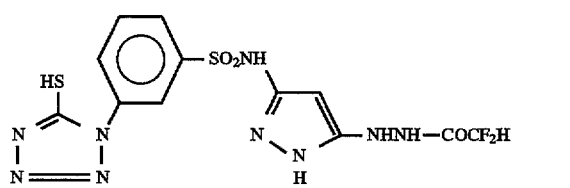
1-63
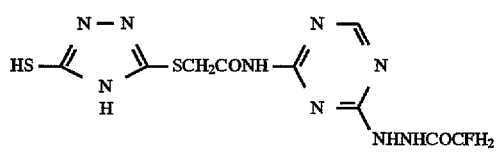
1-64
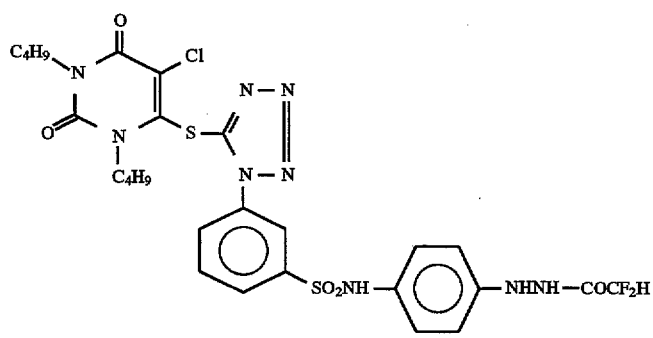
1-65
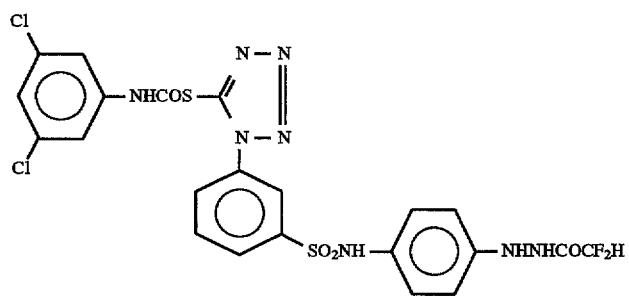
1-66
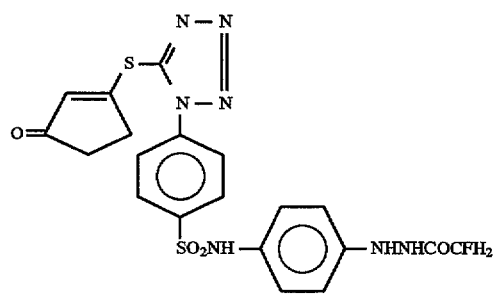
1-67

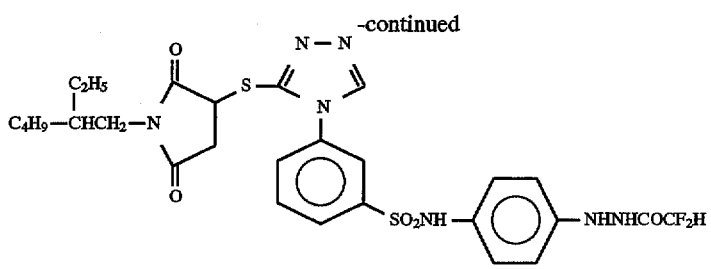

1-68

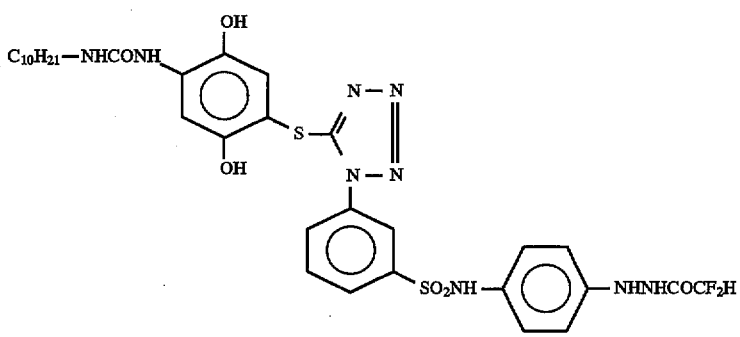

1-69

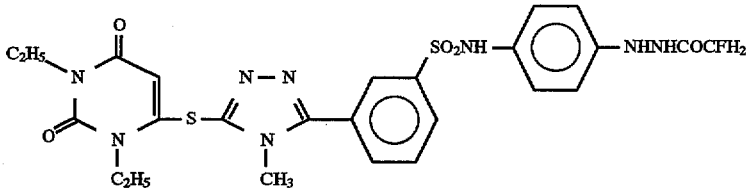

1-70

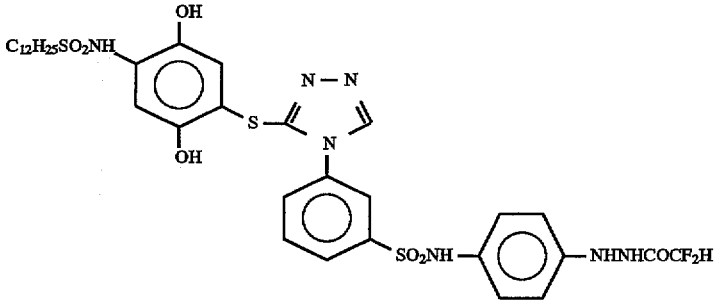

1-71

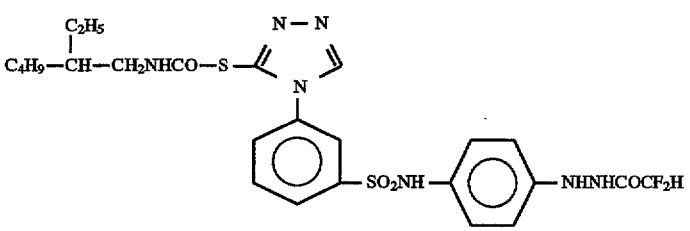

1-72

The hydrazine compound of formula (1) can easily be synthesized by condensing a hydrazine derivative and difluoroacetic acid or monofluoroacetic acid using an appropriate condensing agent or by reacting a hydrazine derivative with an anhydride of the acid as illustrated in reaction scheme 1 shown below.

Reaction Scheme 1:

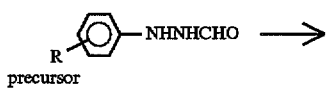

precursor

-continued
Reaction Scheme 1:

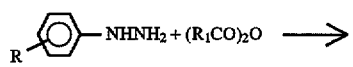

or

-continued
Reaction Scheme 1:

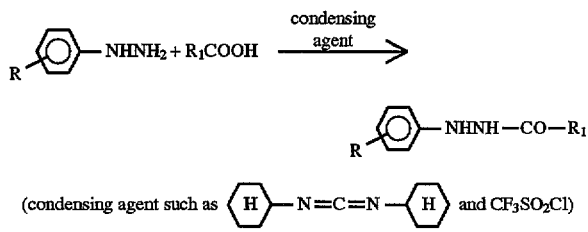

wherein R: substituent having an adsorption accelerating group;

$R_1$: $CF_2H$ or $CFH_2$)

Condensing agents used for amidation, such as dicyclohexylcarbodiimide or trifluoromethanesulfonyl chloride, are effective used. A formylhydrazine derivative can be used as a hydrazine derivative precursor.

SYNTHESIS EXAMPLE 1

Synthesis of Compound 1-5

Compound (1) described in JP-A-63-234244 having the formula shown below was synthesized by the process described therein. The compound was designated intermediate 5-(1).

Intermediate 5-(1):

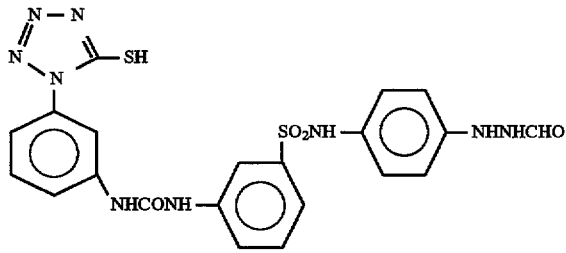

To a suspension of 10.0 g of intermediate 5-(1) in 300 ml of methanol was added 4.1 g of 1,5-dinaphthalenesulfonic acid, and the mixture was stirred at 50° C. for 2 hours. The reaction mixture was concentrated under reduced pressure to remove methanol, acetonitrile was added to the residue, and the precipitated crystals were collected by filtration and dried in air to give 10.8 g of a 1,5-dinaphthalenesulfonate of the hydrazine derivative as an intermediate.

In 20 ml of dimethylformamide (DMF) were suspended 6.0 g of the resulting hydrazine derivative salt and 0.9 g of difluoroacetic acid, and 10 m of a DMF solution of 1.18 g of dicyclohexylcarbodiimide (DCC) was slowly added thereto dropwise at room temperature. After the addition, the mixture was stirred for 2 hours, cooled, and filtered. The filtrate was extracted with ethyl acetate, the extract was washed with diluted hydrochloric acid, and concentrated under reduced pressure to give a crude reaction product.

The crude product was purified by column chromatography to obtain 2.3 g of compound 1-5 as amorphous crystals.

SYNTHESIS EXAMPLE 2

Synthesis of Compound 1-1

Compound 1-1 was synthesized in the same manner as in Synthesis Example 1 except for replacing intermediate 5-(1) with intermediate 1-(1) shown below.

Melting point: 178° C. (with decomposition)

Intermediate 1-(1):

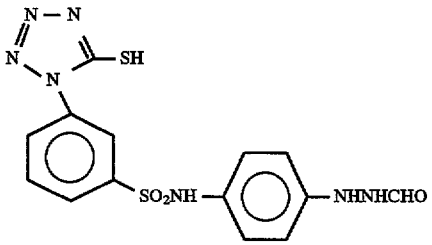

Intermediate 1-(1) was synthesized as follows.
Synthesis of Intermediate 1-(1):

In 150 ml of acetonitrile was suspended 50 g of sodium 3-(5-mercaptotetrazolyl)benzenesulfonate, and 30 ml of triethylamine was added thereto at room temperature. After stirring for 10 minutes, 25 ml of phenyl chloroformate was slowly added thereto dropwise under cooling with ice, followed by stirring at room temperature for 30 minutes. The precipitated crystals were separated by filtration, and the filtrate was concentrated under reduced pressure to give a crude reaction product To the crude reaction product was added 25 ml of acetonitrile, and 30 ml of phosphorus oxychloride was added while ice-cooling. Ten milliliters of dimethylacetamide were added thereto dropwise, followed by stirring at 10° C. for 2 hours.

Water (300 ml) was added to the reaction mixture slowly at first. After adding the whole amount of water, the reaction mixture was filtered to collect the precipitated crystals, which were washed with water and dried in air to give 58.1 g of 3-(5-mercaptotetrazolyl)benzenesulfonyl chloride.

In 100 ml of methanol was suspended 15.1 g of 1-formyl-2-(4-aminophenyl)hydrazine, and 12 ml of N-methylmorpholine was added to the suspension. To the suspension was slowly added dropwise 150 ml of an acetonitrile solution of 19.8 g of 3-(5-mercaptotetrazolyl)benzenesulfonyl chloride under ice-cooling, followed by stirring at 5° C. for 1 hours. The solvent was removed by evaporation under reduced pressure, and 100 ml of water was added to the residue. After stirring, the unnecessary crystals thus precipitated were removed by filtration, and the filtrate was made acidic with diluted hydrochloric acid. The precipitated crystals were collected by filtration, washed by pouring water on the filter, and dried in air to give 14.2 g of intermediate 1-(1).

SYNTHESIS EXAMPLE 3

Synthesis of Compound 1-16

Intermediate 16-(1) was obtained in the same manner as for intermediate 1-(1) except for replacing sodium 3-(5-mercaptotetrazol-1-yl)benzenesulfonate with sodium 3-(2-mercapto-1,3,4-triazol-1-yl)benzenesulfonate.

Intermediate 16-(1):

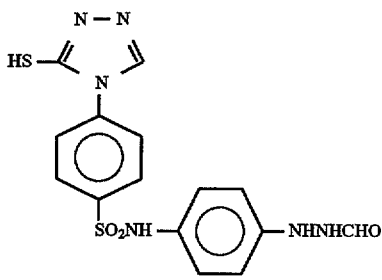

Compound 1-16 was synthesized in the same manner as in Synthesis Example 1 except for replacing intermediate 5-(1) with intermediate 16-(1).

Melting point: 209° C. (with decomposition)

SYNTHESIS EXAMPLE 4

Synthesis of Compound 1-12

Compound 1-12 was synthesized in the same manner as for compound 1-16 except for replacing sodium 3-(2-mercapto-1,3,4-triazol-1-yl)benzenesulfonate with sodium 3-(2-mercapto-5-methyl-1,3,4-triazol-1-yl) benzenesulfonate.

Melting point: 225°–227° C.

The compounds represented by formula (2) will be explained below.

In formula (2), the divalent aromatic group as represented by Ar is a monocyclic or bicyclic arylene group or a divalent aromatic heterocyclic group. The ring providing the divalent aromatic group Ar includes a benzene ring, a naphthalene ring, a pyridine ring, a quinoline ring, an isoquinoline ring, a pyrrole ring, a furan ring, a thiophene ring, a thiazole ring, and an indole ring.

The divalent aromatic group as Ar may have a substituent (s).

The substituent on Ar includes a halogen atom or a group which is bonded to a ring or a main chain via a carbon atom, an oxygen atom, a nitrogen atom or a sulfur atom possessed by itself. Groups which are bonded at their carbon atom include an alkyl group, an alkenyl group, an alkynyl group, an aryl group, a carbamoyl group, an alkoxycarbonyl group, an aryloxycarbonyl group, an acyl group, an acylcarbamoyl group, a sulfonylcarbamoyl group, a carboxyl group, a cyano group, and a heterocyclic group. Groups which are bonded at their oxygen atom include a hydroxyl group, an alkoxy group, an aryloxy group, a heterocyclic oxy group, an acyloxy group, a carbamoyloxy group, and a sulfonyloxy group. Groups which are bonded at their nitrogen atom include an acylamino group, an amino group, an alkylamino group, an arylamino group, a heterocyclic amino group, a ureido group, a sulfamoylamino group, an alkoxycarbonylamino group, an aryloxycarbonylamino group, a sulfonamido group, an imido group, an oxamoylamino group, and a heterocyclic group. Groups which are bonded at their sulfur atom include an alkylthio group, an arylthio group, a heterocyclic thio group, a sulfamoyl group, an acylsulfamoyl group, an alkoxysulfonyl group, an aryloxysulfonyl group, a sulfonyl group, a sulfo group, and a sulfinyl group. These group may further be substituted with these substituents.

Going into details of the above-described substituents, the halogen atom includes a fluorine atom, a chlorine atom, and a bromine atom. The alkyl group includes a straight-chain, branched or cyclic alkyl group having 1 to 16 carbon atoms, preferably 1 to 10 carbon atoms, such as methyl, ethyl, isopropyl, t-butyl, benzyl, and cyclopentyl groups. The alkenyl group includes one containing 2 to 16 carbon atoms, such as vinyl, 1-propenyl, 1-hexenyl, and styryl groups. The alkynyl group includes one containing 2 to 16 carbon atoms, such as ethynyl, 1-butynyl, 1-dodecenyl, and phenylethynyl groups. The aryl group includes one having 6 to 24 carbon atoms, such as phenyl, naphthyl and p-methoxyphenyl groups. The carbamoyl group includes one having 1 to 18 carbon atoms, such as carbamoyl, N-ethylcarbamoyl, N-octylcarbamoyl, and N-phenylcarbamoyl groups. The alkoxycarbonyl group includes one having 2 to 18 carbon atoms, such as methoxycarbonyl and benzyloxycarbonyl groups. The aryloxycarbonyl group includes one having 7 to 18 carbon atoms, such as a phenoxycarbonyl group. The acyl group includes one having 1 to 18 carbon atoms, such as acetyl and benzoyl groups. The heterocyclic group which is bonded at the carbon atom of its ring includes a 5- or 6-membered saturated or unsaturated hetero ring containing 1 to 5 carbon atoms and one or more hetero atoms selected from an oxygen atom, a nitrogen atom and a sulfur atom (the two or more hetero atoms may be the same or different), such as 2-furyl, 2-thienyl, 2-pyridyl, and 2-imidazolyl groups. The acylcarbamoyl group includes one having 1 to 18 carbon atoms, such as N-acetylcarbamoyl and N-benzoylcarbamoyl groups. The sulfonylcarbamoyl group includes one having 1 to 18 carbon atoms, such as N-methanesulfonylcarbamoyl and N-benzenesulfonylcarbamoyl groups. The alkoxy group include one having 1 to 16 carbon atoms, preferably 1 to 10 carbon atoms, such as methoxy, 2-methoxyethoxy, and 2-methanesulfonylethoxy groups. The aryloxy group includes one having 6 to 24 carbon atoms, such as phenoxy, p-methoxyphenoxy, and m-(3-hydroxypropionamido) phenoxy groups. The heterocyclic oxy group includes a 5- or 6-membered saturated or unsaturated heterocyclic oxy group containing 1 to 5 carbon atoms and one or more hetero atoms selected from an oxygen atom, a nitrogen atom and a sulfur atom (the two or more hetero atoms may be the same or different), such as 1-phenyltetrazolyl-5-oxy, 2-tetrahydropyranyloxy and 2-pyridyloxy groups. The acyloxy group includes one having 1 to 16 carbon atoms, preferably 1 to 10 carbon atoms, such as acetoxy, benzoyloxy, and 4-hydroxybutanoyloxy groups. The carbamoyloxy group includes one having 1 to 16 carbon atoms, preferably 1 to 10 carbon atoms, such as N,N-dimethylcarbamoyloxy, N-hexylcarbamoyloxy, and N-phenylcarbamoyloxy groups. The sulfonyloxy group includes one having 1 to 16 carbon atoms, such as methanesulfonyloxy and benzenesulfonyloxy groups. The acylamino group includes one having 1 to 16 carbon atoms, preferably 1 to 10 carbon atoms, such as acetamido and p-chlorobenzoylamido groups. The alkylamino group includes one having 1 to 16 carbon atoms, preferably 1 to 10 carbon atoms, such as N,N-dimethylamino and N-(2-hydroxyethyl)amino groups. The arylamino group include one having 6 to 24 carbon atoms, such as anilino and N-methylanilino groups. The heterocyclic amino group includes a 5- or 6-membered saturated or unsaturated heterocyclic amino group containing 1 to 5 carbon atoms and one or more hetero atoms selected from an oxygen atom, a nitrogen atom and a sulfur atom (the two or more hetero atoms may be the same or different), such as 2-oxazolylamino, 2-tetrahydropyranylamino, and 4-pyridylamino groups. The ureido group include one having 1 to 16 carbon atoms, preferably 1 to 10 carbon atoms, such as ureido, methylureido, N,N-diethylureido, and 2-methanesulfonamidoethylureido groups. The sulfamoylamino group includes one having 0 to 16 carbon atoms, preferably up to 10 carbon atoms, such as methylsulfamoylamino and 2-methoxyethylsulfamoylamino groups. The alkoxycarbonylamino group includes one having 2 to 16 carbon atoms, preferably 2 to 10 carbon atoms, such as methoxycarbonylamino group. The aryloxycarbonylamino group includes one having 7 to 24 carbon atoms, such as phenoxycarbonylamino and 2,6-dimethoxyphenoxycarbonylamino group. The sulfonamido group includes one having 1 to 16 carbon atoms, preferably 1 to 10 carbon atoms, such as methanesulfonamido and p-toluenesulfonamido groups. The imido group includes one having 4 to 16 carbon atoms, such as N-succinimido and N-phthalimido groups. The oxamoylamino group includes one having 2 to 16 carbon atoms, preferably 2 to 10 carbon atoms, such as N-ethyloxamoylamino group. The heterocyclic group which is bonded at the nitrogen atom of its ring include a 5- or 6-membered heterocyclic ring containing a nitrogen atom and at least one of a carbon atoms, an oxygen atom and a sulfur atom, such as pyrrolidino, morpholino and imidazolino groups. The alkylthio group includes one having 1 to 16 carbon atoms, preferably 1 to 10 carbon atoms, such as methylthio and 2-phenoxyethylthio groups. The arylthio group includes one having 6 to 24 carbon atoms, such as phenylthio and 2-carboxyphenylthio groups. The heterocyclic thio group includes a 5- or 6-membered saturated or unsaturated heterocyclic thio group containing 1 to 5 carbon atoms and one or more hetero atoms selected from an oxygen atom, a nitrogen atom and a sulfur atom (the two or more hetero atoms may be the same or different), such as 2-benzothiazolylthio and 2-pyridylthio groups. The sulfamoyl group includes one having 0 to 16 carbon atoms, preferably up to 10 carbon atoms, such as sulfamoyl, methylsulfamoyl, and phenylsulfamoyl groups. The alkoxysulfonyl group includes one having 1 to 16 carbon atoms, preferably 1 to 10 carbon atoms, such as a methoxysulfonyl group. The aryloxysulfonyl group includes one having 6 to 24 carbon atoms, preferably 6 to 12 carbon atoms, such as a phenoxysulfonyl group. The sulfonyl group includes one having 1 to 16 carbon atoms, preferably 1 to 10 carbon atoms, such as methanesulfonyl and benzenesulfonyl groups. The sulfinyl group includes one having 1 to 16 carbon atoms, preferably 1 to 10 carbon atoms, such as methanesulfinyl and benzenesulfinyl groups. The acylsulfamoyl group includes one having 1 to 18 carbon atoms, preferably 1 to 16 carbon atoms, such as N-acetylsulfamoyl and N-benzoylsulfamoyl groups.

The divalent aromatic group as Ar is preferably a monocyclic arylene group, still preferably a phenylene group which may be substituted with the above-enumerated substituents, and particularly preferably an unsubstituted phenylene group. When Ar is a substituted phenylene group, preferred substituents are an alkyl group, an alkoxy group, a hydroxyl group, an amino group, an alkylamino group, an acylamino group, a sulfonamido group, a ureido group, a halogen atom, a carboxyl group, and a sulfo group. The total carbon atom number of the substituents is preferably 1 to 12, still preferably 1 to 8.

In formula (2), $R_{22}$ and $R_{23}$ each represents a divalent aliphatic or aromatic group.

The divalent aliphatic group is a substituted or unsubstituted and straight-chain, branched or cyclic alkylene, alkenylene or alkynylene group, and the divalent aromatic group is a monocyclic or bicyclic arylene group.

$R_{22}$ or $R_{23}$ preferably represents an alkylene or arylene group. Still preferably $R_{22}$ is a phenylene group, and $R_{23}$ is an alkylene group.

The aliphatic or aromatic group as $R_{22}$ or $R_{23}$ may have a substituent(s) selected from those described as the substituents Ar may have. Preferred substituents on $R_{22}$ or $R_{23}$ include a halogen atom, an alkyl group, an aryl group, a carbamoyl group, an alkoxycarbonyl group, an aryloxycarbonyl group, an acyl group, a cyano group, an alkoxy group, an aryloxy group, a carbamoyloxy group, an acylamino group, a ureido group, a sulfamoylamino group, an alkoxycarbonylamino group, a sulfonamido group, a sulfamoyl group, and a sulfonyl group. An alkyl group, an aryl group, a carbamoyl group, an alkoxy group, an acylamino group, a ureido group, a sulfonamido group, and a sulfamoyl group are still preferred substituents.

In formula (2), the divalent linking group as represented by $L_{21}$ or $L_{22}$ includes —O—, —S—, —N($R_{N2}$)— (wherein $R_{N2}$ represents a hydrogen atom, an alkyl group or an aryl group), —CO—, —SO$_2$—, and groups made up of a combination of these linking atoms or groups. Examples of linking groups made up of a combination are —CON($R_{N2}$)—, —SO$_2$N($R_{N2}$)—, —COO—, —N($R_{N2}$)CON($R_{N2}$)—, —SO$_2$N($R_{N2}$)CO—, —SO$_2$N($R_{N2}$)CON($R_{N2}$)—, —N($R_{N2}$)COCON($R_{N2}$)—, and —N($R_{N2}$)SO$_2$N($R_{N2}$)—. The plurality of $R_{N2}$'s may be the same or different.

$L_{21}$ is preferably —SO$_2$NH—, —NHCONH—, —O—, —S— or —N($R_{N2}$)—, still preferably —SO$_2$NH— or —NHCONH—.

$L_{22}$ is preferably —CON($R_{N2}$)—, —SO$_2$NH—, —NHCONH—, —N($R_{N2}$)CONH— or —COO—. When $L_{22}$ is —CON($R_{N2}$)— or —N($R_{N2}$)CONH—, $R_{N2}$ may represent —$R_{23}$—X in formula (2) as a substituted alkyl group.

In formula (2), $X_{21}$ represents an alkylthio group, an arylthio group, a heterocyclic thio group, a quaternary ammonium group, a nitrogen-containing heterocyclic group containing a quaternarized nitrogen atom, an alkoxy group containing an ethyleneoxy or propyleneoxy unit, or a saturated heterocyclic group containing a sulfide or disulfide linkage.

The alkylthio group as $X_{21}$ is a substituted or unsubstituted and straight-chain, branched or cyclic alkylthio group having 1 to 18 carbon atoms in total. The substituents on the alkylthio group preferably include an aryl group, an alkoxy group (inclusive of an alkoxy group containing an ethyleneoxy or propyleneoxy unit), a carboxyl group, a carbonyloxy group, an oxycarbonyl group, an acylamino group, a quaternary ammonium group, an alkylthio group, a heterocyclic group, a sulfonamido group, and a ureido group.

Specific examples of the alkylthio group are shown below.

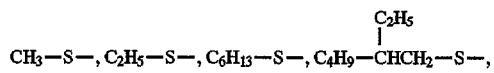

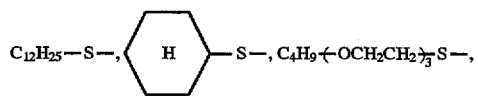

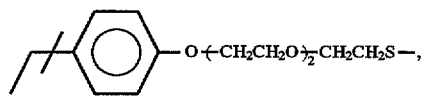

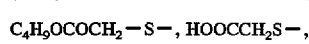

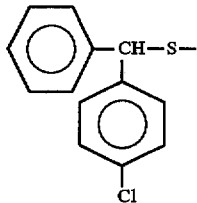

When $X_{21}$ represents an alkylthio group, $m_{23}$ is 1.

The arylthio group as $X_{21}$ includes a substituted or unsubstituted arylthio group having 6 to 18 carbon atoms in total. The substituents on the arylthio group include those described for Ar. The arylthio group is preferably a substituted or unsubstituted phenylthio group, e.g., phenylthio, 4-t-butylphenylthio, 4-dodecylphenylthio.

When $X_{21}$ represents an arylthio group, $m_{23}$ is 1.

The heterocyclic thio group as $X_{21}$ is a substituted or unsubstituted 5- or 6-membered monocyclic or condensed heterocyclic thio ring having 1 to 18 carbon atoms in total and containing one or more hetero atoms selected from an oxygen atom, a nitrogen atom and a sulfur atom, e.g., benzothiazolylthio, 1-phenyl-5-tetrazolylthio, 2-mercaptothiadiazolyl-4-thio, pyridyl-2-thio.

When $X_{21}$ represents a heterocyclic thio group, $m_{23}$ is 1.

The quaternary ammonium group as $X_{21}$ means a quaternary ammonium cation and its counter anion, which are formed by bonding a tertiary amino group to $R_{23}$. The tertiary amino group is an aliphatic or aromatic tertiary amino group, which may have a cyclic structure. The total carbon atom number of the tertiary amino group is preferably 3 to 24. The counter anion includes a chloride anion, a bromide anion, an iodide anion, a sulfonate anion, and a carbonate anion. When the compound of formula (2) has a sulfo group or a carboxyl group, the cation may form an intramolecular salt.

When $X_{21}$ represents a quaternary ammonium group, $m_{23}$ is 1.

When $X_{21}$ represents a nitrogen-containing heterocyclic group containing a quaternarized nitrogen atom, there are included a case in which a nitrogen-containing heterocyclic group is quaternarized on being bonded at the nitrogen atom thereof to $R_{23}$ and a case in which a previously quaternarized nitrogen-containing heterocyclic ring is bonded to $L_{22}$ or $L_{21}$ with $R_{23}$ taking no part in. In the former case, $m_{23}$ is 1; and in the latter case, $m_{23}$ is 0.

Specific examples of the nitrogen-containing heterocyclic group containing a quaternarized nitrogen atom are pyridinium, quinolinium, isoquinolinium, phenanthrenium, triazolinium, imidazolinium, and benzothiazolinium groups.

These groups may have a substituent(s). Preferred substituents include an alkyl group, an aryl group, an alkoxy group, an alkylcarbamoyl group, an amino group, an ammonium group, and a heterocyclic group.

The alkoxy group containing an ethyleneoxy or propyleneoxy unit as $X_{21}$ includes $R_{24}$—O—$(CH_2CH_2O)_p$—, $R_{24}$—O—$[CH_2CH(CH_3)O]_p$—, and $R_{24}$—O—$[CH_2CH(OH)CH_2O]_p$—, wherein p is an integer of 1 or greater, and $R_{24}$ represents an aliphatic or aromatic group. $R_{24}$ is preferably an alkyl group having 1 to 20 carbon atoms or an aryl group having 6 to 20 carbon atoms.

Specific examples of the above alkoxy group are $CH_3O$—$(CH_2CH_2O)_3$—, $C_6H_{13}O(CH_2CH_2O)_2$—, $C_4H_9O$—$(CH_2CH_2CH_2O)_2$—, $C_8H_7OCH_2CH(OH)CH_2O$—, $C_{12}H_{25}O$—$[CH_2CH_2(CH_3)O]_2$—, and $C_2H_5O$—$(CH_2CH_2O)_6$—.

When $X_{21}$ represents an alkoxy group containing an ethyleneoxy or propyleneoxy group, $m_{23}$ is 1.

The saturated heterocyclic group containing a sulfide or disulfide linkage as $X_{21}$ is a 5- or 6-membered saturated heterocyclic ring containing a —S— bond or a —S—S— bond. Preferred examples of such group are shown below.

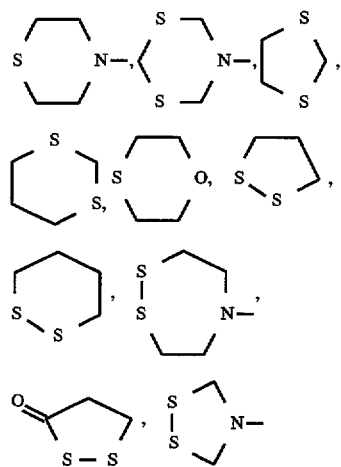

When $X_{21}$ represents a saturated heterocyclic group containing a disulfide linkage, $m_{23}$ is 1.

Of the compounds represented by formula (2) preferred are those represented by formula (21):

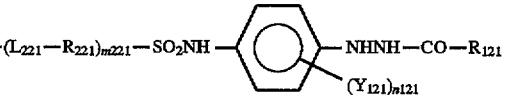

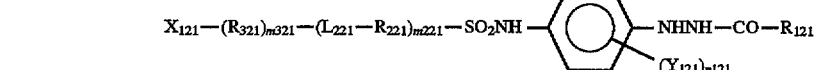

wherein $X_{121}$, $R_{121}$, $R_{221}$, $R_{321}$, $L_{221}$, $m_{221}$, and $m_{321}$ have the same meaning as $X_{21}$, $R_{21}$, $R_{22}$, $R_{23}$, $L_{22}$, $m_{22}$, and $m_{23}$ of formula (2), respectively; $Y_{121}$ represents a substituent; and $n_{121}$ represents an integer of 0 to 4.

The substituent as $Y_{121}$ is selected from the substituents Ar of formula (2) can have, preferably a substituent selected from the substituents preferred for Ar. $n_{121}$ preferably represents 0 or 1, still preferably 0.

Of the compounds represented by formula (21) wherein $X_{121}$ represents an alkylthio group, more preferred are those represented by formula (22):

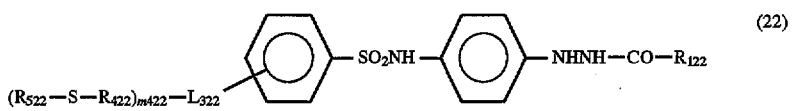

wherein $R_{122}$ has the same meaning as $R_{121}$ in formula (21); $R_{422}$ represents an alkylene group; $L_{322}$ represents a group linking to the benzene ring, selected from an acylamino group, a carbamoyl group, a ureido group, an oxycarbonyl group, and a sulfonamido group; when $L_{322}$ is an acylamino, oxycarbonyl or sulfonamido group, $m_{422}$ represents 1; when $L_{322}$ is a carbamoyl or ureido group, $m_{422}$ represents 1 or 2; when $m_{422}$ is 1, $R_{522}$ represents an unsubstituted alkyl group having 7 or more carbon atoms, a substituted alkyl group having 1 to 18 carbon atoms in total or a cycloalkyl group having 3 or more carbon atoms in total; and when $m_{422}$ is 2, $R_{522}$ represents a substituted or unsubstituted alkyl group having 1 to 18 carbon atoms in total or a cycloalkyl group having 3 or more carbon atoms in total.

Specific examples of the hydrazide compounds of formula (2) are shown below.

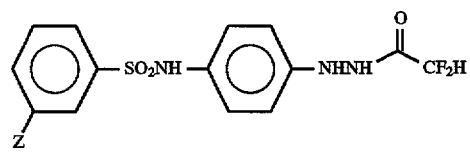

Z=

2-1     $C_7H_{15}-S-C_2H_4-NHCONH-$

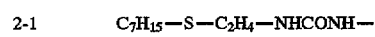

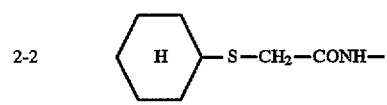

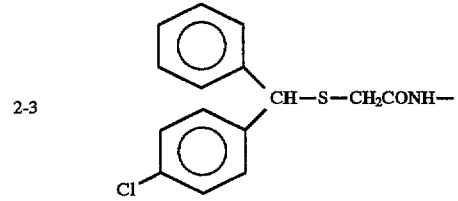

2-4     $C_4H_9-\underset{\underset{C_2H_5}{|}}{CH}-CH_2-S-C_2H_4-NHCONH-$ 2-5     $(C_3H_7-S-C_2H_4)_2N-CONH-$ 2-6     $(CH_3S-C_3H_6)_2N-CO-$ 2-7     $C_4H_9+OCH_2CH)_2S-CH_2CONH-$
                         |
                         $CH_3$

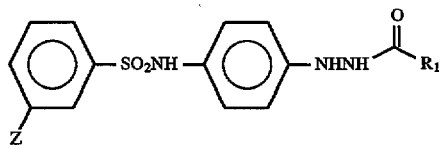

Z=                                              $R_1=$

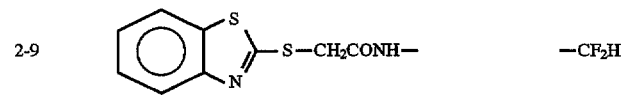

| | | |
|---|---|---|
| 2-10 | 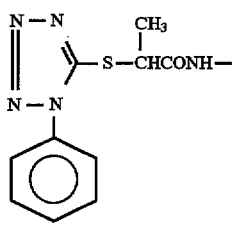 | —CF$_2$H |
| 2-11 | C$_8$H$_{17}$—S—C$_2$H$_5$—O—CO— | —CF$_2$H |
| 2-12 | C$_7$H$_{15}$—S—C$_2$H$_4$—NHCO— | —CF$_2$H |
| 2-13 | 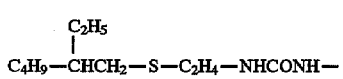 | —CFH$_2$ |
| 2-14 | 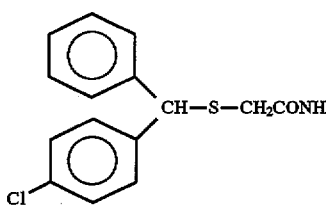 | —CFH$_2$ |
| 2-15 | 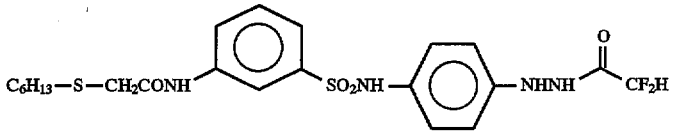 | |
| 2-16 | 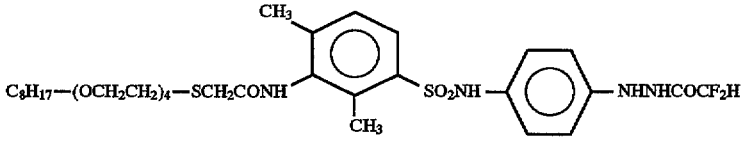 | |
| 2-17 | 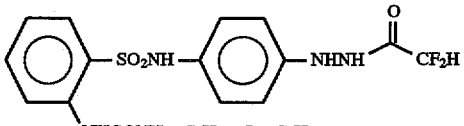 | |
| 2-18 | 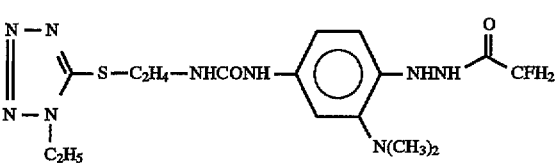 | |
| 2-19 | 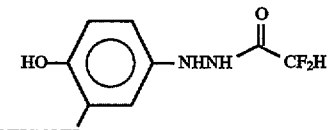 | |
| 2-20 | 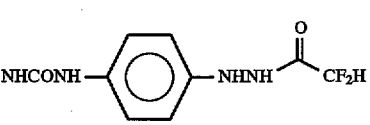 | |

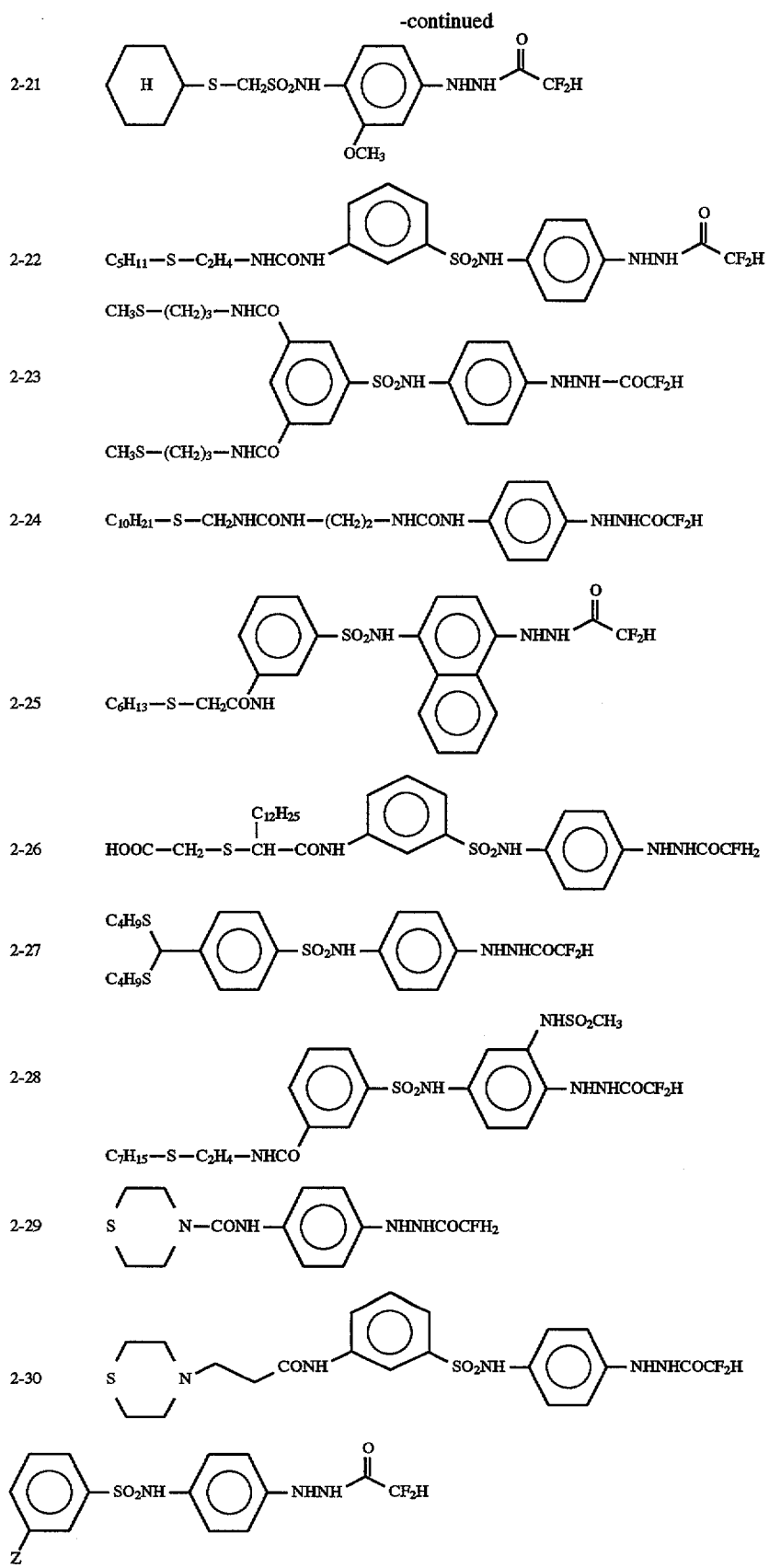

2-31 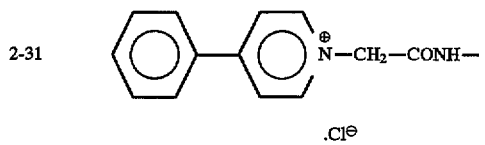
2-32 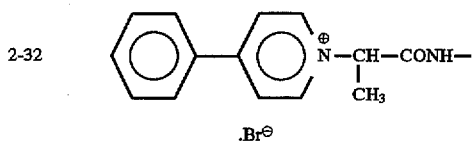
2-33 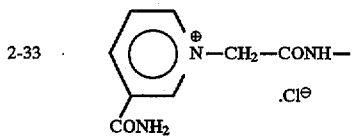
2-34 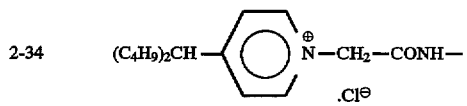
2-35 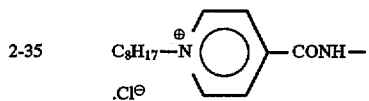
2-36 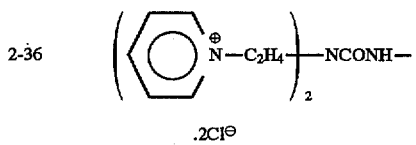
2-37 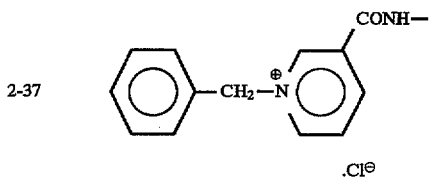
2-38 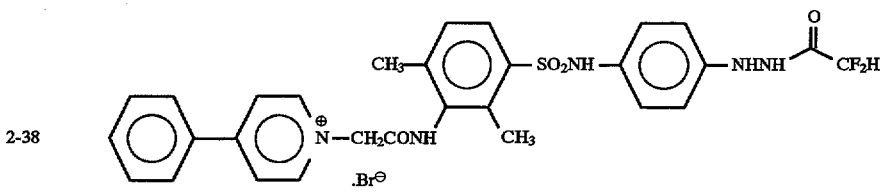
2-39 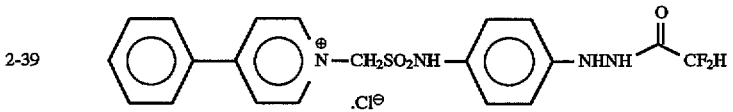
2-40 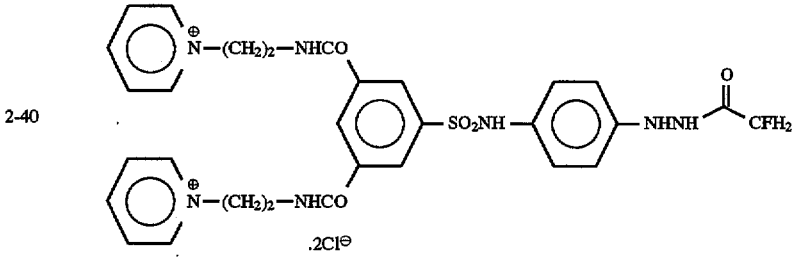

-continued
2-41 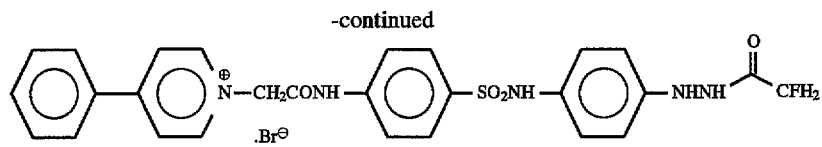
2-42 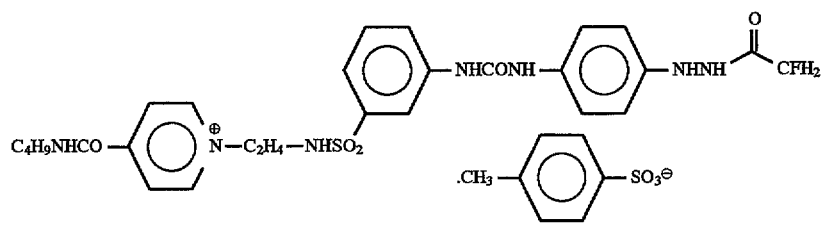
2-43 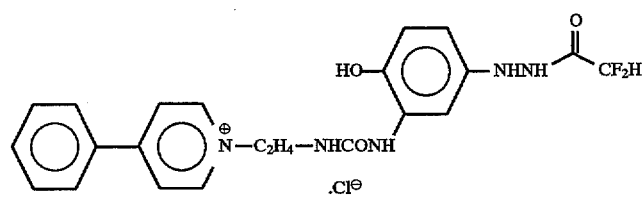
2-44 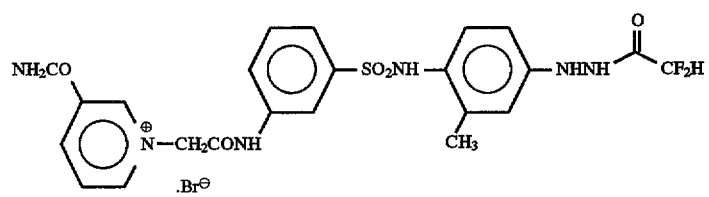
2-45 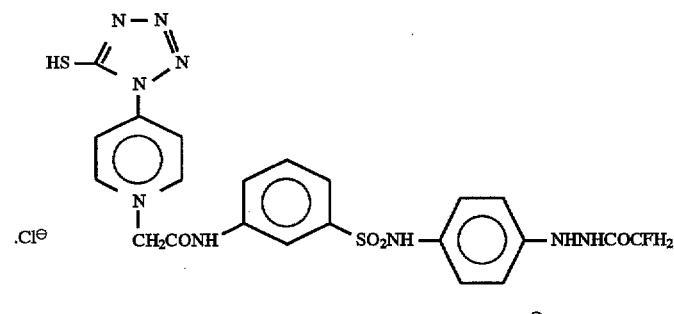
Z=
2-46 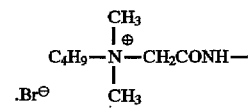
2-47 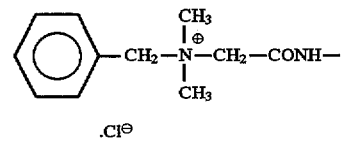
2-48 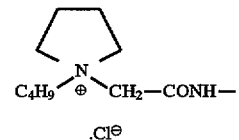

2-49  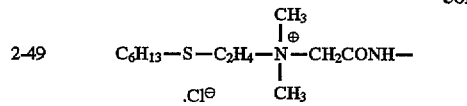

2-50  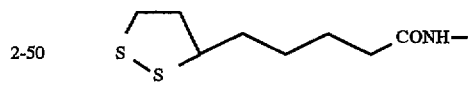

2-51  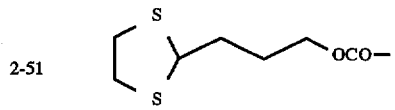

2-52  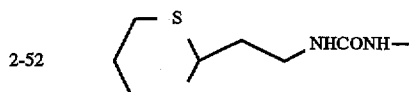

2-53  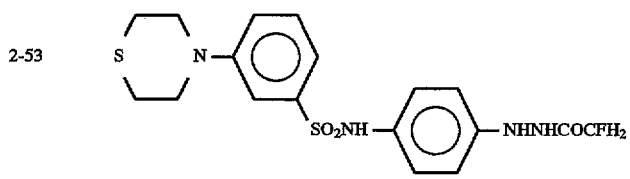

2-54  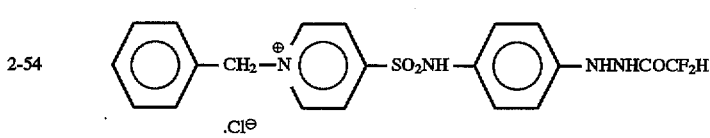

2-55  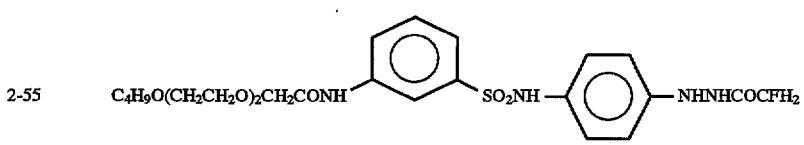

The compounds of formula (2) can easily be synthesized by condensing a hydrazine derivative and difluoroacetic acid or monofluoroacetic acid using an appropriate condensing agent or by reacting a hydrazine derivative with an anhydride or halide of the acid according to reaction scheme 2 shown below.

Reaction scheme 2:

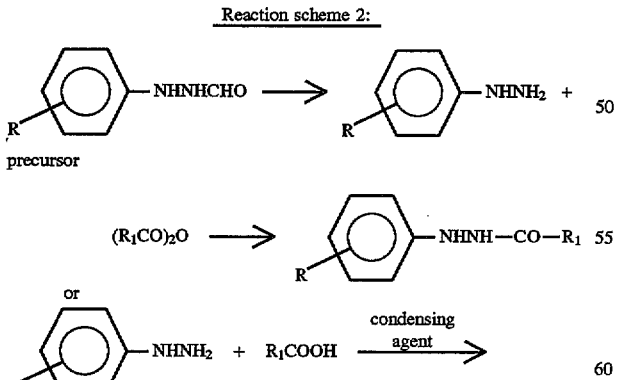

-continued
Reaction scheme 2:

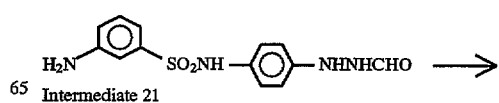

wherein $R_1$: $CF_2H$ or $CFH_2$; R: substituent.

Condensing agents used for amidation, such as dicyclohexylcarbodiimide or trifluoromethanesulfonyl chloride, are effective. A formylhydrazine derivative can be used as a hydrazine derivative precursor.

SYNTHESIS EXAMPLE 5

Synthesis of Compound 2-1

Compound 2-1 was synthesized according to reaction scheme 3 shown below:

Reaction scheme 3:

$H_2N$—⬡—$SO_2NH$—⬡—NHNHCHO ⟶

Intermediate 21

Reaction scheme 3:

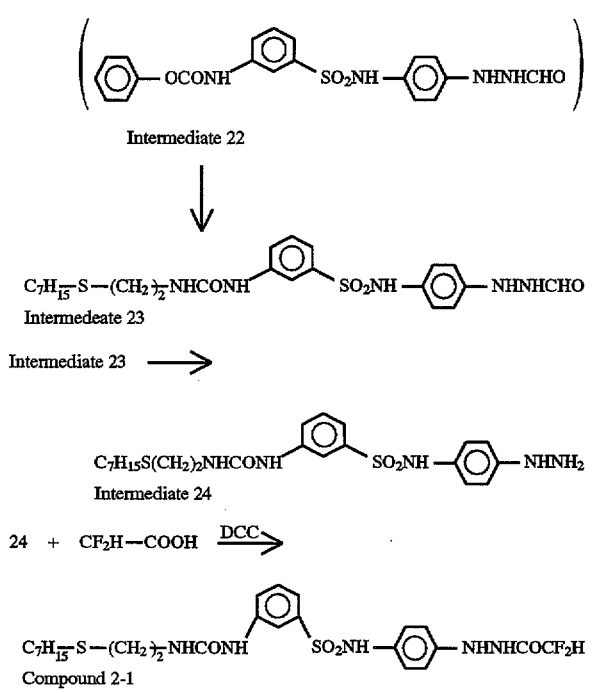

Synthesis of Intermediate 21:

N-p-Nitrophenyl-N'-formylhydrazine and m-nitrobenzenesulfonyl chloride were reacted, and the resulting N-m-nitrobenzenesulfonamidophenyl-N'-formylhydrazine was reduced with iron to prepare intermediate 21.

Synthesis of Intermediate 23:

To 500 ml of an acetonitrile/dimethylacetamide mixed solution containing 75.7 g of intermediate 21 and 22 ml of pyridine was added dropwise 30 ml of an acetonitrile solution containing 40.6 g of phenyl chloroformate under cooling with ice.

The mixture was stirred at −5° C. for 30 minutes, and 51.9 g of 2-heptylthioethylamine and 86 ml of triethylamine were added thereto, and the mixture was allowed to react at 40° C. for 3 hours. The product was extracted with ethyl acetate, washed with water and dried. The solvent was evaporated, ethyl acetate added to the residue, the precipitated crystals collected by filtration, to give 60 g of intermediate 23.

Synthesis of Intermediate 24:

In 200 ml of methanol were suspended 44.7 g of intermediate 23 and 22.2 g of 1,5-dinaphthalenesulfonic acid and allowed to react at 50° C. for 2 hours. After cooling, 500 ml of acetonitrile was added thereto slowly, and the precipitated crystals were collected by filtration and dried to give 53.6 g of intermediate 24.

Synthesis of Compound 2-1:

In DMF were dissolved 10.0 g of intermediate 24 and 1.21 ml of difluoroacetic acid, and 10 ml of a DMF solution of 3.97 g of dicyclohexylcarbodiimide was slowly added thereto dropwise at room temperature. After the dropwise addition, the reaction mixture was stirred for 2 hours and cooled, followed by filtration. The filtrate was extracted with ethyl acetate, and the extract was washed with water and evaporated under reduced pressure to remove the solvent. The residue was purified by column chromatography to give 2.3 g of compound 2-1 as amorphous crystals.

SYNTHESIS EXAMPLE 6

Synthesis of Compound 2-5

Compound 2-5 was synthesized in the same manner as for compound 2-1 except for replacing 2-heptylthioethylamine with di(2-propylthioethyl)amine.

SYNTHESIS EXAMPLE 7

Synthesis of Compound 2-3

Compound 2-3 was obtained in the same manner as for compound 2-1 except for replacing phenyl chloroformate with 4-chlorobenzhydrylthioacetyl chloride to once prepare an amide compound 3A (corresponding to intermediate 23).

Amide Compound 3A:

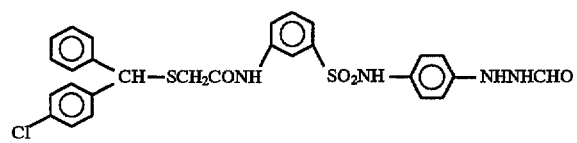

SYNTHESIS EXAMPLE 8

Synthesis of Compound 2-31

Intermediate 31A was prepared in the same manner as in the synthesis of compound 2-1 except for replacing phenyl chloroformate with chloroacetyl chloride.

Intermediate 31A:

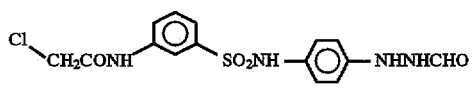

In 10 ml of dimethylacetamide were dissolved 4.18 g of intermediate 31A and 3.10 g of 4-phenylpyridine and allowed to react at 50° C. for 2 hours and then at 70° C. for 3 hours.

To the reaction mixture was added 50 ml of ethyl acetate, followed by stirring well, and the supernatant liquid was discarded. After repeating this operation, the ethyl acetate dispersion was filtered to obtain 3.1 g of compound 2-31.

SYNTHESIS EXAMPLE 9

Synthesis of Compound 2-47

Compound 2-47 was synthesized in the same manner as for compound 2-31 except for replacing 4-phenylpyridine with benzyldimethylamine.

The compounds represented by formula (3) will be explained below.

In formula (3), $R_{32}$ represents an aliphatic group, an aromatic group or a heterocyclic group. The bonding position of $R_2$—$SO_2NH$— is preferably para-position with respect to —NHNH—.

The aliphatic group as $R_{32}$ is a substituted or unsubstituted and straight-chain, branched or cyclic alkyl, alkenyl or alkynyl group, preferably an alkyl group. The aromatic group as $R_{32}$ is a monocyclic or bicyclic aryl group, such as a substituted or unsubstituted phenyl or naphthyl group. The heterocyclic group as $R_{32}$ is a saturated or unsaturated and substituted or unsubstituted 3- to 10-membered heterocyclic ring containing at least one hetero atom selected from nitrogen, oxygen and sulfur atoms, which may be monocyclic or be condensed with other aromatic or heterocyclic rings. The heterocyclic ring is preferably 5- or 6-membered aromatic heterocyclic ring, such as a pyridine ring, an imidazolyl group, a quinolinyl group, a benzimidazolyl group, a pyrimidyl group, a pyrazolyl group, an isoquinolinyl group, a thiazolyl group, or a benzothiazolyl group.

The substituent $R_{32}$ can have includes a halogen atom or a group which is bonded to a ring or a main chain via a carbon atom, an oxygen atom, a nitrogen atom or a sulfur atom possessed by itself. Groups which are bonded at their carbon atom include an alkyl group, an alkenyl group, an alkynyl group, an aryl group, a carbamoyl group, an alkoxycarbonyl group, an aryloxycarbonyl group, an acyl group, an acylcarbamoyl group, a sulfonylcarbamoyl group, a carboxyl group, a cyano group, and a heterocyclic group. Groups which are bonded at their oxygen atom include a hydroxyl group, an alkoxy group, an aryloxy group, a heterocyclic oxy group, an acyloxy group, a carbamoyloxy group, and a sulfonyloxy group. Groups which are bonded at their nitrogen atom include an acylamino group, an amino group, an alkylamino group, an arylamino group, a heterocyclic amino group, a ureido group, a sulfamoylamino group, an alkoxycarbonylamino group, an aryloxycarbonylamino group, a sulfonamido group, an imido group, and an oxamoylamino group, and a heterocyclic group. Groups which are bonded at their sulfur atom include an alkylthio group, an arylthio group, a heterocyclic thio group, a sulfamoyl group, an acylsulfamoyl group, an alkoxysulfonyl group, an aryloxysulfonyl group, a sulfonyl group, a sulfo group, and a sulfinyl group. These group may further be substituted with these substituents.

Going into details of the above-described substituents, the halogen atom includes a fluorine atom, a chlorine atom, and a bromine atom. The alkyl group includes a straight-chain, branched or cyclic alkyl group having 1 to 16 carbon atoms, preferably 1 to 10 carbon atoms, such as methyl, ethyl, isopropyl, t-butyl, benzyl, and cyclopentyl groups. The alkenyl group includes one containing 2 to 16 carbon atoms, such as vinyl, 1-propenyl, 1-hexenyl, and styryl groups. The alkynyl group includes one containing 2 to 16 carbon atoms, such as ethynyl, 1-butynyl, 1-dodecenyl, and phenylethynyl groups. The aryl group includes one having 6 to 24 carbon atoms, such as phenyl, naphthyl and p-methoxyphenyl groups. The carbamoyl group includes one having 1 to 18 carbon atoms, such as carbamoyl, N-ethylcarbamoyl, N-octylcarbamoyl, and N-phenylcarbamoyl groups. The alkoxycarbonyl group includes one having 2 to 18 carbon atoms, such as methoxycarbonyl and benzyloxycarbonyl groups. The aryloxycarbonyl group includes one having 7 to 18 carbon atoms, such as a phenoxycarbonyl group. The acyl group includes one having 1 to 18 carbon atoms, such as acetyl and benzoyl groups. The heterocyclic group which is bonded at the carbon atom of its ring includes a 5- or 6-membered saturated or unsaturated hetero ring containing 1 to 5 carbon atoms and one or more hetero atoms selected from an oxygen atom, a nitrogen atom and a sulfur atom (the two or more hetero atoms may be the same or different), such as 2-furyl, 2-thienyl, 2-pyridyl, and 2-imidazolyl groups. The acylcarbamoyl group includes one having 1 to 18 carbon atoms, such as N-acetylcarbamoyl and N-benzoylcarbamoyl groups. The sulfonylcarbamoyl group includes one having 1 to 18 carbon atoms, such as N-methanesulfonylcarbamoyl and N-benzenesulfonylcarbamoyl groups. The alkoxy group include one having 1 to 16 carbon atoms, preferably 1 to 10 carbon atoms, such as methoxy, 2-methoxyethoxy, and 2-methanesulfonylethoxy groups. The aryloxy group includes one having 6 to 24 carbon atoms, such as phenoxy, p-methoxyphenoxy, and m-(3-hydroxypropionamido) phenoxy groups. The heterocyclic oxy group includes a 5- or 6-membered saturated or unsaturated heterocyclic oxy group containing 1 to 5 carbon atoms and one or more hetero atoms selected from an oxygen atom, a nitrogen atom and a sulfur atom (the two or more hetero atoms may be the same or different), such as 1-phenyltetrazolyl-5-oxy, 2-tetrahydropyranyloxy and 2-pyridyloxy groups. The acyloxy group includes one having 1 to 16 carbon atoms, preferably 1 to 10 carbon atoms, such as acetoxy, benzoyloxy, and 4-hydroxybutanoyloxy groups. The carbamoyloxy group includes one having 1 to 16 carbon atoms, preferably 1 to 10 carbon atoms, such as N,N-dimethylcarbamoyloxy, N-hexylcarbamoyloxy, and N-phenylcarbamoyloxy groups. The sulfonyloxy group includes one having 1 to 16 carbon atoms, such as methanesulfonyloxy and benzenesulfonyloxy groups. The acylamino group includes one having 1 to 16 carbon atoms, preferably 1 to 10 carbon atoms, such as acetamido and p-chlorobenzoylamido groups. The alkylamino group includes one having 1 to 16 carbon atoms, preferably 1 to 10 carbon atoms, such as N,N-dimethylamino and N-(2-hydroxyethyl)amino groups. The arylamino group include one having 6 to 24 carbon atoms, such as anilino and N-methylanilino groups. The heterocyclic amino group includes a 5- or 6-membered saturated or unsaturated heterocyclic amino group containing 1 to 5 carbon atoms and one or more hetero atoms selected from an oxygen atom, a nitrogen atom and a sulfur atom (the two or more hetero atoms may be the same or different), such as 2-oxazolylamino, 2-tetrahydropyranylamino, and 4-pyridylamino groups. The ureido group include one having 1 to 16 carbon atoms, preferably 1 to 10 carbon atoms, such as ureido, methylureido, N,N-diethylureido, and 2-methanesulfonamidoethylureido groups. The sulfamoylamino group includes one having 0 to 16 carbon atoms, preferably up to 10 carbon atoms, such as methylsulfamoylamino and 2-methoxyethylsulfamoylamino groups. The alkoxycarbonylamino group includes one having 2 to 16 carbon atoms, preferably 2 to 10 carbon atoms, such as methoxycarbonylamino group. The aryloxycarbonylamino group includes one having 7 to 24 carbon atoms, such as phenoxycarbonylamino and 2,6-dimethoxyphenoxycarbonylamino group. The sulfonamido group includes one having 1 to 16 carbon atoms, preferably 1 to 10 carbon atoms, such as methanesulfonamido and p-toluenesulfonamido groups. The imido group includes one having 4 to 16 carbon atoms, such as N-succinimido and N-phthalimido groups. The oxamoylamino group includes one having 2 to 16 carbon atoms, preferably 2 to 10 carbon atoms, such as N-ethyloxamoylamino group. The heterocyclic group which is bonded at the nitrogen atom of its ring include a 5- or 6-membered heterocyclic ring containing a nitrogen atom and at least one of a carbon atoms, an oxygen atom and a sulfur atom, such as pyrrolidino, morpholino and imidazolino groups. The alkylthio group includes one having 1 to 16 carbon atoms, preferably 1 to 10 carbon atoms, such as methylthio and 2-phenoxyethylthio groups. The arylthio group includes one having 6 to 24 carbon atoms, such as phenylthio and 2-carboxyphenylthio groups. The heterocyclic thio group includes a 5- or 6-membered saturated or unsaturated heterocyclic thio group containing 1 to 5 carbon atoms and one or more hetero atoms selected from an oxygen atom, a nitrogen atom and a sulfur atom (the two or more hetero atoms may be the same or different), such as 2-benzothiazolylthio and 2-pyridylthio groups. The sulfamoyl group includes one having 0 to 16 carbon atoms, preferably up to 10 carbon atoms, such as sulfamoyl, methylsulfamoyl, and phenylsulfamoyl groups. The alkoxysulfonyl group includes one having 1 to 16 carbon atoms, preferably 1 to 10 carbon atoms, such as a methoxysulfonyl group. The aryloxysulfonyl group includes one having 6 to 24 carbon atoms, preferably 6 to 12 carbon atoms, such as a phenoxysulfonyl group. The sulfonyl group includes one having 1 to 16 carbon atoms, preferably 1 to 10 carbon atoms, such as methanesulfonyl and benzenesulfonyl groups. The sulfinyl group includes one having 1 to 16 carbon atoms, preferably 1 to 10 carbon atoms, such as methanesulfinyl and benzenesulfinyl groups. The acylsulfamoyl group includes one having 1 to 18 carbon atoms, preferably 1 to 16 carbon atoms, such as N-acetylsulfamoyl and N-benzoylsulfamoyl groups.

Of the above-described substituents preferred are a halogen atom, an alkyl group, an aryl group, a carbamoyl group, an alkoxycarbonyl group, an aryloxycarbonyl group, an acyl group, a cyano group, an alkoxy group, an aryloxy group, a carbamoyloxy group, an acylamino group, a ureido group, a sulfamoylamino group, an alkoxycarbonylamino group, a sulfonamido group, a sulfamoyl group, and a sulfonyl group. A halogen atom, an alkyl group, an aryl group, a carbamoyl group, an alkoxy group, an aryloxy group, an acylamino group, a ureido group, a sulfonamido group, and a sulfamoyl group are still preferred.

In formula (3), $R_{32}$ preferably represents a substituted phenyl group. While the substituents on a phenyl group as $R_{32}$ are selected from those described above, the phenyl group does not have an aralkylamino group as a substituent.

Preferred substituents on the phenyl group as $R_{32}$ are a halogen atom or an alkyl, alkoxy, acylamino, ureido, sulfonamide, carbamoyl or oxycarbonyl group having 1 to 21 carbon atoms, still preferably 8 to 16 carbon atoms.

It is particularly preferable that $R_{32}$ contains a nondiffusion group as used in a photographic coupler, i.e., a so-called ballast group, as a substituent. The terminology "ballast group" as used herein means such a group that prevents the compound of formula (3) added to a specific silver halide emulsion layer from easily diffusing to other layers or from being easily dissolved out into a developer at the time of development. From this viewpoint, the ballast group means a group having 8 or more, preferably 8 to 16, carbon atoms in total. Preferred ballast groups include an alkyl group, an aryl group, an alkoxy group, an aryloxy group, an oxycarbonyl group, a carbamoyl group, an acylamino group, a sulfonamido group, a carbonyloxy group, a ureido group, a sulfamoyl group, and a combination of these groups.

Accordingly, $R_{32}$ preferably represents a phenyl group substituted with a ballast group, the ballast group being preferably a substituted or unsubstituted alkyl, alkoxy, acylamino, ureido, sulfonamido, carbamoyl or oxycarbonyl group. The substituent on these ballast groups includes a halogen atom, an alkyl group, an aryl group, an alkoxy group, an aryloxy group, an oxycarbonyl group, a carbamoyl group, an acylamino group, a sulfonamido group, a carbonyloxy group, a ureido group, a sulfamoyl group, a carboxyl group, a sulfo group, and a combination thereof.

Since the ballast group has 8 or more, preferably 8 to 16 carbon atoms, the ballast group-substituted phenyl group as $R_2$ preferably contains 14 or more, preferably 14 to 22 carbon atoms.

It is preferable that $R_{32}$ does not contain a group accelerating adsorption to silver halide, an alkylthio group, an arylthio group, a heterocyclic thio group, a quaternary ammonium group, a nitrogen-containing heterocyclic group containing a quaternarized nitrogen atom, an alkoxy group containing an ethyleneoxy or propyleneoxy unit, or a saturated heterocyclic group containing a sulfide or disulfide linkage.

In formula (3), $X_{31}$ represents a substituent capable of substituting the hydrogen atom of the benzene ring and includes the same substituents as those $R_{32}$ can have. $X_{31}$ preferably represents a carboxyl group, a sulfo group, an alkyl group, an amino group, an alkylamino group, a hydroxyl group, an alkoxy group, a halogen atom, an acylamino group, a sulfonamido group, and a ureido group. These substituents preferably have 1 to 12, particularly 1 to 8 carbon atoms, in total.

In formula (3), $m_{31}$ represents an integer of 0 to 4, preferably 0 or 1, still preferably 0.

Specific examples of the hydrazine compounds of formula (3) are shown below for illustrative purposes but not for limitation.

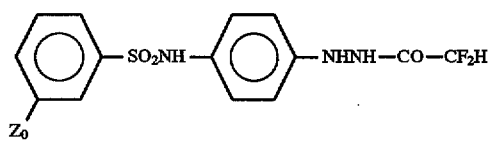

$Z_0 =$ 3-1  (n)$C_9H_{19}$—CONH—

3-2  $C_4H_9$—CHCONH—
            |
            $C_2H_5$ 3-3  ⟨structure⟩—O—CH$_2$CONH—

3-4  $C_7H_{15}$—NHCONH—

-continued
3-5 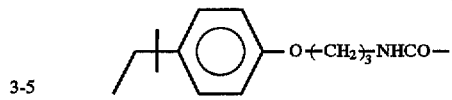
3-6 (n)C$_{12}$H$_{25}$—SO$_2$NHCO—
3-7 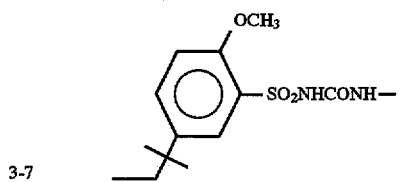
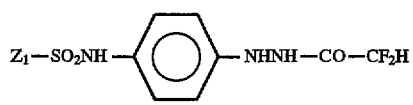
$Z_1 =$
3-8 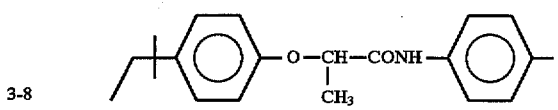
3-9 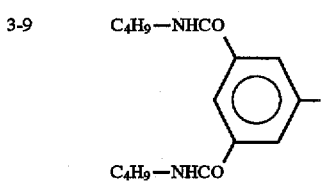
3-10 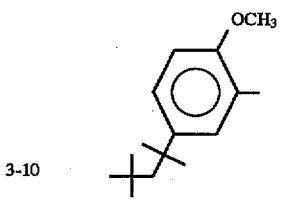
3-11 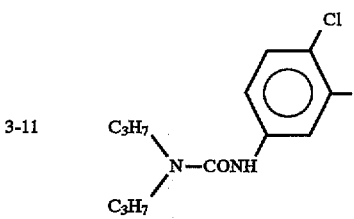
3-12 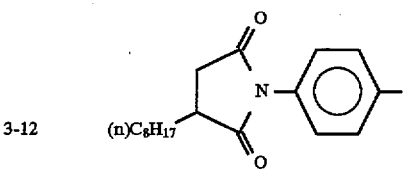
3-13 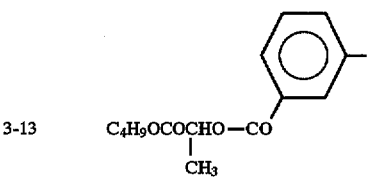

-continued
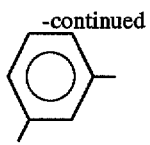
3-14  HOOC(CH₂)₂CONH—(CH₂)₃NHCO—
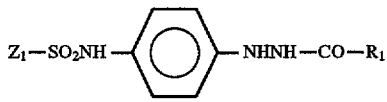
| | $Z_1=$ | $R_1=$ |
|---|---|---|
| 3-15 | (sec-C₄H₉)-C₆H₃(-)-O—(CH₂)₃—O—CH₂— | —CF₂H |
| 3-16 | (n)C₈H₁₇—CONH—C₆H₄— | —CFH₂ |
| 3-17 | (sec-C₄H₉)-C₆H₃(-)-O—CH₂CONH—C₆H₄— | " |
| 3-18 | C₄H₉—CH(C₂H₅)CH₂NHCONH—C₆H₃(Cl)— | " |
| 3-19 | (sec-C₄H₉)-C₆H₃(-)-O—(CH₂)₃—HNOC—C₆H₄— | " |
| 3-20 | (sec-C₄H₉)-C₆H₃(OC₂H₅)— | " |
| 3-21 | (n)C₁₂H₂₅— | " |
3-22  C₄H₉—CH(C₂H₅)CH₂—N(phthalimide with SO₂NH—C₆H₄—NHNH—COCF₂H)
3-23  (n)C₈H₁₇—HNOC—C₆H₃(HOOC)—SO₂NH—C₆H₃(OCH₃)—NHNH—CO—CF₂H 3-24 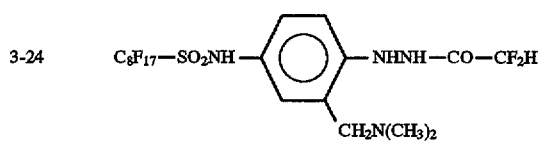
3-25 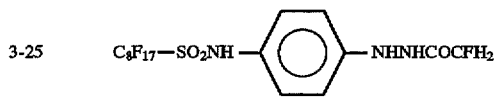
3-26 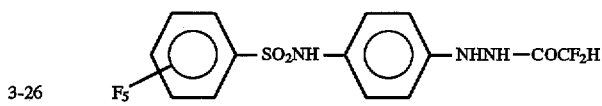
3-27 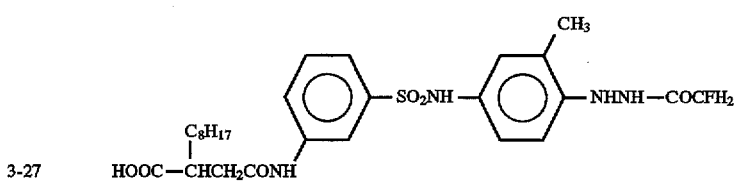
3-28 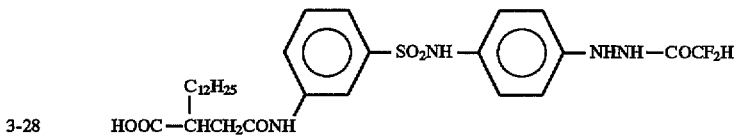
3-29 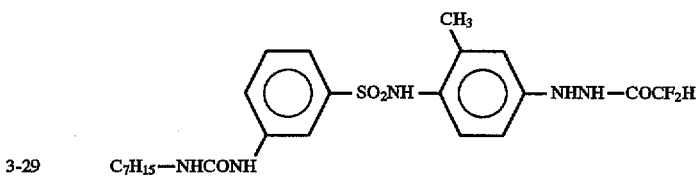
3-30 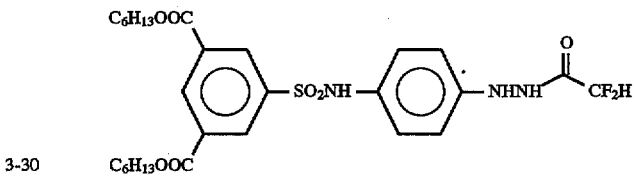
3-31 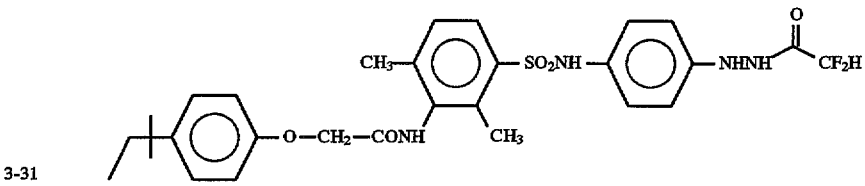
3-32 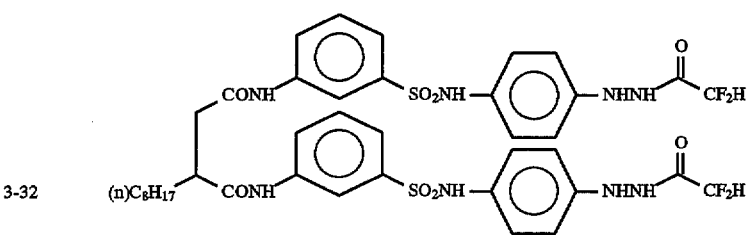

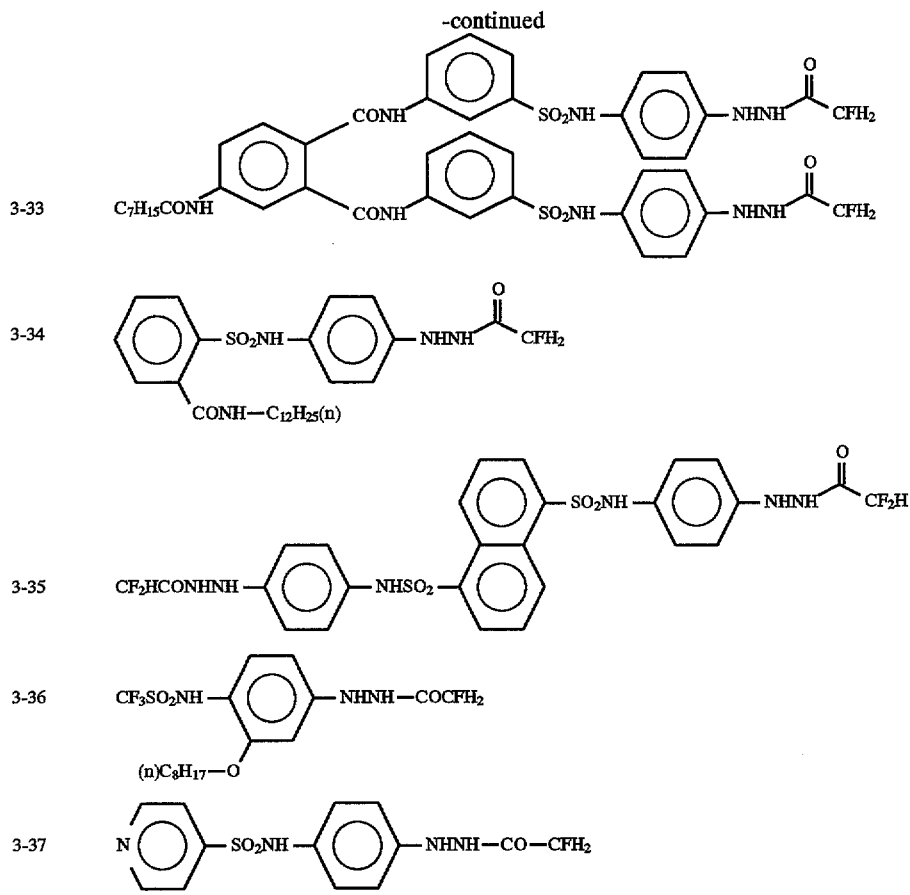

The compounds of formula (3) can easily be synthesized by condensing a hydrazine derivative and difluoroacetic acid or monofluoroacetic acid using an appropriate condensing agent or by reacting a hydrazine derivative with an anhydride or halide of the acid according to reaction scheme 4 shown below.

Reaction scheme 4:

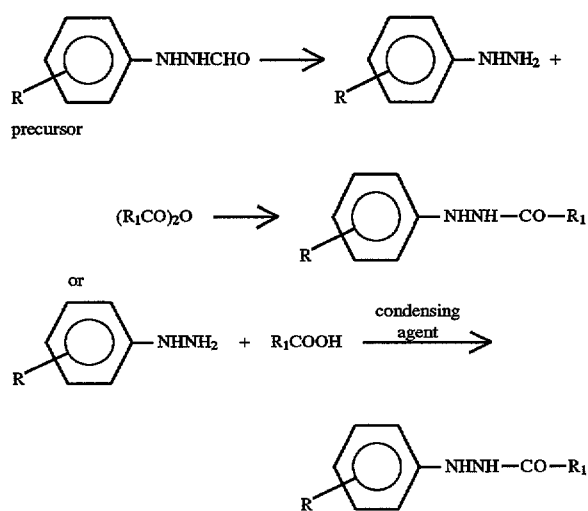

-continued
Reaction scheme 4:

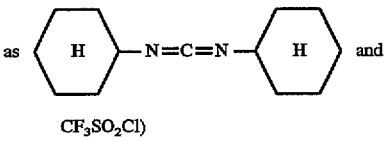

wherein $R_1$: $CF_2H$, $CFH_2$; R: substituent.

Condensing agents used for amidation, such as dicyclohexylcarbodiimide or trifluoromethanesulfonyl chloride, are effective. A formylhydrazine derivative can be used as a hydrazine derivative.

SYNTHESIS EXAMPLE 10

Synthesis of Compound 3-1

Reaction Scheme 5:

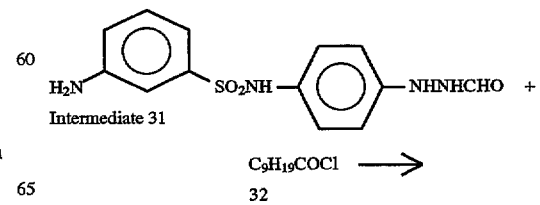

-continued
Reaction Scheme 5:

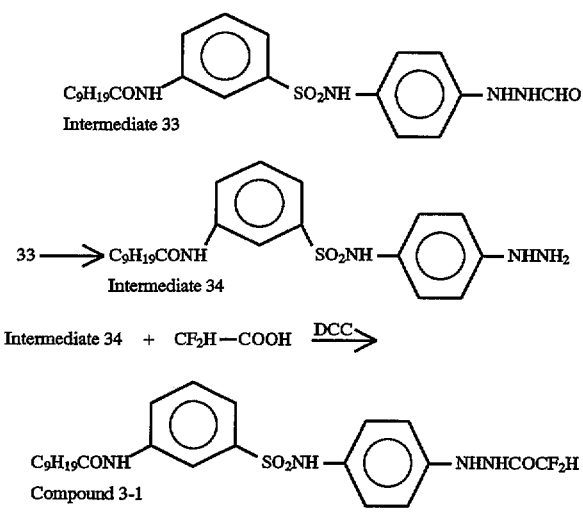

Synthesis of Intermediate 31:

N-p-Nitrophenyl-N'-formylhydrazine and m-nitrobenzenesulfonyl chloride were reacted, and the resulting N-m-nitrobenzenesulfonamidophenyl-N'-formylhydrazine was reduced with iron to prepare intermediate 31.

Synthesis of Intermediate 33:

To 100 ml of an acetonitrile/dimethylacetamide mixed solution containing 10.0 g of intermediate 31, 30 ml of an acetonitrile solution of 7.14 g of decanoic acid chloride was added dropwise under ice-cooling. The reaction mixture was worked up in a usual manner, and the reaction product was crystallized from ethyl acetate to give 12.31 g of intermediate 33.

Synthesis of Intermediate 34:

A methanol suspension (300 ml) containing 12.30 g of intermediate 33 and 4.54 g of 1,5-dinaphthalenesulfonic acid was heated in a nitrogen atmosphere and stirred at 50° C. for 3 hours. Ethyl acetate and a sodium hydrogencarbonate aqueous solution were added to the reaction mixture to extract the reaction product. After drying, the ethyl acetate layer was concentrated to give crude crystals as intermediate 34.

Synthesis of Compound 3-1:

The whole amount of the crude crystals (intermediate 34) and 2.6 g of difluoroacetic acid were dissolved in a mixture of dimethylimidazolidinone and acetonitrile to make a 300 ml solution. To the solution was added dropwise 50 ml of an acetonitrile solution of 5.5 g of dicyclohexylcarbodiimide (DCC) at room temperature. The reaction mixture was worked up in a usual manner, and the product was purified by column chromatography to give 3.4 g of compound 3-1 as amorphous crystals (yield from intermediate 33: 25%).

SYNTHESIS EXAMPLE 11

Synthesis of Compound 3-3

Compound 3-3 was synthesized in the same manner as for compound 3-1 except for replacing decanoic acid chloride with p-t-amylphenoxyacetyl chloride.

SYNTHESIS EXAMPLE 12

Synthesis of Compound 3-4

Intermediate 35 was prepared by reacting intermediate 31 in scheme 5 with phenyl chlorocarbonate and reacting the resulting phenylurethane compound with n-heptylamine.

Intermediate 35:

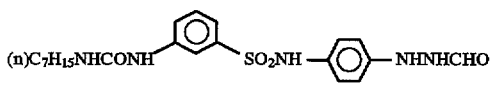

Compound 3-4 was prepared in the same manner as for compound 3-1 except for using intermediate 35 in place of intermediate 33 in scheme 5.

SYNTHESIS EXAMPLE 13

Synthesis of Compound 3-17

Compound 3-17 was synthesized in the same manner as for compound 3-3 except for using sodium monofluoroacetate in place of difluoroacetic acid.

SYNTHESIS EXAMPLE 14

Synthesis of Compound 3-28

Compound 3-28 was synthesized in the same manner as for compound 3-1 except for replacing decanoic acid chloride with 2-dodecylsuccinic anhydride.

The hydrazine compound of the invention is used as dissolved in an appropriate water-miscible organic solvent, such as an alcohol (e.g., methanol, ethanol, propanol, fluorinated alcohol), a ketone (e.g., acetone, methyl ethyl ketone), dimethylformamide, dimethyl sulfoxide, and methyl cellosolve.

The hydrazine compound can also be used in the form of an emulsified dispersion mechanically prepared by a well-known dispersion method using an oil (e.g., dibutyl phthalate, tricresyl phosphate, glycerol triacetate, diethyl phthalate) and an auxiliary solvent (e.g., ethyl acetate, cyclohexanone). It is also possible to use the hydrazine compound as a solid dispersion prepared by a well-known solid dispersion method in which a powdered compound is dispersed in water in a ball mill or a colloid mill, or by ultrasonic waves.

The hydrazine compound can be incorporated into a silver halide emulsion layer on the light-sensitive emulsion layer side or any other hydrophilic colloidal layers. It is preferably incorporated into a silver halide emulsion layer on the light-sensitive emulsion layer side or a hydrophilic colloidal layer adjacent thereto.

The hydrazine compound is preferably used in an amount ranging from $1.0 \times 10^{-6}$ to $1 \times 10^{-2}$ mol, still preferably from $1 \times 10^{-5}$ to $5 \times 10^{-3}$ mol, particularly preferably $5 \times 10^{-5}$ to $5 \times 10^{-3}$ mol, per mol of silver halide.

In addition to the hydrazine compounds of the invention, known hydrazine compounds may be used in combination. Usable known hydrazine compounds are described in Research Disclosure, No. 23516, p. 346 (November, 1983) and the references cited therein, and in U.S. Pat. Nos. 4,080,207, 4,269,929, 4,276,364, 4,278,748, 4,385,108, 4,459,347, 4,478,928, 4,560,638, 4,686,167, 4,912,016, 4,988,604, 4,994,365, 5,041,355, and 5,104,769, British Patent 2,011,391B, EP 217,310, EP 301,799, EP 356,898, JP-A-60-179734, JP-A-61-170733, JP-A-61-27044, JP-A-62-178246, JP-A-62-270948, JP-A-63-29751, JP-A-63-32538, JP-A-63-104047, JP-A-63-121838, JP-A-63-129337, JP-A-63-223744, JP-A-63-224244, JP-A-63-234245, JP-A-63-234246, JP-A-63-294552, JP-A-63-306438, JP-A-64-10233, JP-A-1-90439, JP-A-1-100530, JP-A-1-105941, JP-A-1-105943, JP-A-1-276128, JP-A-1-280747, JP-A-1-283548, JP-A-1-283549, JP-A-1-285940, JP-A-2-2541, JP-A-2-77057, JP-A-2-139538, JP-A-2-196234, JP-A-2-196235, JP-A-2-198440, JP-A-2-198441, JP-A-2-198442, JP-A-2-220042, JP-A-2-221953, JP-A-221954, JP-A-2-285342, JP-A-2-285343, JP-A-2-289843, JP-A-2-302750, JP-A-2-304550, JP-A-3-37642, JP-A-3-54549, JP-A-3-125134, JP-A-3-184039, JP-A-3-240036, JP-A-3-240037, JP-A-3-259240, JP-A-3-280038, JP-A-3-282536, JP-A-4-51143, JP-A-4-56842, JP-A-4-84134, JP-A-2-230233, JP-A-4-96053, JP-A-4-216544, JP-A-5-45761, JP-A-5-45762, JP-A-5-45763, JP-A-5-45764, JP-A-5-45765, and JP-A-6-289542.

The silver halide photographic material of the invention may contain known nucleation accelerators in at least one of the emulsion layers and other hydrophilic colloidal layers.

The following compounds represented by formulae (4), (5), (6), and (7) are preferably used as nucleation accelerator in the invention.

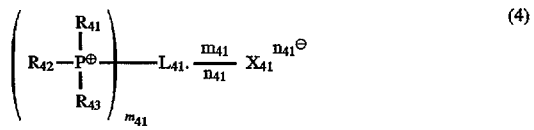

(4)

wherein $R_{41}$, $R_{42}$, and $R_{43}$ each represents a substituted or unsubstituted alkyl group, a substituted or unsubstituted cycloalkyl group, a substituted or unsubstituted aryl group, a substituted or unsubstituted alkenyl group, a substituted or unsubstituted cycloalkenyl group or a substituted or unsubstituted heterocyclic group; $m_{41}$ represents an integer of 1 to 4; $L_{41}$ represents an $m_{41}$-valent organic group bonded at its carbon atom to the phosphorus atom; $n_{41}$ represents an integer of 1 to 3; and $X_{41}$ represents an $n_{41}$-valent anion; $X_4$ may be bonded to $L_{41}$.

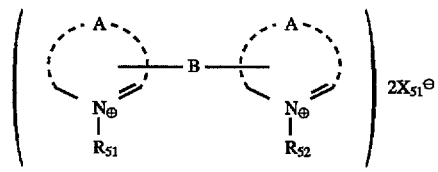

(5)

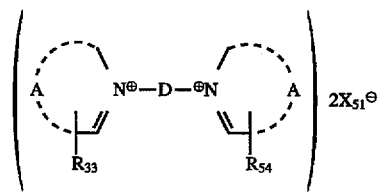

(6)

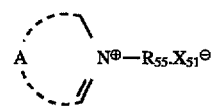

(7)

wherein A represents an organic group to complete the heterocyclic ring; B and D each represents a divalent group; $R_{51}$ and $R_{52}$ each represents an alkyl group or an aryl group; $R_{53}$ and $R_{54}$ each represents a hydrogen atom or a substituent; $R_{55}$ represents an alkyl group; and $X_{51}$ represents an anion, provided that $X_{51}$ is nil when the compound is an intramolecular salt.

For the particulars and specific examples of the compounds of formulae (4) to (7), refer to Japanese Patent Application No. 250136/94, in which compounds A201 to A262 are given as examples.

Most of the compounds of formula (4) are known and commercially available as reagent. They are generally synthesized by reacting a phosphinic acid derivative with an alkylating agent, such as an alkyl halide or a sulfonic ester, or exchanging the counter anion of a phosphonium salt in a conventional manner.

The compounds of formulae (5) to (7) are easily synthesized by well-known processes (e.g., the process described in Quart. Rev., Vol. 16, p. 163 (1962)).

The amount of the compounds of formulae (4) to (7) to be used, while not particularly limited, preferably ranges from $1 \times 10^{-5}$ to $2 \times 10^{-2}$ mol, particularly $2 \times 10^{-5}$ to $1 \times 10^{-2}$ mol, per mol of silver halide.

Of the nucleation accelerators of formulae (4) to (7), the compounds of formula (6) are particularly preferred.

The compounds of formulae (4) to (7) are incorporated into a photographic material by adding to a silver halide coating composition or a hydrophilic colloidal coating composition in the form of an aqueous solution when they are water soluble, or in the form of a solution in a water-miscible organic solvent, such as an alcohol (e.g., methanol, ethanol), an ester (e.g., ethyl acetate) or a ketone (e.g., acetone), when they are water insoluble.

The compounds of formulae (4) to (7) can also be used in the form of an emulsified dispersion mechanically prepared by a well-known dispersion method using an oil (e.g., dibutyl phthalate, tricresyl phosphate, glycerol triacetate, diethyl phthalate) and an auxiliary solvent (e.g., ethyl acetate, cyclohexanone) or in the form of a fine dispersion prepared by a well-known solid dispersion method.

The silver halide emulsion which can be used in the present invention may have any halogen composition, such as silver chloride, silver chlorobromide, silver iodochlorobromide, silver bromide, and silver iodobromide. For use in light-sensitive materials for scanners or cameras, silver halide grains having a silver chloride content of not less than 50 mol % are preferred. For use in light-sensitive materials for dot-to-dot work (contact work) in a lighted room, the silver chloride content is preferably not less than 95 mol %. Silver halide grains may have a cubic form, a tetradecahedral form, an octahedral form, an amorphous form or a tabular form, with cubic grains being preferred. The silver halide grains preferably have a mean grain size of 0.1 to 0.7 μm, still preferably 0.2 to 0.5 μm. The emulsion grains preferably have a narrow grain size distribution having a coefficient of variation of not more than 15%, still preferably not more than 10%, as expressed in terms of [(standard deviation of grain size)/(mean grain size)]×100.

The silver halide grains may be homogeneous throughout the individual grains or may comprise an outer layer and an inner layer differing in halogen composition.

The photographic emulsions used in the invention are prepared by conventional methods described, e.g., in P. Glafkides, Chimie et Physique Photographique, Paul Montel (1967), G. F. Duffin, Photographic Emulsion Chemistry, The Focal Press (1966), and V. L. Zelikman et al., Making and Coating Photographic Emulsion, The Focal Press (1964).

Methods of reacting a soluble silver salt and a soluble halogen salt include a single jet process, a double jet process, and a combination thereof. A so-called reverse mixing method, in which silver halide grains are formed in the presence of excess silver ions, may be employed. Further, a so-called controlled double jet process, a modification of a double jet process, in which a pAg value of a liquid phase when grains are formed is maintained constant, can also be used. Grain formation is preferably conducted in the presence of a silver halide solvent, such as ammonia, thioether, and a tetra-substituted thiourea compound, with a tetra-substituted thiourea compound being preferred. For the details of the tetra-substituted thiourea compound, JP-A-53-82408 and JP-A-55-77737 can be referred to. Tetramethylthiourea and 1,3-dimethyl-2-imidazolinethione are particularly preferred.

The controlled double jet process and the grain formation method using a silver halide solvent are effective means for preparing silver halide emulsions used in the invention. According to these means, a silver halide emulsion having a regular crystal form and a narrow grain size distribution can be prepared with ease.

In order to make the grain size uniform, it is preferable to let the grains grow rapidly within a range that does not exceed a critical saturation by using a method of varying the feeding rate of silver nitrate or an alkali halide in agreement with the rate of grain growth as described in British Patent 1,535,016, JP-B-48-36890, and JP-B-52-16364, or a method of changing the concentration of the aqueous solution as described in British Patent 4,242,445 and JP-A-55-158124.

In order to achieve high contrast and low fog, silver halide grains used in the invention can contain one or more metals selected from rhodium, rhenium, ruthenium, osmium, and iridium preferably in a total amount of $1\times10^{-9}$ to $1\times10^{-5}$ mol, particularly $1\times10^{-8}$ to $5\times10^{-6}$ mol, per mol of silver. Distribution of these metals in silver halide grains may be either uniform or non-uniform. Non-uniform distribution of the metals is described in JP-A-63-29603, JP-A-2-306236, JP-A-3-167545, JP-A-4-76534, and JP-A-6-110146.

Rhodium can be supplied in the form of a water-soluble rhodium compound, for example rhodium (III) halides and rhodium complex compounds having a halogen, amine or oxalato ligand, e.g., hexachlororhodates (III), hexabromorhodates (III), hexaminerhodates (III), and trioxalatorhodates (III). These rhodium compounds are used as dissolved in water or an appropriate solvent. A method frequently used for stabilizing a rhodium compound solution, i.e., addition of a hydrogen halide aqueous solution (e.g., hydrochloric acid, hydrobromic acid, hydrofluoric acid) or an alkali halide (e.g., KCl, NaCl, KBr, NaBr) can be taken advantage of. In place of using a water-soluble rhodium compound, rhodium can also be supplied by dissolving separately prepared silver halide grains previously doped with rhodium in the grain formation system.

The rhodium compound can be added at any stage during silver halide grain formation and before coating. It is particularly recommended to add it at the time of emulsion preparation so as to be integrated into silver halide grains.

Rhenium, ruthenium or osmium can be supplied in the form of a water-soluble complex salt as described in JP-A-63-2042, JP-A-1-285941, JP-A-2-20852, and JP-A-2-20855. Six-coordinate complexes represented by $[ML_6]^{-n}$, wherein M represents Ru, Re or Os; L represents a ligand; and n represents 0, 1, 2, 3 or 4, are particularly preferred. The counter anion, which is of no importance, includes an ammonium ion and an alkali metal ion. Preferred ligands include a halide ligand, a cyanide ligand, a cyano ligand, a nitrosyl ligand, and a thionitrosyl ligand. Specific but non-limiting examples of the Re, Ru or Os complexes useful in the invention are shown below.

| | | |
|---|---|---|
| $[ReCl_6]^{-3}$ | $[ReBr_6]^{-3}$ | $[ReCl_5(NO)]^{-2}$ |
| $[Re(NS)Br_5]^{-2}$ | $[Re(NO)(CN)_5]^{-2}$ | $[Re(O)_2(NO)_4]^{-3}$ |
| $[RuCl_6]^{-3}$ | $[RuCl_4(H_2O)_2]^{-2}$ | $[RuCl_5(NO)]^{-2}$ |
| $[RuBr_5(NS)]^{-2}$ | $[Ru(CN)_6]^{-4}$ | $[Ru(CO)_3Cl_3]^{-2}$ |
| $[Ru(CO)Cl_5]^{-2}$ | $[Ru(CO)Br_5]^{-2}$ | |

-continued

| | | |
|---|---|---|
| $[OsCl_6]^{-3}$ | $[OsCl_5(NO)]^{-2}$ | $[Os(NO)(CN)_5]^{-2}$ |
| $[Os(NS)Br_5]^{-2}$ | $[Os(CN)_6]^{-4}$ | $[Os(O)_2(CN)_4]^{-4}$ |

These metallic compounds can be added at any stage during silver halide grain formation and before coating. It is particularly recommended to add it at the time of emulsion preparation so as to be integrated into silver halide grains.

Integration of the metallic compound into silver halide grains by addition to a grain formation system can be carried out by a method in which a powdered metal complex is dissolved in water with or without NaCl or KCl and the aqueous solution is previously added to a water-soluble silver salt solution or a water-soluble halide solution to be used for grain formation, a method in which the above aqueous solution is added as a third solution simultaneously with the silver salt solution and the halide solution in the preparation of grains, or a method in which a requisite amount of a water-soluble metal complex salt is poured into the grain formation system. The method of previously adding an aqueous solution of a powdered metal complex (which may also contain NaCl or KCl) to a water-soluble halide solution is recommended.

In order to add the metal on the grain surface, an aqueous solution of a requisite amount of a metal complex may be poured into the reaction system immediately after grain formation, during or on completion of physical ripening, or during chemical sensitization.

Iridium can be supplied in the form of various iridium compounds, such as hexachloroiridates, hexammine iridium salts, trioxalatoiridates, and hexacyanoiridates. These iridium compounds are used as dissolved in water or an appropriate solvent. A method frequently used for stabilizing an iridium compound solution, i.e., addition of a hydrogen halide aqueous solution (e.g., hydrochloric acid, hydrobromic acid, hydrofluoric acid) or an alkali halide (e.g., KCl, NaCl, KBr, NaBr) can be taken advantage of. In place of using a water-soluble iridium compound, separately prepared silver halide grains previously doped with iridium can be dissolved in the grain formation system.

The silver halide grains may be doped with heavy metal salts other than the above-mentioned metals. In particular, doping with an Fe salt, e.g., $K_4[Fe(CN)_6]$, is advantageous.

The silver halide grains may further contain metal atoms, such as cobalt, nickel, palladium, platinum, gold, thallium, copper, and lead. These metals are preferably present in an amount of $1\times10^{-9}$ to $1\times10^{-4}$ mol per mol of silver halide. These metals can be added in the form of a single salt, a double salt or a complex salt at the time of grain preparation.

The silver halide emulsions used in the present invention are preferably subjected to chemical sensitization. Chemical sensitization of a silver halide emulsion is carried out by sulfur sensitization, selenium sensitization, tellurium sensitization, reduction sensitization, noble metal sensitization, or a combination thereof. Preferred combinations include sulfur-gold sensitization, sulfur-selenium-gold sensitization, and sulfur-tellurium-gold sensitization.

Sulfur sensitization is generally carried out by adding a sulfur sensitizer to an emulsion and stirring the emulsion at a high temperature of 40° C. or higher for a given period of time. Known sulfur sensitizers, such as a sulfur compound contained in gelatin and various sulfur compounds, e.g., thiosulfates, thioureas, thiazoles, and rhodanines, can be employed. Thiosulfates and thioureas are preferred. The amount of the sulfur sensitizer to be added ranges usually from $1\times10^{-7}$ to $1\times10^{-2}$ mol, preferably from $1\times10^{-5}$ to $1`10^{-3}$ mol of silver halide, though varying depending on the pH or temperature of the chemical ripening system or the size of silver halide grains.

Selenium sensitization is carried out by adding a known selenium compound as selenium sensitizer, i.e., a stable and/or non-stable selenium compound, to an emulsion and stirring the emulsion at a high temperature, preferably 40° C. or higher, for a given period of time. The stable selenium compounds described in JP-B-44-15748, JP-B-43-13489, JP-A-4-25832, and JP-A-4-109240 are useful. The compounds represented by formula (VIII) and (IX) of JP-A-4-324855, KSeCn, and NaSeCN are especially preferred.

Tellurium sensitizers to be used for tellurium sensitization are compounds capable of forming silver telluride which is assumed to become sensitization specs on the surface, or in the inside, of silver halide grains. The speed of silver telluride formation in silver halide emulsion grains can be demonstrated by the test method described in JP-A-5-313284. Useful tellurium sensitizers are described in U.S. Pat. Nos. 1,623,499, 3,320,069, and 3,772,031, British Patents 235,211, 1,121,496, 1,295,462, and 1,396,696, Canadian Patent 800,958, JP-A-4-204640, JP-A-4-271341, JP-A-4-333043, *J. Chem. Soc. Chem. Commun.*, Vol. 635 (1980), ibid, Vol. 1102 (1979), ibid, Vol. 645 (1979), *J. Chem. Soc. Perkin. Trans.*, Vol. 1, p. 2191 (1980), S. Patai (ed.), *The Chemistry of Organic Selenium and Tellurium Compounds*, Vol. 1 (1986), and ibid, Vol. 2 (1987). The compounds represented by formulae (II), (III) and (IV) of JP-A-5-313284 are particularly preferred.

While varying depending on the silver halide grains and the conditions of chemical sensitization, the amounts of the selenium sensitizers and tellurium sensitizers to be used are about $1 \times 10^{-8}$ to $1 \times 10^{-2}$ mol, preferably about $1 \times 10^{-7}$ to $1 \times 10^{-3}$ mol, per mol of silver halide.

While not limiting, the chemical sensitization is conducted at a pH of 5 to 8, a pAg of 6 to 11, preferably 7 to 10, and a temperature of 40° to 95° C., preferably 45° to 85° C.

Noble metal sensitizers to be used for nobel metal sensitization include gold, platinum, and palladium. Gold sensitization is preferred. Useful gold sensitizers include chloroauric acid, potassium chloroaurate, potassium tetrathiocyanatoaurate, and gold sulfide. The gold sensitizer is used in an amount of about $1 \times 10^{-7}$ to $1 \times 10^{-2}$ mol per mol of silver halide.

During silver halide grain formation or physical ripening, a cadmium salt, a sulfurous acid salt, a lead salt, or a thallium salt may be present in the system.

The silver halide emulsion can be subjected to reduction sensitization. Reduction sensitizers include stannous salts, amines, formamidinesulfinic acid, and silane compounds.

The silver halide emulsions may contain a thiosulfonic acid compound according to the method disclosed in EP 293,917.

The light-sensitive material of the invention may contain either one kind of a silver halide emulsion or two or more kinds of emulsions differing in, e.g., average grain size, halogen composition, crystal habit, conditions of chemical sensitization.

Spectral sensitizing dyes which can be used in the present invention are not particularly limited. While varying depending on the shape and size of silver halide grains, spectral sensitizing dyes are used in an amount of $4 \times 10^{-6}$ to $8 \times 10^{-3}$ mol per mol of silver halide. For example, when the grains have a size of 0.2 to 1.3 μm, the dyes are preferably used in an amount of $2 \times 10^{-7}$ to $3.5 \times 10^{-6}$ mol, still preferably $6.5 \times 10^{-7}$ to $2.0 \times 10^{-6}$ mol, per $m^2$ of the surface area of the silver halide grains.

The light-sensitive silver halide emulsions may be spectrally sensitized to blue light of relatively long wavelength, green light, red light or infrared light with sensitizing dyes. Useful sensitizing dyes include cyanine dyes, merocyanine dyes, complex cyanine dyes, complex merocyanine dyes, holopolar cyanine dyes, styryl dyes, hemicyanine dyes, oxonol dyes, and hemioxonol dyes. Examples of useful sensitizing dyes are give in *Research Disclosure*, No. 17643, Item IV-A, p. 23 (December, 1978), ibid, No. 1831, Item X, p. 437 (August, 1978) and in the references cited therein.

Sensitizing dyes having spectral sensitivity agreeable with the spectral characteristics of various light sources of scanners can be selected to advantage. For example, sensitizing dyes suitable to argon lasers include the simple merocyanine dyes described in JP-A-60-162247, JP-A-2-48653, U.S. Pat. No. 2,161,331, West German Patent 936,071, and JP-A-5-11389; those suitable to helium-neon lasers include the trinuclear cyanine dyes described in JP-A-50-62425, JP-A-54-18726, and JP-A-59-102229; those suitable to LED and red semiconductor lasers include the thiacarbocyanine dyes described in JP-B-48-42172, JP-B-51-9609, JP-B-55-39818, JP-A-62-284343, and JP-A-2-105135; and those suitable to infrared semiconductor lasers include the tricarbocyanine dyes described in JP-A-59-191032 and JP-A-60-80841 and the dicarbocyanine dyes containing a 4-quinoline nucleus as represented by formulae (IIIa) and (IIIb) described in JP-A-59-192242 and JP-A-3-67242.

These sensitizing dyes may be used either individually or as a combination thereof. Combinations of sensitizing dyes are often used for the purpose of supersensitization. In addition to the sensitizing dyes, the emulsions may contain a dye which exhibits no spectral sensitizing effect by itself or absorbs no substantial visible light but which shows supersensitizing effect when combined with a sensitizing dye.

Examples of useful sensitizing dyes, combinations of dyes for supersensitization, and substances exhibiting supersensitizing effect when combined with sensitizing dyes are give in *Research Disclosure*, Vol. 176, No. 17643, p. 23, Item IV-J, (December, 1978).

Sensitizing dyes S1-1 to S1-13 disclosed in Japanese Patent Application No. 37823/95 are particularly suitable to argon lasers. Sensitizing dyes particularly suitable to helium-neon lasers include those mentioned above and those represented by formula (I) of JP-A-6-75322 (page 8, line 1 up to page 13, line 4). More specifically, the dyes S2-1 to S2-9 of Japanese Patent Application No. 37823/95 and the dyes described in JP-A-6-75322 and JP-A-7-287338 are all preferably used. Sensitizing dyes S3-1 to S3-8 of Japanese Patent Application No. 37823/95 are particularly suitable to LED and red semiconductor lasers. Sensitizing Dyes S4-1 to S4-9 of Japanese Patent Application No. 37823/95 are particularly suitable to infrared semiconductor lasers.

To white light used for, for example, photographing with cameras, sensitizing dyes represented by formula (IV) of JP-A-7-36139 (page 20, line 14 to page 22, line 23) are used for preference. Dyes S5-1 to S5-21 of Japanese Patent Application No. 37823/95 are mentioned as specific examples. In addition, the sensitizing dyes represented by formula (S6) of Japanese Patent Application No. 37823/95, specifically S6-1 to S6-11, are also preferred for white light sources.

The sensitizing dyes are added to silver halide emulsions in the form of an aqueous solution or a solution in a water-miscible organic solvent, e.g., methanol, ethanol, propyl alcohol, methyl cellosolve, pyridine.

The sensitizing dyes may be dissolved by ultrasonic vibration as described in U.S. Pat. No. 3,485,634. Other methods for adding sensitizing dyes to an emulsion in the form of a solution or a dispersion, described in U.S. Pat. Nos. 3,482,981, 3,585,195, 3,469,987, 3,425,835, and 3,342,605, British Patents 1,271,329, 1,038,029, and 1,121, 174, and U.S. Pat. Nos. 3,660,101 and 3,658,546, can also be used.

The sensitizing dyes are usually added to an emulsion before the emulsion is applied to an appropriate support. They may be added during chemical ripening or silver halide grain formation.

The sensitizing dyes may be used either individually or as a combination thereof. Combinations of sensitizing dyes are often used for the purpose of supersensitization. Examples of Useful sensitizing dyes, combinations of dyes for supersensitization, and substances exhibiting supersensitizing effect when combined with sensitizing dyes are give in *Research Disclosure*, Vol. 176, No. 17643, p. 23, Item IV-J, (December, 1978).

A developer which can be used for developing the light-sensitive material of the invention can contain additives generally employed, such as a developing agent, an alkali agent, a pH buffering agent, a preservative, a chelating agent, and the like. Any known technique for development processing and any known developer can be used.

While not particularly limiting, it is preferable that the developing agent used in the developer contains a dihydroxybenzene developing agent or an ascorbic acid derivative. From the standpoint of developing ability, a combination of a dihydroxybenzene developing agent and a 1-phenyl-3-pyrazolidone developing agent, a combination of a dihydroxybenzene developing agent and a p-aminophenol developing agent, a combination of an ascorbic acid derivative and a 1-phenyl-3-pyrazolidone developing agent, or a combination of an ascorbic acid derivative and a p-aminophenol developing agent are preferred.

The dihydroxybenzene developing agent includes hydroquinone, chlorohydroquinone, isopropylhydroquinone, methylhydroquinone, and a hydroquinone monosulfonate, with hydroquinone and a hydroquinone monosulfonate being preferred. These dihydroxybenzene developing agents are preferably used singly, while they may be used as a combination of two or more thereof.

The ascorbic acid derivative developing agent includes those described in JP-A-7-13306, and preferably ascorbic acid, erythorbic acid (a stereoisomer of ascorbic acid), or an alkali metal (e.g., Na, K) salt thereof. It is preferable not to use the ascorbic acid derivative developing agent in combination with the above-described dihydroxybenzene developing agent.

The 1-phenyl-3-pyrazolidone developing agent includes 1-phenyl-3-pyrazolidone,1-phenyl-4,4-dimethyl-3-pyrazolidone, and 1-phenyl-4-methyl-4-hydroxymethyl-3-pyrazolidone.

The p-aminophenol developing agent includes N-methyl-p-aminophenol, p-aminophenol, N-(β-hydroxyethyl)-p-aminophenol, and N-(4-hydroxyphenyl)glycine, with N-methyl-p-aminophenol being preferred.

The dihydroxybenzene developing agent is preferably used in an amount of from 0.05 to 0.8 mol/l, still preferably 0.2 to 0.6 mol/l. When the dihydroxybenzene is combined with a 1-phenyl-3-pyrazolidone developing agent or a p-aminophenol developing agent, the former is preferably used in an amount of 0.05 to 0.6 mol/l, still preferably 0.2 to 0.5 mol/l, and the latter is preferably used in an amount of not more than 0.06 mol/l, still preferably not more than 0.03 mol/l.

The ascorbic acid derivative developing agent is preferably used in an amount of 0.05 to 0.8 mol/l, still preferably 0.2 to 0.6 mol/l. When it is used in combination with a 1-phenyl-3-pyrazolidone or p-aminophenol developing agent, it is preferable to use the former in an amount of 0.05 to 0.6 mol/l, still preferably 0.2 to 0.5 mol/l, and the later not more than 0.06 mol/l, still preferably not more than 0.03 mol/l.

The preservative used in the developer includes sodium sulfite, potassium sulfite, lithium sulfite, ammonium sulfite, sodium bisulfite, potassium metabisulfate, and formaldehyde sodium bisulfite. The sulfite is used in an amount of not less than 0.20 mol/l, particularly not less than 0.3 mol/l. Since addition of too much the sulfite preservative tends to cause silver stain of the developer, a desired upper limit of the sulfite concentration is 1.2 mol/l. A particularly preferred sulfite concentration is 0.35 to 0.7 mol/l.

A small amount of an ascorbic acid derivative may be used in combination with a sulfite as a preservative for a dihydroxybenzene developing agent. Useful ascorbic acid derivatives include ascorbic acid, erythorbic acid (a stereoisomer of ascorbic acid) or an alkali metal (e.g., Na, K) salt thereof. Sodium erythorbate is preferred from the viewpoint of material cost. The ascorbic acid derivative is preferably used at a molar ratio of 0.03 to 0.12, still preferably 0.05 to 0.10, to the dihydroxybenzene developing agent. When the ascorbic acid derivative is used as a preservative, it is preferable that the developer contains no boron compound.

The alkali agent for pH adjustment of the developer includes generally employed water-soluble inorganic alkali metal salts, e.g., sodium hydroxide, potassium hydroxide, sodium carbonate, and potassium carbonate.

In addition to the above-mentioned additives, the developer may contain a development restrainer (e.g., sodium bromide, potassium bromide), an organic solvent (e.g., ethylene glycol, diethylene glycol, triethylene glycol, dimethylformamide); a development accelerator (e.g., alkanolamines (e.g., diethanolamine, triethanolamine), imidazole or an imidazole derivative); and an antifoggant or a black pepper preventive (e.g., mercapto compounds, indazole compounds, benzotriazole compounds, benzimidazole compounds). Examples of the antifoggant or black pepper preventive as referred to above are 5-nitroindazole, 5-p-nitrobenzoylaminoindazole, 1-methyl-5-nitroindazole, 6-nitroindazole, 3-methyl-5-nitroindazole, 5-nitrobenzimidazole, 2-isopropyl-5-nitrobenzimidazole, 5-nitrobenzotriazole, sodium 4-[(2-mercapto-1,3,4-thiadiazole-2-yl)thio]butanesulfonate,5-amino-1,3,4-thiadiazole-2-thiol, methylbenzotriazole, 5-methylbenzotriazole, and 2-mercaptobenzotriazole. These antifoggants are usually used in a concentration of 0.01 to 10 mmol/l, preferably 0.1 to 2 mmol/l.

The developer can further contain various organic or inorganic chelating agents. Suitable inorganic chelating agents include sodium tetrapolyphosphate and sodium hexametaphosphate. Typical organic chelating agents include organic carboxylic acids, aminopolycarboxylic acids, organic phosphonic acids, aminophosphonic acids, and organic phosphonocarboxylic acids.

Specific but non-limiting examples of the organic carboxylic acids are acrylic acid, oxalic acid, malonic acid, succinic acid, glutaric acid, adipic acid, pimelic acid, azelaic acid, sebacic acid, nonanedicarboxylic acid, decanedicarboxylic acid, undecanedicarboxylic acid, maleic acid, itaconic acid, malic acid, citric acid, and tartaric acid.

Specific examples of the aminopolycarboxylic acids include iminodiacetic acid, nitrilotriacetic acid, nitrilotripropionic acid, ethylenediaminemonohydroxyethyltriacetic acid, ethylenediaminetetraacetic acid, glycol ether tetraacetic acid, 1,2-diaminopropanetetraacetic acid, diethylenetriaminepentaacetic acid, triethylenetetraminehexaacetic acid, 1,3-diamino-2-propanoltetraacetic acid, glycol ether diaminetetraacetic acid, and the compounds described in JP-A-52-25632, JP-A-55-67747, JP-A-57-102624, and JP-B-53-40900.

The organic phosphonic acids include hydroxyalkylidenediphosphonic acids described in U.S. Pat. Nos. 3,214,454 and 3,794,591 and West German Patent OLS No. 2227639; and the compounds described in Research Disclosure, Vol. 181, Item 18170 (May, 1979).

The aminophosphonic acids include aminotris (methylenephosphonic acid), ethylenediaminetetramethylenephohsphonic acid, aminotrimethylenephosphonic acid; and the compounds described in Research Disclosure, No. 18170, JP-A-57-208554, JP-A-54-61125, JP-A-55-29883, and JP-A-56-97347.

The organic phosphonocarboxylic acids include the compounds described in JP-A-52-102726, JP-A-53-42730, JP-A-54-121127, JP-A-55-4024, JP-A-55-4025, JP-A-55-126241, JP-A-55-65955, JP-A-55-65956, and Research Disclosure, No. 18170.

These chelating agents may be used in the form of an alkali metal salt thereof or an ammonium salt thereof. The chelating agent is preferably added in a concentration of $1\times10^{-4}$ to $1\times10^{-1}$ mol/l, still preferably $1\times10^{-3}$ to $1\times10^{-2}$ mol/l.

The developer can further contain silver stain preventives, such as the compounds described in JP-A-56-24347, JP-B-56-46585, JP-B-62-2849, and JP-A-4-362942.

The developer can furthermore contain development unevenness preventive, such as the compounds described in JP-A-62-212651, and dissolution aids, such as the compounds described in JP-A-61-267759.

If desired, the developer may contain color toning agents, surface active agents, antifoaming agents, hardening agents, and so on.

The developer contains a buffering agent, such as carbonates, boric acid as described in JP-A-62-186259, saccharides as described in JP-A-60-93433 (e.g., saccharose), oximes (e.g., acetoxime), phenols (e.g., 5-sulfosalicylic acid), and tertiary phosphates (e.g., sodium, potassium salt), with carbonates and boric acid being preferred.

The developer preferably has a pH of 9.5 to 11.0, still preferably 9.8 to 10.7.

The processing temperature and time in development processing relate to each other and are decided in the light of the total processing time. In general, development processing is performed at about 20° to about 50° C., preferably 25° to 45° C., for 5 seconds to 2 minutes, preferably 7 seconds to 1.5 minutes.

In the development processing of a silver halide black-and-white light-sensitive material, for example, the development tank is replenished at a rate of 50 to 400 ml, preferably 100 to 180 ml, per $m^2$ of the light-sensitive material.

A fixing solution which can be used for fixing comprises an aqueous solution containing a fixing agent, such as sodium thiosulfate or ammonium thiosulfate, and, if desired, tartaric acid, citric acid, gluconic acid, boric acid, iminodiacetic acid, 5-sulfosalicylic acid, glucoheptanoic acid, Tiron, ethylenediaminetetraacetic acid, diethylenetriaminepentaacetic acid, nitrilotriacetic acid, or a salt of these acids. From the viewpoint of environmental conservation, it is recommended to avoid use of boric acid.

Usable fixing agents include sodium thiosulfate and ammonium thiocyanate. While ammonium thiosulfate is preferred for its high rate of fixing, sodium thiosulfate could be recommended from the standpoint of environmental conservation. The amount of the fixing agent is subject to variation and usually ranges from about 0.1 to about 2 mol/l and preferably from 0.2 to 1.5 mol/l.

If desired, the fixing solution may contain a hardening agent (e.g., a water-soluble aluminum salt), a preservative (e.g., a sulfite, a bisulfite), a pH buffering agent (e.g., acetic acid), a pH adjusting agent (e.g., ammonia, sulfuric acid), a chelating agent, a surface active agent, a wetting agent, and a fixing accelerator.

Suitable surface active agents include anionic surface active agents, such as sulfates and sulfonates, polyethylene type surface active agents, and amphoteric surface active agents, such as the compounds described in JP-A-57-6740. A known antifoaming agent may be added. Suitable wetting agents include alkanolamines and alkylene glycols. Suitable fixing accelerators include thiourea derivatives described in JP-B-45-35754, JP-A-58-122535, and JP-A-58-122536; alcohols having a triple bond in the molecule thereof; thioether compounds described in U.S. Pat. No. 4,126,459; and meso-ion compounds described in JP-A-4-229860. The compounds described in JP-A-2-44355 can also be used.

The pH buffering agents include organic acids, such as acetic acid, malic acid, succinic acid, tartaric acid, citric acid, oxalic acid, maleic acid, glycolic acid, and adipic acid; and inorganic buffer agents, such as boric acid, phosphates, and sulfites. Acetic acid, tartaric acid and sulfites are preferred.

The pH buffering agent is added for the purpose of preventing a pH rise of the fixing agent due to the carry-over of the developer into the fixing tank. It is preferably added to a concentration of 0.01 to 1.0 mol/l, still preferably 0.02 to 0.6 mol/l. The pH of the fixing solution preferably ranges from 4.0 to 6.5, still preferably 4.5 to 6.0.

The fixing solution may contain a dye elution accelerator, such as the compound described in JP-A-64-4739.

The hardening agent used in the fixing solution includes water-soluble ammonium salts and water-soluble chromium salts. Water-soluble ammonium salts are preferred. Examples of the water-soluble ammonium salts are aluminum chloride, aluminum sulfate, potassium alum, and an organic acid aluminum salt (e.g., aluminum lactate). The water-soluble aluminum salt is preferably added to a concentration of 0.01 to 0.2 mol/l, still preferably 0.03 to 0.08 mol/l.

The fixing is carried out at about 20° to about 50° C., preferably 25° to 45° C., for a period of 5 seconds to 1 minute, preferably 7 to 50 seconds.

The rate of replenishment for the fixing tank is 50 to 400 ml/$m^2$, preferably 100 to 300 ml/$m^2$.

After development and fixing, the light-sensitive material is subjected to washing or stabilization.

Washing or stabilization is usually carried out using not more than 20 l of water per $m^2$ of a silver halide light-sensitive material. The rate of replenishment may be reduced to 3 liters or even less per $m^2$, inclusive of zero (which means washing with no replenishment). That is, not only can water be saved but water piping for installing an automatic processor would be unnecessary.

A multistage (for example, two-stage or three-stage) countercurrent system has been known as a means for reducing the rate of replenishment in washing. According to the multistage countercurrent system, a light-sensitive material after fixation is successively treated with water approaching normality, i.e., becoming less contaminated with the fixing solution. Thus, application of this system to the present invention will achieve more efficient washing.

When washing is conducted with a reduced amount of water, it is preferable to provide a wash tank equipped with a squeegee roller or a cross-over roller as described in JP-A-63-18350 and JP-A-62-287252. In order to minimize pollution loading, which gives rise to a problem in the case of washing with a reduced amount of water, various oxidizing agents may be added, or a filtering mechanism may be used in combination.

A washing or stabilization tank may be replenished with water having been subjected to antifungal treatment with the progress of washing, and a part or the whole of the overflow resulting from the replenishment can be fed to the preceding bath having fixing ability as proposed in JP-A-60-235133.

A water-soluble surface active agent or antifoaming agent may be added to water in order to prevent unevenness due to foaming and/or to prevent a processing component adhered to the squeegee roller from being transferred to a processed film.

The dye adsorbent described in JP-A-63-163456 may be put in a wash tank in order to prevent contamination with the dye dissolved out of a light-sensitive material.

The above-described washing may sometimes be followed by stabilization. In this case, a stabilizing bath containing the compound disclosed in JP-A-2-201357, JP-A-2-132435, JP-A-1-102553 or JP-A-46-44446 can be used as a final bath.

If desired, the stabilizing bath may also contain an ammonium compound, a metal compound (e.g., Bi or Al compound), a fluorescent brightening agent, a chelating agent, a membrane pH adjusting agent, a hardening agent, a bactericidal agent, an antifungal agent, an alkanolamine, or a surface active agent. Water used for washing or stabilization preferably includes deionized water or water sterilized by means of an ultraviolet sterilization lamp or various oxidizing agents (e.g., ozone, hydrogen peroxide, a chloric acid salt) as well as tap water. Water containing the compound described in JP-A-4-39652 or JP-A-5-241309 is also useful.

Washing or stabilization is preferably carried at a bath temperature of 0° to 50° C. for 5 seconds to 2 minutes.

When low throughput replenishment is adopted, it is preferable to minimize the contact area of processing solutions with air to prevent air oxidation. An automatic processor of roller transport system (hereinafter referred to as roller transport processor) is mentioned in U.S. Pat. Nos. 3,025,779 and 3,545,971. The roller transport processor comprises a development step, a fixing step, a washing step, and a drying step. These four steps are preferably followed in the present invention as well, which does not mean that other steps, e.g., a stopping step, are excluded. The washing step may be replaced with a stabilization step. Drying in an automatic processor is preferably carried out by hot air drying by a roller transport system or heat drum drying by means of a heat roller.

The components of a developer or a fixing solution other than water may be supplied in the form of solid, which can be dissolved with a prescribed amount of water to prepare a developer or a fixing solution on use. Such solid components are called solid processing chemicals. Solid processing chemicals may be powders, tablets, granules, lumps or pastes. Tablets and the preparation form described in JP-A-61-259921 are preferred. Tablets are prepared by general methods as described, e.g., in JP-A-51-61837, JP-A-54-155038, JP-A-52-88025, and British Patent 1,213,808. Granules are prepared by general methods as described, e.g., in JP-A-2-109042, JP-A-2-109043, JP-A-3-39735, and JP-A-3-39739. Powders are prepared by general methods as described, e.g., in JP-A-54-133332, British Patents 725,892 and 729,862, and German Patent 3,733,861.

From the standpoint of solubility and in view of the effects expected of the invention, these solid processing chemicals preferably have a density of 0.5 to 6.0 g/cm$^3$, still preferably 1.0 to 5.0 g/cm$^3$.

Solid processing chemicals can also be prepared by layering at least two of substances constituting processing chemicals, which are reactive to each other and are each in the form of particles, with at least one partitioning layer made up of a substance inert to each of the constituent substances being interposed therebetween, in a bag made of a material for vacuum packaging, and evacuating and sealing the bag. The term "inert" as used above means that a substance does not undergo reaction with another substance on physical contact therewith under usual conditions within a package or, the reaction, if any, does not take place to an appreciable degree. Besides being inert to the mutually reactive two substances, the inert substance should be inactive under the condition in which the two reactive substances are intended to be used. Further, the inert substance is selected from the substances which are used simultaneously with the two reactive substances. For instance, since hydroquinone and sodium hydroxide, which are components of a developer, react with each other immediately upon direct contact or sodium sulfite can be interposed therebetween as a partitioning layer in vacuum packaging, whereby these components can be stored for a long period of time. Wrapping materials used in vacuum packaging are bags made of inert plastic films or laminates of a plastic film and a metal foil.

Other various additives which can be used in the present invention are not particularly limited. For example, the additives described in the following references can be used for preference.

1) Surface active agents and antistatic agents:

The compounds described in JP-A-2-12236, p. 9, upper right column (abbreviated as UR), line 7 to lower right column (abbreviated as LR) and JP-A-2-18542, p. 2, lower left column (abbreviated as LL), line 13 to p. 4, lower right column (abbreviated as LR), line 18; and the compounds of formula (II) described in JP-A-7-287335.

2) Antifoggants and stabilizers:

The compounds described in JP-A-2-103536, p. 17, LR, line 19 to p. 18, UR, line 4 and LR, lines 1–5; and the thiosulfinic acid compounds described in JP-A-1-237538.

3) Polymer latex:

The compounds described in JP-A-2-103536, p. 18, LL, lines 12 to 20.

4) Compounds having acid radical:

The compounds described in JP-A-2-103536, p. 8, LR, line 5 to p. 19, UL, line 1 and JP-2-55349, p. 8, LR, line 13 to p. 11, UL, line 8.

5) Matting agents, slip agents, and plasticizers:

The compounds described in JP-A-2-103536, p. 19, UL, line 15 to p. 19, UR, line 15.

6) Hardening agents:

The compounds described in JP-A-2-103536, p. 18, UR, lines 5–17.

7) Dyes:

The compounds described in JP-A-2-103536, p. 17, LR, lines 1-18 and JP-A-2-30042, p. 4, UR, line 1 to p. 6, UR, line 5; and the solid dyes described in JP-A-2-294638 and JP-A-5-11382.

8) Binders:

The compounds described in JP-A-2-18542, p. 3, LR, lines 1-20.

9) Black pepper preventives:

The compounds described in U.S. Pat. No. 4,956,257 and JP-A-1-118832.

10) Redox compounds:

The compounds of formula (1) of JP-A-2-301743 (especially compound Nos. 1 to 50), the compounds of formulae (R-1), (R-2) and (R-3) of JP-A-3-174143 (especially compound Nos. 1 to 75), and the compounds described in Japanese Patent Application No. 69466/91 and JP-A-4-278939.

11) Monomethine compounds:

The compounds of formula (II) of JP-A-2-287532 (especially compound Nos. II-1 to II-26).

12) Dihydroxybenzene compounds:

The compounds described in JP-A-3-39948, p. 11, UL to p. 12, LL and EP 452,772A.

The present invention will now be illustrated in greater detail by way of Examples, but it should be understood that the present invention is not deemed to be limited thereto. All the percents are by weight unless otherwise indicated.

EXAMPLE 1

1) Preparation of Light-Sensitive Emulsions:

A silver nitrate aqueous solution and a silver halide aqueous solution containing potassium bromide, sodium chloride, $3.5 \times 10^{-7}$ mol/mol-Ag of $K_3IrCl_6$, and $2.0 \times 10^{-7}$ mol/mol-Ag of $K_2Rh(H_2O)Cl_5$ were simultaneously added to a gelatin aqueous solution containing sodium chloride and 1,3-dimethyl-2-imidazolidinethione with stirring according to a double jet process to prepare silver chlorobromide grains having a mean grain size of 0.25 μm and a silver chloride content of 70 mol %.

After washing by a well-known flocculation method, 40 g of gelatin per mol of silver was added to the emulsion. To the emulsion were further added 7 mg/mol-Ag of sodium benzenethiosulfonate and 2 mg/mol-Ag of benzenesulfinic acid. The emulsion was adjusted to pH 6.0 and pAg 7.5, and 2 mg/mol-Ag of sodium thiosulfate and 4 mg/mol-Ag of chloroauric acid to carry out chemical sensitization at 60° C. to reach to the optimum sensitivity. Thereafter, 150 mg of 4-hydroxy-6-methyl-1,3,3a,7-tetraazaindene was added as a stabilizer, and 100 mg of Proxel was added as an antiseptic. The resulting emulsion grains were cubic silver chlorobromide grains having a mean grain size of 0.25 μm (coefficient of variation: 10%) and a silver chloride content of 70 mol %. The resulting emulsion is designated emulsion A.

2) Preparation of Coated Sample:

A polyethylene terephthalate film support having a moistureproof subbing layer containing vinylidene chloride was coated successively with an UL layer, an EM layer, a PC layer, and an OC layer in this order to prepare a coated sample.

Preparation and coating weight of each layer are described below.

UL Layer:

A gelatin aqueous solution having added thereto a dispersion of polyethyl acrylate (30% based on gelatin) was applied to give a gelatin coating weight of 0.5 g/m².

EM Layer:

To emulsion A were added $5 \times 10^{-4}$ mol/mol-Ag of sensitizing dye (S-1), $5 \times 10^{-4}$ mol/mol-Ag of sensitizing dye (S-2), $3 \times 10^{-4}$ mol/mol-Ag of mercapto compound (a), $4 \times 10^{-4}$ mol/mol-Ag of mercapto compound (b), $4 \times 10^{-4}$ mol/mol-Ag of triazine compound (c), $2 \times 10^{-3}$ mol/mol-Ag of 5-chloro-8-hydroxyquinoline, $5 \times 10^{-4}$ mol/mol-Ag of compound (P), and $4 \times 10^{-4}$ mol/mol-Ag of compound (A) as nucleation accelerator. Further, 100 mg/m² of hydroquinone and 30 mg/m² of sodium N-oleyl-N-methyltaurine were added. Then the nucleating agent shown in Table 1 below (hydrazine derivative) of the amount shown, 200 mg/m² of water-soluble latex (d), 200 mg/m² of a polyethyl acrylate dispersion, 200 mg/m² of a latex copolymer comprising methyl acrylate, sodium 2-acrylamido-2-methylpropanesulfonate, and 2-acetoacetoxyethyl methacrylate (88:5:7 by weight), 200 mg/m² of colloidal silica having an average particle size of 0.02 μm, and 200 mg/m² of 1,3-divinylsulfonyl-2-propanol as a hardener were added. The resulting coating composition was adjusted to pH 5.65 with acetic acid and applied to give a silver coating weight of 3.5 g/m².

PC Layer:

An aqueous gelatin solution having added thereto 50% of an ethyl acrylate dispersion based on gelatin, 5 mg/m² of surface active agent (w), and 10 mg/m² of 1,5-dihydroxy-2-benzaldoxime was applied to give a gelatin coating weight of 0.5 g/m².

OC Layer:

A coating composition comprising 0.5 g/m² of gelatin, 40 mg/m² of an amorphous silica matting agent having an average particle size of about 3.5 μm, 0.1 g/m² of methanol silica, 100 mg/m² of polyacrylamide, 20 mg/m² of silicone oil, and, as coating aid, 5 mg/m² of fluorine type surface active agent (e) and 100 mg/m² of sodium dodecylbenzenesulfonate was applied.

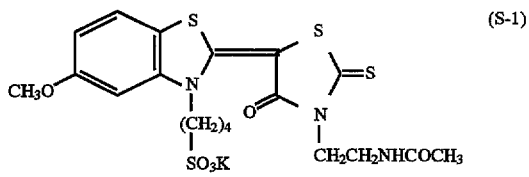

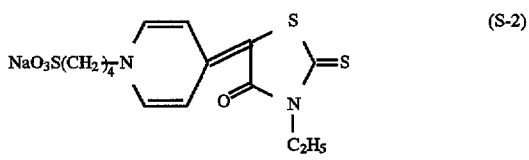

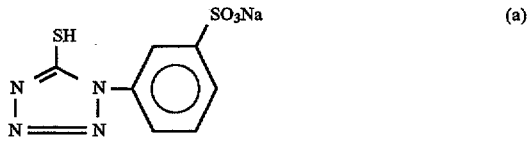

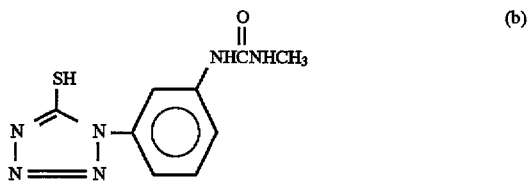

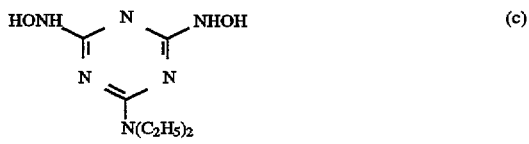

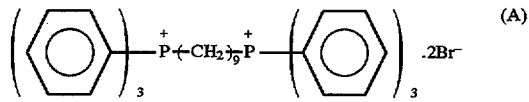

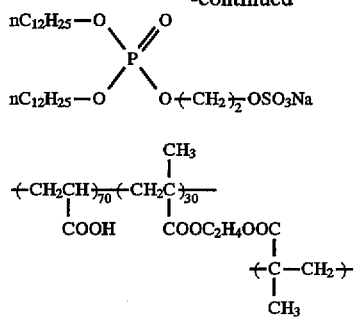

(p) 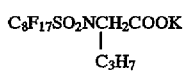 (e)

(d) 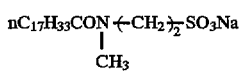 (w)

On the opposite side of the support were provided a backing layer and a back protective layer having the following formulation.

| Backing Layer: | |
|---|---|
| Gelatin | 3 g/m² |
| Polyethyl acrylate latex | 2 g/m² |
| Sodium p-dodecylbenzenesulfonate (surface active agent) | 40 mg/m² |
|  | 110 mg/m² |
| SnO₂/Sb (90/10 by weight; average particle size: 0.20 μm) | 200 mg/m² |
| Dye mixture of: | |
| (a) 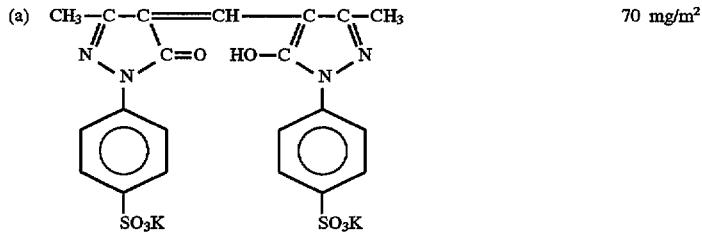 | 70 mg/m² |
| (b) 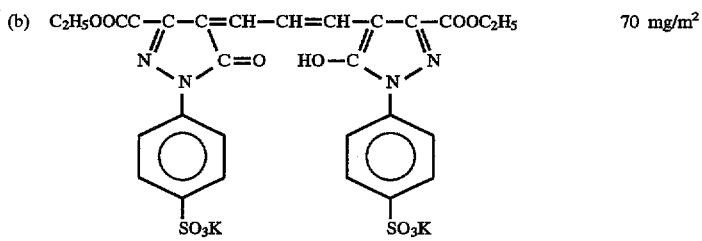 | 70 mg/m² |
| (c) 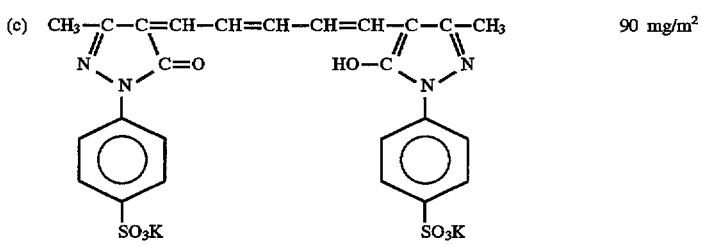 | 90 mg/m² |
| Back Protective Layer: | |
| Gelatin | 0.8 mg/m² |
| Polymethyl methacrylate fine particles (average particle size: 4.5 μm) | 30 mg/m² |
| Sodium dihexyl-α-sulfosuccinate | 15 mg/m² |
| Sodium p-dodecylbenzenesulfonate | 15 mg/m² |
| Sodium acetate | 40 mg/m² |

3) Processing:

The resulting coated sample was exposed to light through an interference filter having the peak at 488 nm via a step wedge using a xenon flash lamp having a flash duration of $10^{-5}$ sec. The exposed sample was developed with developer A having the following formulation at 35° C. for 30 seconds, fixed with a fixing solution having the following formulation, washed, and dried.

| Formulation of Developer A: | |
| --- | --- |
| Potassium hydroxide | 35.0 g |
| Diethylenetriaminepentaacetic acid | 2.0 g |
| Potassium carbonate | 12.0 g |
| Sodium metabisulfite | 40.0 g |
| Potassium bromide | 3.0 g |
| Hydroquinone | 25.0 g |
| 5-Methylbenzotriazole | 0.08 g |
| 4-Hydroxymethyl-4-methyl-1-phenyl-3-pyrazolidone | 0.45 g |
| 2,3,5,6,7,8-Hexahydro-2-thioxo-4-(1H)-quinazolinone | 0.04 g |
| Sodium 2-mercaptobenzimidazole-5-sulfonate | 0.15 g |
| Sodium erythorbate | 3.0 g |
| Water to make | 1 l |
| pH (adjusted with potassium hydroxide) | 10.5 |
| Formulation of Fixing Solution: | |
| Ammonium thiosulfate | 359.1 ml |
| Disodium ethylenediaminetetraacetate dihydrate | 2.26 g |
| Sodium thiosulfate pentahydrate | 32.8 g |
| Sodium sulfite | 64.8 g |
| Sodium hydroxide | 37.2 g |
| Glacial acetic acid | 87.3 g |
| Tartaric acid | 8.76 g |
| Sodium gluconate | 6.6 g |
| Aluminum sulfate | 25.3 g |
| Water to make | 1 l |
| pH (adjusted with sulfuric acid or sodium hydroxide) | 4.85 |

4) Evaluation of Photographic Properties:

4-1) Contrast:

A characteristic curve was prepared. The slope of a straight line connecting the point of (fog+0.1) and the point of (fog+3.0) was taken as γ indicative of image contrast. That is, γ=(3.0−0.1)/[log(exposure providing density 3.0)−log(exposure providing density 0.1)]. The greater the γ value, the higher the contrast. It is desirable for a light-sensitive material for graphic arts to have γ of 10 or higher, particularly 15 or higher.

4-2) Preservability:

The coated sample was allowed to stand under conditions of 60° C. and 65% RH for 3 days.

4-2-1) Retention of nucleating agent:

The nucleating agent was extracted from the coated sample immediately after coating and the coated sample after preservation and quantitatively determined by high-performance liquid chromatography.

Retention (%) = [(amount of nucleating agent extracted from the preserved sample (65° C., 65% RH × 3 days)/(amount of nucleating agent extracted from the sample immediately after coating)] × 100

4-2-2) Change of sensitivity:

Each of the preserved sample and the sample immediately after coating was developed, and the difference in sensitivity ($\Delta S_{1.5}$) between the two samples was obtained.

Sensitivity ($S_{1.5}$): logarithm of an exposure providing a density of 1.5 (the smaller the $S_{1.5}$, the higher the sensitivity)

$\Delta S_{1.5}$ = ($S_{1.5}$ of the sample immediately after coating) - ($S_{1.5}$ of the preserved sample), expressed by an absolute value (the smaller the $\Delta S_{1.5}$, the smaller the change in sensitivity, i.e., the higher the performance)

The results of the evaluation are shown in Table 1 below.

TABLE 1

| Run No. | Nucleating Agent (Hydrazine Deriv.) | | γ | Preservability | | Remark |
| --- | --- | --- | --- | --- | --- | --- |
| | Kind | Amount (mol/m²) | | Retention of Nucleating Agent | $\Delta S_{1.5}$ | |
| 1 | Cpd. A* | $1.0 \times 10^{-5}$ | 7.2 | 83 | 0.05 | Comparison |
| 2 | Cpd. B* | " | 7.4 | 83 | 0.05 | " |
| 3 | Cpd. C* | " | 8.6 | 82 | 0.06 | " |
| 4 | Cpd. D* | " | 7.2 | 80 | 0.07 | " |
| 5 | Cpd. E* | $2.0 \times 10^{-6}$ | 18.2 | 72 | 0.10 | " |
| 6 | Cpd. F* | " | 7.2 | 95 | 0 | " |
| 7 | Cpd. G* | " | 7.8 | 98 | 0 | " |
| 8 | Cpd. H* | " | 15.6 | 70 | 0 | " |
| 9 | Cpd. I* | $1.0 \times 10^{-6}$ | 7.9 | 65 | 0.05 | " |
| 10 | I-1 | $2.0 \times 10^{-6}$ | 18.2 | 94 | 0 | Invention |
| 11 | I-2 | " | 16.3 | 93 | 0 | " |
| 12 | I-4 | " | 16.5 | 92 | 0.01 | " |
| 13 | I-10 | " | 18.1 | 94 | 0 | " |
| 14 | I-11 | " | 16.7 | 92 | 0.01 | " |
| 15 | I-14 | " | 16.8 | 91 | 0.01 | " |
| 16 | I-16 | " | 17.0 | 94 | 0 | " |
| 17 | I-18 | " | 16.6 | 91 | 0.02 | " |
| 18 | I-21 | " | 15.8 | 91 | 0.01 | " |
| 19 | I-27 | " | 18.0 | 93 | 0 | " |
| 20 | I-35 | " | 17.2 | 92 | 0.01 | " |
| 21 | I-43 | " | 18.1 | 91 | 0.02 | " |
| 22 | I-65 | " | 18.7 | 90 | 0.03 | " |

*Comparative compounds A to I (hereinafter the same):

TABLE 1-continued

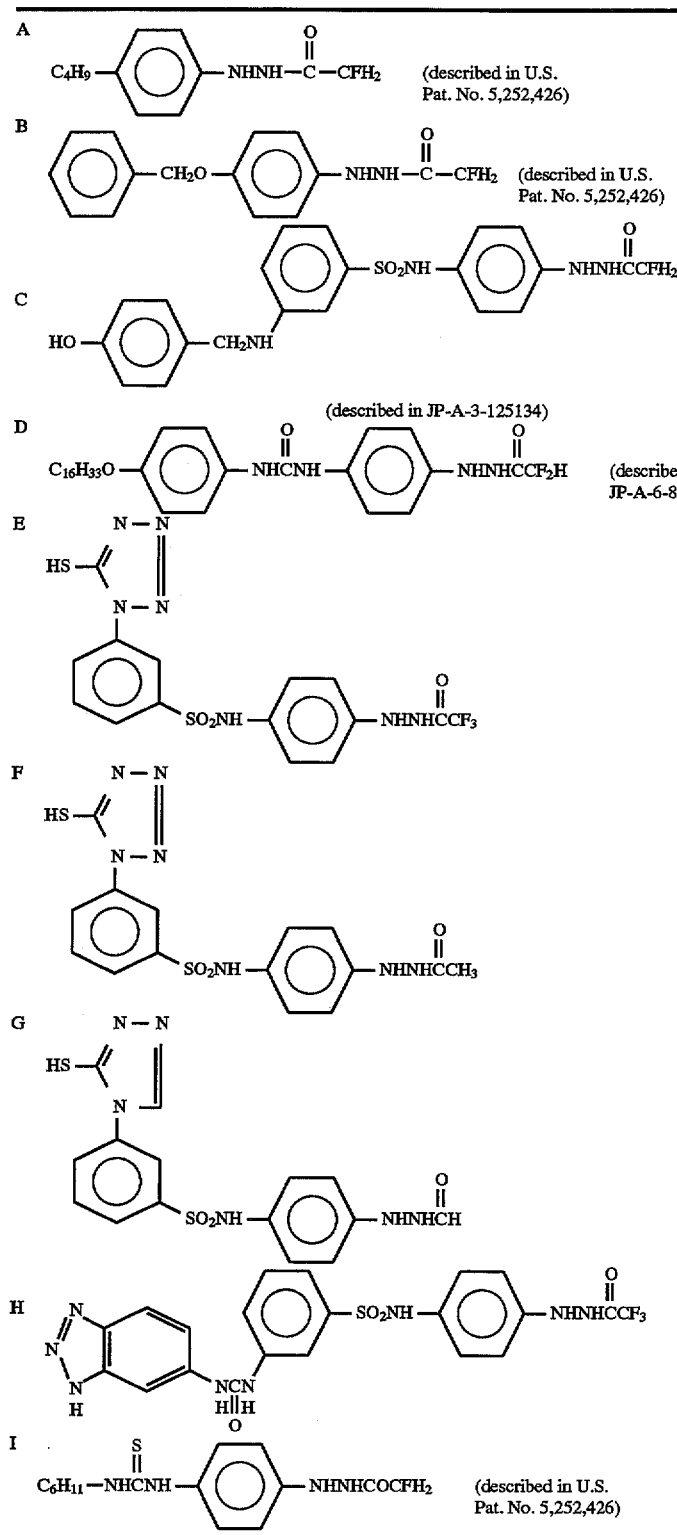

It can be seen from the results in Table 1 that comparative compounds A to D, F, G and I have too low nucleating activity to provide satisfactory photographic properties and that comparative compounds E and H which exhibit satisfactory nucleating activity do not withstand practical use because of their poor preservation stability. On the other hand, the nucleating agents according to the invention provide light-sensitive materials for argon laser scanning which exhibit high gamma characteristics and satisfactory preservability.

EXAMPLE 2

1) Preparation of Light-Sensitive Emulsion:

Emulsion B was prepared in the same manner as for emulsion A except that the primitive emulsion was chemically sensitized by adding 1 mg/mol-Ag of a selenium sensitizer shown below, 4 mg/mol-Ag of sodium thiosulfate, and 4 mg/mol-Ag of chloroauric acid and allowing to ripe at 60° C. to reach to the optimum sensitivity.

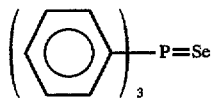

2) Preparation of Coated Sample:

A coated sample was prepared in the same manner as in Example 1 except for replacing sensitizing dyes (S-1) and (S-2) with $2.1 \times 10^{-4}$ mol/mol-Ag of sensitizing dye (S-3) and replacing emulsion A with emulsion B in the EM layer.

(S-3):

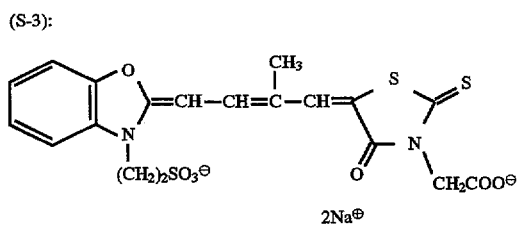

4) Processing:

The resulting coated sample was exposed to light through an interference filter having the peak at 633 nm via a step wedge using a xenon flash lamp having a flash duration of $10^{-6}$ sec. The exposed sample was developed with the same developer as used in Example 1 (developer A) at 35° C. for 30 seconds, fixed with the same fixing solution as used in Example 1, washed, and dried.

5) Evaluation of Photographic Properties:

The processed sample was evaluated in terms of image contrast and preservability in the same manner as in Example 1.

As a result, it was proved that the nucleating agents according to the invention provide light-sensitive materials for helium-neon laser scanning which exhibit high gamma characteristics and satisfactory preservability.

EXAMPLE 3

1) Preparation of Coated Sample:

A coated sample was prepared in the same manner as in Example 2 except for replacing sensitizing dye (S-3) used in the EM layer with sensitizing dye (S-4) shown below.

(S-4):

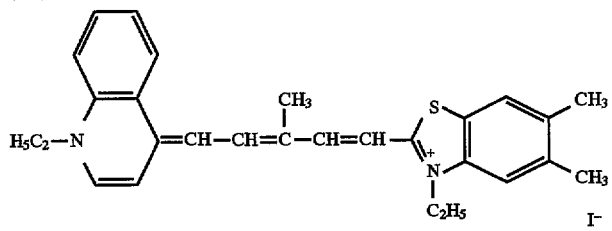

2) Evaluation of Photographic Properties:

The resulting coated sample was exposed to light through an interference filter having the peak at 780 nm via a step wedge using a xenon flash lamp having a flash duration of $10^{-6}$ sec. The exposed sample was developed with developer A used in Example 1 at 35° C. for 30 seconds, fixed with the same fixing solution as used in Example 1, washed, and dried.

The processed sample was evaluated in terms of image contrast and preservability in the same manner as in Example 2.

As a result, it was proved that the nucleating agents according to the invention provide light-sensitive materials for semiconductor laser scanning which exhibit high gamma characteristics and satisfactory preservability.

EXAMPLE 4

1) Preparation of Coated Sample:

A coated sample was prepared in the same manner as in Example 2 except for replacing sensitizing dye (S-3) used in the EM layer with sensitizing dye (S-5) shown below. The nucleating agent used is shown in Table 2 below.

(S-5):

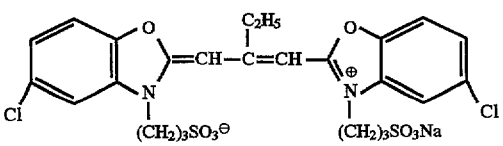

2) Evaluation of Photographic Properties:

The resulting coated sample was exposed to tungsten light having a color temperature of 3200° K. via a step wedge. The exposed sample was developed with developer A described in Example 1 at 35° C. for 30 seconds, fixed with a fixing solution GR-F1 (produced by Fuji Photo Film Co., Ltd.), washed, and dried.

The processed sample was evaluated in terms of image contrast and preservability in the same manner as in Example 2. The results obtained are shown in Table 2 below.

TABLE 2

| Run No. | Nucleating Agent Kind | Amount (mol/m²) | γ | Preservability Retention of Nucleating Agent | $\Delta S_{1.5}$ | Remark |
|---|---|---|---|---|---|---|
| 1 | Cpd. A | $1.0 \times 10^{-5}$ | 7.3 | 83 | 0.06 | Comparison |
| 2 | Cpd. B | $1.0 \times 10^{-5}$ | 7.4 | 83 | 0.06 | Comparison |
| 3 | Cpd. C | $1.0 \times 10^{-5}$ | 8.5 | 82 | 0.06 | Comparison |
| 4 | Cpd. D | $1.0 \times 10^{-5}$ | 7.3 | 80 | 0.08 | Comparison |
| 5 | Cpd. E | $2.0 \times 10^{-5}$ | 18.0 | 72 | 0.12 | Comparison |
| 6 | Cpd. F | $2.0 \times 10^{-5}$ | 7.1 | 95 | 0 | Comparison |
| 7 | Cpd. G | $2.0 \times 10^{-5}$ | 7.4 | 98 | 0 | Comparison |
| 8 | Cpd. H | $2.0 \times 10^{-5}$ | 15.3 | 70 | 0.13 | Comparison |
| 9 | Cpd. I | $1.0 \times 10^{-5}$ | 7.6 | 65 | 0.06 | Comparison |
| 10 | I-1 | $2.0 \times 10^{-6}$ | 17.6 | 94 | 0 | Invention |
| 11 | I-2 | $2.0 \times 10^{-6}$ | 15.9 | 93 | 0 | Invention |
| 12 | I-4 | $2.0 \times 10^{-6}$ | 16.1 | 92 | 0.01 | Invention |
| 13 | I-10 | $2.0 \times 10^{-6}$ | 17.7 | 94 | 0 | Invention |
| 14 | I-11 | $2.0 \times 10^{-6}$ | 16.4 | 92 | 0.01 | Invention |
| 15 | I-14 | $2.0 \times 10^{-6}$ | 16.3 | 91 | 0.02 | Invention |
| 16 | I-16 | $2.0 \times 10^{-6}$ | 16.4 | 94 | 0 | Invention |
| 17 | I-18 | $2.0 \times 10^{-6}$ | 16.1 | 91 | 0.03 | Invention |
| 18 | I-21 | $2.0 \times 10^{-6}$ | 15.2 | 91 | 0.02 | Invention |
| 19 | I-27 | $2.0 \times 10^{-6}$ | 18.1 | 93 | 0 | Invention |
| 20 | I-35 | $2.0 \times 10^{-6}$ | 17.0 | 92 | 0.02 | Invention |
| 21 | I-43 | $2.0 \times 10^{-6}$ | 17.5 | 91 | 0.02 | Invention |
| 22 | I-65 | $2.0 \times 10^{-6}$ | 18.2 | 90 | 0.04 | Invention |

The results in Table 2 prove that the nucleating agents according to the invention provide light-sensitive for photographing which exhibit high gamma characteristics and satisfactory preservability.

EXAMPLE 5

Coated samples were prepared by basically following the formulation described in Example 5 of JP-A-7-43867 and using the hydrazine derivatives of the present invention. The coated samples were processed and evaluated in the same manner as in Example 4. As a result, it was revealed that the nucleating agents of the invention provide light-sensitive materials for photographing which exhibit high gamma characteristics and satisfactory preservability.

EXAMPLE 6

1) Preparation of Light-Sensitive Emulsion:

To a 1.5% gelatin aqueous solution containing sodium chloride and $3 \times 10^{-5}$ mol/mol-Ag of compound (f), adjusted to pH 2.0 and kept at 40° C., were added simultaneously a silver nitrate aqueous solution and a sodium chloride aqueous solution containing $3.5 \times 10^{-5}$ mol/mol-Ag of $(NH_4)_2Rh(H_2O)Cl_5$ at a potential of 95 mV over a period of 3.5 minutes in accordance with a double jet process to prepare core grains having a grain size of 0.12 μm. To the emulsion were added a silver nitrate aqueous solution and a sodium chloride aqueous solution containing $10.5 \times 10^{-5}$ mol/mol-Ag of $(NH_4)_2Rh(H_2O)Cl_5$ in the same manner as described above over a 7-minute period to prepare cubic silver chloride grains having a mean grain size of 0.15 μm (coefficient of variation: 12%).

To the emulsion was added $1.5 \times 10^{-3}$ mol/mol-Ag of 4-hydroxy-6-methyl-1,3,3a,7-tetraazaindene.

The emulsion was washed by a well-known flocculation method to remove soluble salts, and gelatin was added. To the emulsion as primitive were further added 50 mg/mol-Ag of compound (g), 50 mg/mol-Ag of phenoxyethanol as antiseptics and $3 \times 10^{-3}$ mol/mol-Ag of 4-hydroxy-6-methyl-1,3,3a,7-tetraazaindene as a stabilizer. The emulsion was adjusted to pH 5.7 and pAg 7.5. The rhodium content in the emulsion was $6 \times 10^{-5}$ mol/mol-Ag. The resulting emulsion is designated emulsion C.

2) Preparation of Coated Sample:

The following compounds were added to emulsion C.

| | |
|---|---|
| 4-Hydroxy-6-methyl-1,3,3a,7-tetraazaindene | 10 mg/m² |
| Sodium N-oleyl-N-methyltaurine | 35 mg/m² |
| Compound (h) | 10 mg/m² |
| Compound (i) | 20 mg/m² |
| N-Butyl acrylate/2-acetoacetoxyethyl methacrylate/acrylic acid copolymer (89/8/3 by weight) | 900 mg/m² |
| Compound (j) (hardening agent) | 150 mg/m² |

To the composition was further added 20 mg/m² of compound (k) as a nucleation accelerator and the nucleating agent shown in Table 3 below in the amount shown to prepare a coating composition. The coating composition was applied to a support hereinafter described to form a silver halide emulsion layer having a gelatin coating weight of 1.1 g/m² and a silver coating weight of 2.5 g/m².

The following lower protective layer and upper protective layer were provided on the emulsion layer.

Lower Protective Layer:

The compounds shown below were added to a gelatin aqueous solution, and the resulting coating composition was applied to give a gelatin coating weight of 0.7 g/m².

| | |
|---|---|
| Gelatin (Ca⁺⁺ content: 2700 ppm) | 0.7 g/m² |
| Sodium p-dodecylbenzenesulfonate | 15 mg/m² |
| Compound (g) | 5 mg/m² |
| Compound (l) | 10 mg/m² |
| Compound (m) | 20 mg/m² |

Upper Protective Layer:

The compounds shown below were added to a gelatin aqueous solution, and the resulting coating composition was applied to give a gelatin coating weight of 0.8 g/m².

| | |
|---|---|
| Gelatin (Ca⁺⁺ content: 2700 ppm) | 0.8 g/m² |
| Amorphous silica matting agent (average particle size: 3.5 μm; pore diameter: 25 Å; surface area: 700 m²/g) | 40 mg/m² |
| Amorphous silica matting agent (average particle size: 2.5 μm; pore diameter: 170 Å; surface area: 300 m²/g) | 10 mg/m² |
| Potassium N-perfluorooctanesulfonyl-N-propylglycine | 5 mg/m² |
| Sodium dodecylbenzenesulfonate | 30 mg/m² |
| Compound (g) | 5 mg/m² |
| Solid disperse dye $G_1$ | 100 mg/m² |
| Solid disperse dye $G_2$ | 50 mg/m² |

On the opposite side of the support the following conductive layer and backing layer were provided simultaneously.

Conductive Layer:

The following compounds were added to a gelatin aqueous solution, and the resulting coating composition was applied to give a gelatin coating weight of 77 mg/m².

| | |
|---|---|
| SnO₂/Sb (9/1 by weight; average particle size: 0.25 μm) | 200 mg/m² |
| Gelatin (Ca⁺⁺ content: 3000 ppm) | 77 mg/m² |

-continued

| | |
|---|---|
| Sodium dodecylbenzenesulfonate | 10 mg/m² |
| Sodium dihexyl-α-sulfosuccinate | 40 mg/m² |
| Poly(sodium styrenesulfonate) | 9 mg/m² |
| Compound (g) | 7 mg/m² |

Backing Layer:

The following compounds were added to a gelatin aqueous solution, and the resulting coating composition was applied to give a gelatin coating weight of 2.92 mg/m².

| | |
|---|---|
| Gelatin (Ca++ content: 30 ppm) | 2.92 g/m² |
| Polymethyl methacrylate fine particles (average particle size: 3.4 μm) | 54 mg/m² |
| Compound (h) | 140 mg/m² |
| Compound (r) | 140 mg/m² |
| Compound (s) | 40 mg/m² |
| Sodium dodecylbenzenesulfonate | 75 mg/m² |
| Sodium dihexyl-α-sulfosuccinate | 20 mg/m² |
| Compound (t) | 5 mg/m² |
| Potassium N-perfluorooctanesulfonyl-N-propylglycine | 5 mg/m² |
| Sodium sulfate | 50 mg/m² |
| Sodium acetate | 85 mg/m² |

Support:

Both sides of a biaxially stretched polyethylene terephthalate film support (thickness: 100 μm) were coated with the following first and second subbing layers.

| First Subbing Layer: | |
|---|---|
| Core/shell type vinylidene chloride copolymer (1) | 15 g |
| 2,4-Dichloro-6-hydroxy-2-triazine | 0.25 g |
| Polystyrene fine particles (average particle size: 3 μm) | 0.05 g |
| Compound (u) | 0.20 g |
| Colloidal silica (Snowtex ZL, produced by Nissan Chemical industries, Ltd; particle size: 70 to 100 μm) | 0.12 g |
| Water to make | 100 g |

After adjusting to pH 6 with 10% of potassium hydroxide, the coating composition was applied to a dry thickness of 0.9 μm and dried at 180° C. for 2 minutes.

| Second Subbing Layer: | |
|---|---|
| Gelatin | 1 g |
| Methyl cellulose | 0.05 g |
| Compound (v) | 0.02 g |
| $C_{12}H_{25}O(CH_2CH_2O)_{10}H$ | 0.03 g |
| Compound (g) | $3.5 \times 10^{-3}$ g |
| Acetic acid | 0.2 g |
| Water to make | 100 g |

The above composition was applied to a dry thickness of 0.1 μm and dried at 170° C. for 2 minutes.

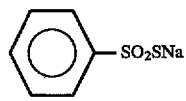

(f)

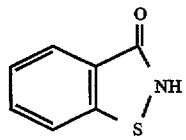

(g)

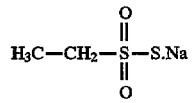

(h)

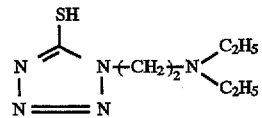

(i)

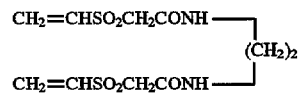

(j)

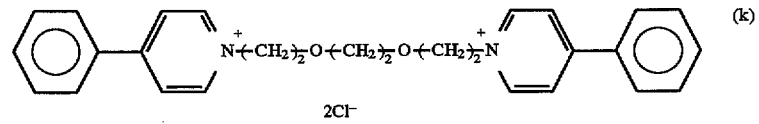

(k)

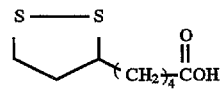

(l)

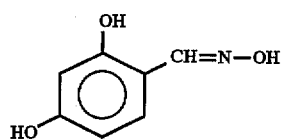
(m)
Solid disperse dye G₁
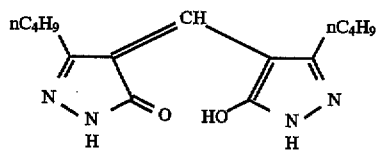
Solid disperse dye G₂
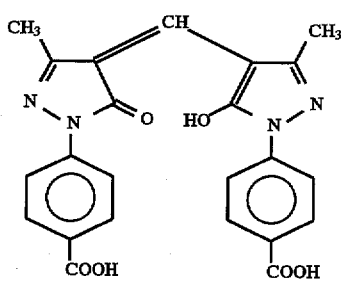
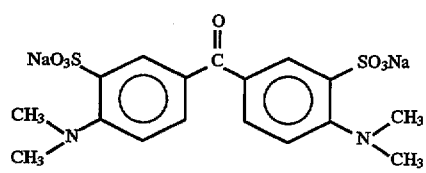
(n)
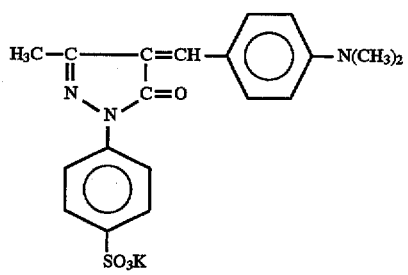
(r)
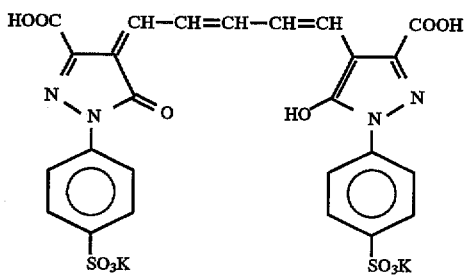
(s)
$C_8F_{17}SO_3Li$ (t)

-continued
Core-shell type vinylidene chloride copolymer (1)

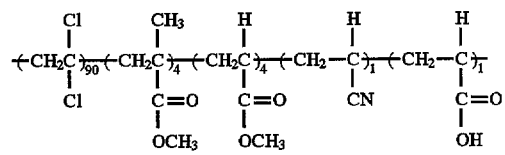

VDC   MMA   MA    AN    AA
Core  : VDC/MMA/MA   (80% by weight)
Shell : VDC/AN/AA    (20% by weight)
Average particle size: 70 nm

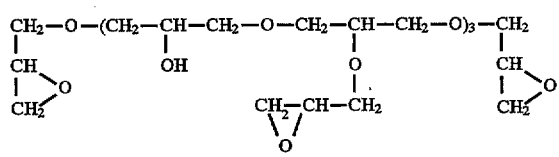 (u)

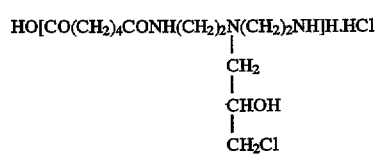 (v)

3) Processing:

The coated sample was exposed to light through an optical wedge using a printer P-627FM manufactured by Dainippon Screen Mfg. Co., Ltd., and processed by means of an automatic processor FG-680AG manufactured by Fuji Photo Film Co., Ltd. using developer A described in Example 1 at 38° C. for 20 seconds, fixed with the same fixing solution as used in Example 1, washed, and dried.

The processed sample was evaluated in terms of image contrast and preservability in the same manner as in Example 1. The results obtained are shown in Table 3 below.

TABLE 3

| Run No. | Nucleating Agent Kind | Amount (mol/m²) | γ | Preservability Retention of Nucleating Agent | $\Delta S_{1.5}$ | Remark |
|---|---|---|---|---|---|---|
| 1 | Cpd. A | $3.0 \times 10^{-5}$ | 5.6 | 83 | 0.03 | Comparison |
| 2 | Cpd. B | $3.0 \times 10^{-5}$ | 5.4 | 84 | 0.03 | Comparison |
| 3 | Cpd. C | $3.0 \times 10^{-5}$ | 6.2 | 82 | 0.04 | Comparison |
| 4 | Cpd. D | $3.0 \times 10^{-5}$ | 5.4 | 80 | 0.06 | Comparison |
| 5 | Cpd. E | $5.5 \times 10^{-6}$ | 11.5 | 72 | 0.10 | Comparison |
| 6 | Cpd. F | $5.5 \times 10^{-6}$ | 5.3 | 96 | 0 | Comparison |
| 7 | Cpd. G | $5.5 \times 10^{-6}$ | 5.2 | 98 | 0 | Comparison |
| 8 | Cpd. H | $5.5 \times 10^{-6}$ | 10.6 | 70 | 0.11 | Comparison |
| 9 | Cpd. I | $3.0 \times 10^{-6}$ | 5.7 | 69 | 0.03 | Comparison |
| 10 | I-1 | $5.5 \times 10^{-6}$ | 11.6 | 94 | 0 | Invention |
| 11 | I-2 | $5.5 \times 10^{-6}$ | 10.6 | 93 | 0 | Invention |
| 12 | I-4 | $5.5 \times 10^{-6}$ | 10.8 | 92 | 0.01 | Invention |
| 13 | I-10 | $5.5 \times 10^{-6}$ | 10.9 | 93 | 0 | Invention |
| 14 | I-11 | $5.5 \times 10^{-6}$ | 10.7 | 92 | 0.01 | Invention |
| 15 | I-14 | $5.5 \times 10^{-6}$ | 10.7 | 91 | 0.01 | Invention |
| 16 | I-16 | $5.5 \times 10^{-6}$ | 10.6 | 93 | 0 | Invention |
| 17 | I-18 | $5.5 \times 10^{-6}$ | 10.5 | 91 | 0.01 | Invention |
| 18 | I-21 | $5.5 \times 10^{-6}$ | 9.9 | 91 | 0.01 | Invention |
| 19 | I-27 | $5.5 \times 10^{-6}$ | 11.0 | 93 | 0 | Invention |
| 20 | I-35 | $5.5 \times 10^{-6}$ | 10.9 | 92 | 0.01 | Invention |
| 21 | I-43 | $5.5 \times 10^{-6}$ | 11.0 | 91 | 0.01 | Invention |
| 22 | I-65 | $5.5 \times 10^{-6}$ | 11.6 | 90 | 0.03 | Invention |

The results in Table 3 prove that the nucleating agents according to the invention provide light-sensitive for dot-to-dot work for lighted room processing which exhibit high gamma characteristics and satisfactory preservability.

EXAMPLE 7

Each of the light-sensitive materials prepared in Examples 1 to 6 hereinafter described was processed in the same manner as in the respective Example except for using developer B or C in place of developer A.

| Developer B: | |
|---|---|
| Potassium hydroxide | 35 g |
| Diethylenetriaminepentaacetic acid | 2 g |
| Potassium carbonate | 100 g |
| Potassium bromide | 3 g |
| 5-Methylbenzotriazole | 0.08 g |
| Sodium 2-mercaptobenzimidazole-5-sulfonate | 0.15 g |
| 2,3,5,6,7,8-Hexahydro-2-thioxo-4-(1H)-quinazoline | 0.03 g |
| Sodium metabisulfite | 54 g |
| 4-Hydroxymethyl-4-methyl-1-phenyl-3-pyrazolidone | 0.45 g |
| Hydroquinone | 30 g |
| Sodium erythorbate | 3 g |
| Water to make | 1 l |
| pH | 10.5 |
| Developer C: | |
| Sodium hydroxide | 10.0 g |
| Diethylenetriaminepentaacetic acid | 1.5 g |
| Potassium carbonate | 15.0 g |
| Potassium bromide | 3.0 g |
| 5-Methylbenzotriazole | 0.10 g |
| 1-Phenyl-5-mercaptotetrazole | 0.02 g |
| Potassium sulfite | 10.0 g |
| sodium 2-mercaptobenzimidazole-5-sulfonate | 0.15 g |
| 4-Hydroxymethyl-4-methyl-1-phenyl-3-pyrazolidone | 0.40 g |
| Sodium erythorbate | 30.0 g |
| Water to make | 1 l |
| pH (adjusted with potassium hydroxide) | 10.7 |

Developer B was prepared from a solid preparation as follows. The components constituting developer B were packaged in a bag made of an aluminum-clad plastic film in layers in the order described below, and the bag was evacuated and sealed in a conventional manner.

1st Layer: hydroquinone

2nd Layer: other components

3rd Layer: sodium bisulfite

4th Layer: Potassium carbonate

5th Layer: Potassium hydroxide pellets

The thus processed samples showed the same results as obtained in Examples 1 to 6.

| Developer X: | |
|---|---|
| Sodium sulfite | 30 g |
| Hydroquinone | 10 g |
| 1-Phenyl-4-methyl-4-hydroxymethyl-3-pyrazolidone | 0.75 g |
| Sodium tertiary phosphate | 40 g |
| Sodium hydroxide | 10.7 g |
| 5-Methylbenzotriazole | 0.02 g |
| Water to make | 1 l |

TABLE 4

| Nucleating Agent | Amount (mmol/mol-Ag) | Dmax | Dmin | Remark |
|---|---|---|---|---|
| none | — | 0.07 | 0.07 | Comparison |
| I-1 | 0.004 | 1.63 | 0.06 | Invention |
| I-11 | 0.004 | 1.90 | 0.08 | " |
| I-18 | 0.004 | 1.56 | 0.07 | " |
| Cpd. J* | 0.4 | 1.24 | 0.07 | Comparison |

*Compound J (hereinafter the same):

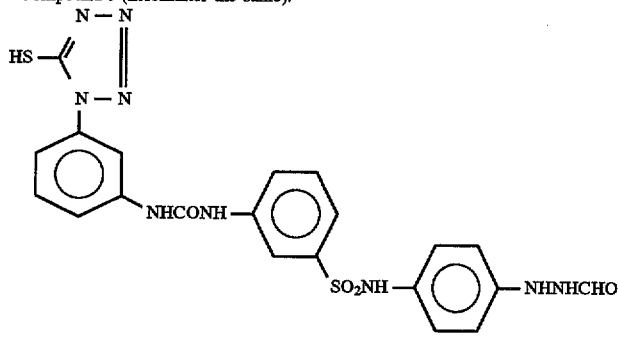

EXAMPLE 8

An internal latent image type direct positive silver bromide emulsion was prepared in the same manner as described in JP-A-60-95533. This emulsion is one having the inside of emulsion grains sulfur- and gold-sensitized and the surface of the grains sulfur-sensitized. The emulsion grains were octahedral grains having a grain size of 1.0 μm.

To the emulsion was added the hydrazine compound of the invention shown in Table 4 below or, for comparison, compound J disclosed in U.S. Pat. No. 3,759,901 to prepare a coating composition. The coating composition was applied to a cellulose acetate film support to give a silver coating weight of 4.4 g/m² and a gelatin coating weight of 4.9 g/m² to form an emulsion layer together with a protective layer (0.8 g/m² of gelatin). The resulting coated sample was exposed to tungsten light (1000 lux) through a continuous wedge for 1/10 sec and processed with developer X having the following formulation (surface developer; pH=13.5). The maximum density (Dmax) and minimum density (Dmin) of the resulting direct reversal image are shown in Table 4.

As can be seen from Table 4, the compounds of the invention exhibit satisfactory reversal performance even when added in a smaller amount than the comparative nucleating agent.

EXAMPLE 9

To the same internal latent image type direct positive emulsion as prepared in Example 8 was added the compound of the invention shown in Table 5 below or comparative compound J, K or M, and a coated sample was prepared in the same manner as in Example 8. The coated sample was imagewise exposed to light under the same exposure conditions as in Example 8 and processed with developer Y (pH=10.7) having a lower pH than developer X. The maximum and minimum densities (Dmax, Dmin) of the resulting direct reversal image are shown in Table 5.

| Developer Y: | |
|---|---|
| Sodium sulfite | 30 g |
| Hydroquinone | 10 g |
| 1-Phenyl-4-methyl-4-hydroxymethyl-3-pyrazolidone | 0.75 g |
| Sodium tertiary phosphate | 40 g |

-continued

| Developer Y: | |
|---|---|
| 5-Methylbenzotriazole | 0.02 g |
| Water to make | 1 l |

TABLE 5

| Nucleating Agent | Amount (mmol/mol-Ag) | Dmax | Dmin | Remark |
|---|---|---|---|---|
| none | — | 0.04 | 0.04 | Comparison |
| I-1 | 0.095 | 1.92 | 0.04 | Invention |
| I-11 | 0.095 | 1.81 | 0.03 | " |
| I-18 | 0.095 | 1.71 | 0.04 | " |
| I-43 | 0.095 | 1.97 | 0.04 | " |
| Cpd. J | 1.0 | 1.54 | 0.04 | Comparison |
| Cpd. K* | 1.0 | 1.77 | 0.05 | " |
| Cpd. M* | 1.0 | 1.72 | 0.04 | " |

*Compound K (U.S. Pat. No. 3,759,901):

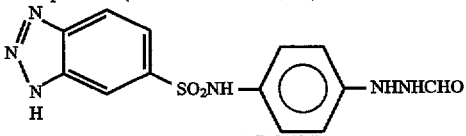

*Compound M (U.S. Pat. No. 3,719,494):

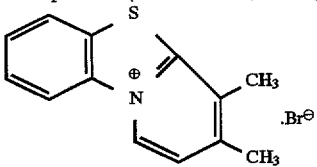

It is seen from Table 5 that the compounds of the invention exhibit satisfactory performance in reversal processing even with a developer having a lower pH when added in a smaller amount than the comparative nucleating agents.

EXAMPLE 10

1) Preparation of Coated Sample:

A paper support having a polyethylene film laminated on both sides thereof (total thickness: 100 μm) was coated with the following 1st to 9th layers on its surface side and with the following 10th to 11th layers on the opposite side thereof to prepare a color light-sensitive material. The polyethylene lamina on the surface side of the support contained 4 g/m$^2$ of titanium oxide as a white pigment and a trace amount (0.003 g/m$^2$) of ultramarine as a blue-tinting dye. The surface side of the support had chromaticity of 88.0, −0.20 and −0.75 as specified according to an L*a*b* colorimetric system.

The composition and coating weight of each layer are as follows. The coating weights are given by g/m$^2$, except that those of silver halide emulsions are given in terms of silver coating weight. Emulsions used except the one used in the 9th layer were prepared in accordance with the method for preparing emulsion EM-1 hereinafter described while varying the temperature to obtain a desired grain size. The emulsion used in the 9th layer was a Lippmann emulsion which had not been subjected to surface chemical sensitization.

| 1st Layer (Antihalation Layer): | |
|---|---|
| Black colloidal silver | 0.10 |
| Color mixing preventive (Cpd-7) | 0.05 |
| Solvent for color mixing preventive (1:1 mixture of Solv-4 and Soly-5) | 0.12 |
| Gelatin | 0.70 |
| 2nd Layer (Intermediate Layer): | |
| Gelatin | 1.40 |
| Dye (Cpd-32) | 0.005 |
| 3rd Layer (Red-sensitive Layer): | |
| Silver bromide emulsion (mean grain size: 0.40 μm; grain size distribution; 10%; octahedral) spectrally sensitized with red sensitizing dyes (5.4 × 10$^{-4}$ mol/mol-Ag of 1:1:1 mixture of ExS-1, 2 and 3) | 0.25 |
| Gelatin | 0.70 |
| Cyan coupler (ExC-1, 2 and 3 = 1:1:0.2) | 0.30 |
| Discoloration preventive (mixture of equal amounts of Cpd-1, 2, 3, 4 and 30) | 0.18 |
| Stain preventive (1:1 mixture of Cpd-5 and 15) | 0.003 |
| Coupler dispersing medium (Cpd-6) | 0.30 |
| Coupler solvent (1:1:1 mixture of Solv-1, 3 and 5) | 0.30 |
| 4th Layer (Intermediate Layer): | |
| Gelatin | 1.00 |
| Color mixing preventive (Cpd-7) | 0.08 |
| Color mixing preventive solvent (1:1 mixture of Solv-4 and 5) | 0.16 |
| Polymer latex (Cpd-8) | 0.10 |
| Dye (Cpd-33) | 0.25 |
| 5th Layer (Green-sensitive Layer): | |
| Silver bromide emulsion (mean grain size: 0.40 μm; grain size distribution; 10%; octahedral) spectrally sensitized with green sensitizing dyes (2.6 × 10$^{-4}$ mol/mol-Ag of ExS-4) | 0.20 |
| Gelatin | 1.00 |
| Magenta coupler (1:1 mixture of ExM-1 and 2) | 0.30 |
| Yellow coupler (ExY-1) | 0.06 |
| Discoloration preventive (mixture of equal amounts of Cpd-9, 26, 30 and 31) | 0.15 |
| Stain preventive (10:7:7:1 mixture of Cpd-10, 11, 12 and 13) | 0.025 |
| Coupler dispersing medium (Cpd-6) | 0.05 |
| Coupler solvent (1:1 mixture of Solv-4 and 6) | 0.60 |
| 6th Layer (Yellow Filter Layer): | |
| Gelatin | 1.00 |
| Dye (Cpd-34) | 0.10 |
| Color mixing preventive (Cpd-7) | 0.08 |
| Color mixing preventive solvent (1:1 mixture of Solv-4 and 5) | 0.16 |
| 7th Layer (Blue-sensitive Layer): | |
| Silver bromide emulsion (mean grain size: 0.60 μm; grain size distribution; 11%; octahedral) spectrally sensitized with blue sensitizing dyes, (3.5 × 10$^{-4}$ mol/mol-Ag of 1:1 mixture of ExS-5 and 6) | 0.32 |
| Gelatin | 0.80 |
| Yellow coupler (1:1 mixture of ExY-2 and 3) | 0.60 |
| Discoloration preventive (Cpd-14) | 0.10 |
| Discoloration preventive (Cpd-30) | 0.05 |
| Stain preventive (1:5 mixture of Cpd-5 and 15) | 0.007 |
| Coupler dispersing medium (Cpd-6) | 0.05 |
| Coupler solvent (Solv-2) | 0.29 |
| 8th Layer (UV Absorbing Layer): | |
| Gelatin | 0.60 |
| UV absorber (1:1:1 mixture of Cpd-2, 4 and 16) | 0.40 |
| Color mixing preventive (1:1 mixture of Cpd-7 and 17) | 0.03 |
| Dispersing medium (Cpd-6) | 0.02 |

| | |
|---|---|
| UV absorber solvent (1:1 mixture of Solv-2 and 7) | 0.08 |
| Irradiation neutralizing dye (10:10:13:15:20 mixture of Cpd-18, 19, 20, 21 and 27) | 0.05 |
| 9th Layer (Protective Layer): | |
| Silver bromide fine particles (AgBr content: 99 mol %; mean particle size: 0.05 μm) | 0.05 |
| Acryl-modified polyvinyl alcohol copolymer (molecular weight: 50,000) | 0.01 |
| 1:1 Mixture of polymethyl methacrylate particles (average particle size: 2.4 μm) and silicon oxide (average particle size: 5 μm) | 0.05 |
| Gelatin | 0.05 |
| Gelatin hardening agent (1:1 mixture of H-1 and 2) | 0.18 |
| 10th Layer (Backing Layer): | |
| Gelatin | 2.50 |
| UV absorber (1:1:1 mixture of Cpd-2, 4 and 16) | 0.50 |
| Dye (mixture of equal amounts of Cpd-18, 19, 20, 21 and 27) | 0.06 |
| 11th Layer (Back Protective Layer): | |
| 1:1 Mixture of polymethyl methacrylate particles (average particle size: 2.4 μm) and silicon oxide (average particle size: 5 μm) | 0.05 |
| Gelatin | 2.00 |
| Gelatin hardening agent (1:1 mixture of H-1 and 2) | 0.14 |

Preparation of Emulsion EM-1:

A potassium bromide aqueous solution and a silver nitrate aqueous solution were simultaneously added to a gelatin aqueous solution while vigorously stirring at 65° C. over a 15-minute period to prepare octahedral silver bromide grains having a mean grain size of 0.23 μm. To the emulsion was added 0.3 g/mol-Ag of 3,4-dimethyl-1,3-thiazoline-2-thione. The resulting emulsion was chemically sensitized by successively adding 6 mg/mol-Ag of sodium thiosulfate and 7 mg/mol-Ag of chloroauric acid (tetrahydrate) followed by heating at 75° C. for 80 minutes. The resulting emulsion grains were allowed to grow as core in the same precipitation environment as above to finally obtain an octahedral monodispersed core/shell silver bromide emulsion having a mean grain size of 0.4 μm. The coefficient of grain size distribution was about 10%. The emulsion was chemically sensitized by adding 1.5 mg/mol-Ag of sodium thiosulfate and 1.5 mg/mol-Ag of chloroauric acid (tetrahydrate) followed by heating at 60° C. for 60 minutes to obtain an internal latent image type silver halide emulsion.

To each of the light-sensitive layers was added ExZK-1 as a nucleating agent in the amount shown in Table 6 below. Cpd-22, Cpd-28, and Cpd-29 were added to the red-sensitive layer, the green-sensitive layer, and the blue-sensitive layer, respectively, in an amount of $3.2 \times 10^{-4}$ mmol/m$^2$, $2.9 \times 10^{-4}$ mmol/m$^2$, and $2.6 \times 10^{-4}$ mmol/m$^2$, respectively. To each layer were further added Alkanol XC (produced by E. I. Du Pont) and a sodium alkylbenzenesulfonate as dispersing aid, and a succinic ester and Magefac F-120 (produced by Dainippon Ink and Chemicals, Inc.) as coating aid. A stabilizer (a mixture of equal amounts of Cpd-23, Cpd-24, and Cpd-25) was added to each layer containing silver halide or colloidal silver. The thus prepared coated sample is designated sample 101. The compounds used in sample 101 are shown below.

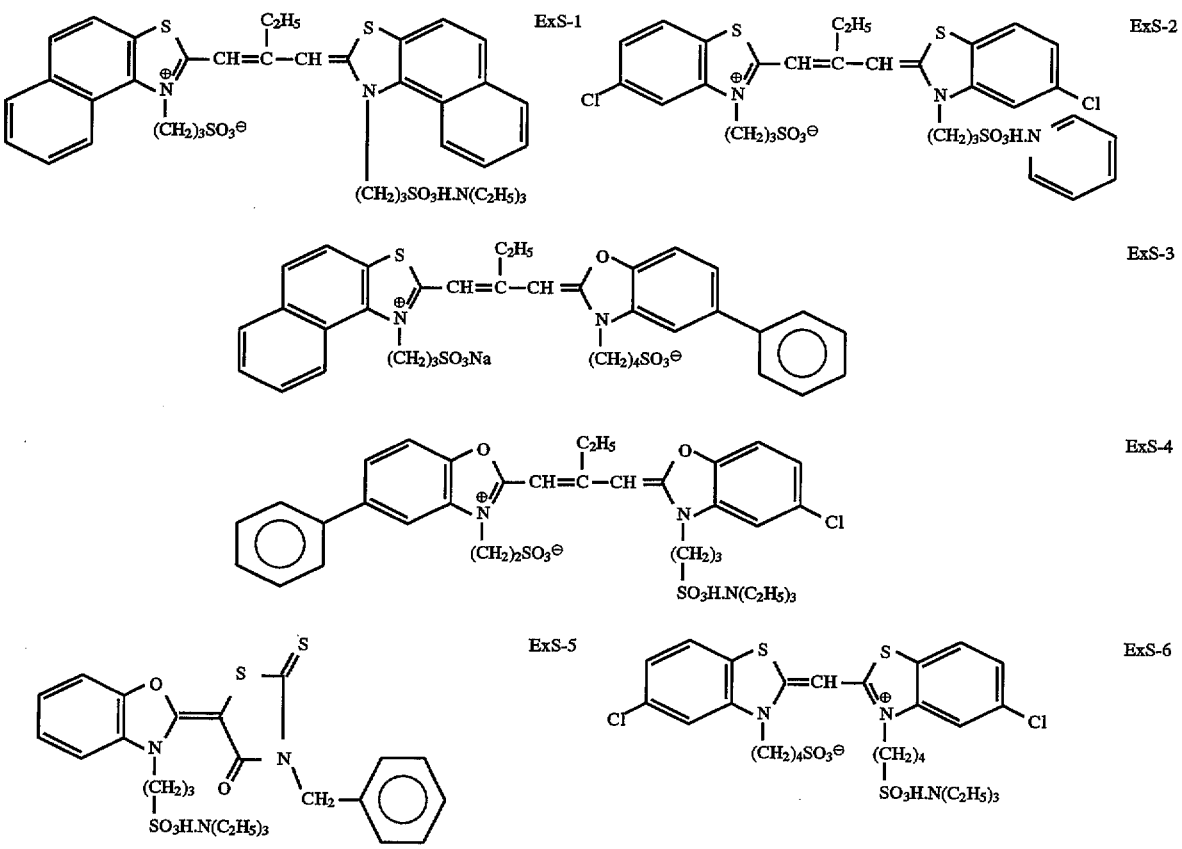

-continued
Cpd-1
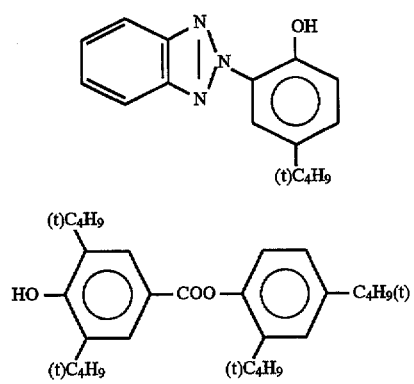
Cpd-2
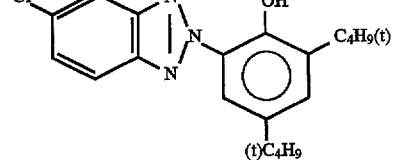
Cpd-3
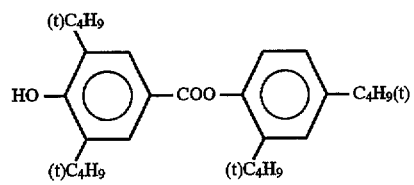
Cpd-4
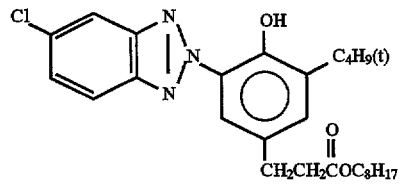
Cpd-5
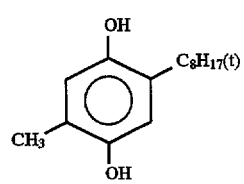
Cpd-6
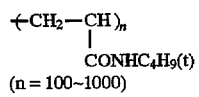
(n = 100~1000)
Cpd-7
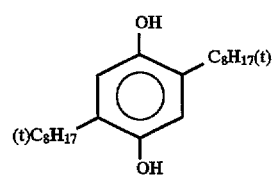
Cpd-8
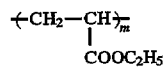
Cpd-9
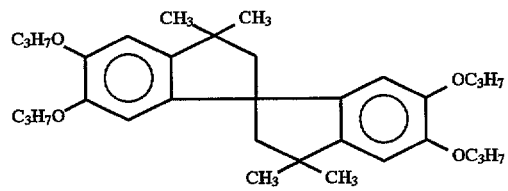
Cpd-10
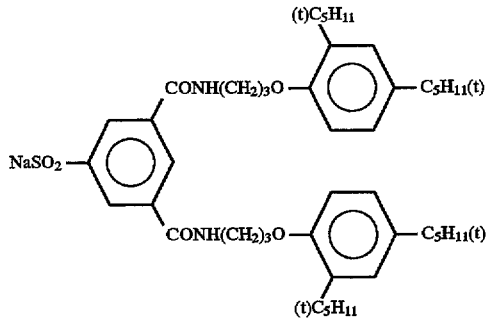
Cpd-11
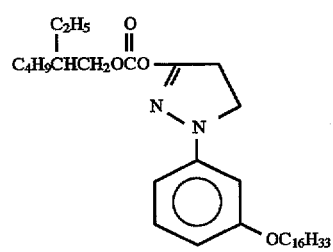
Cpd-12
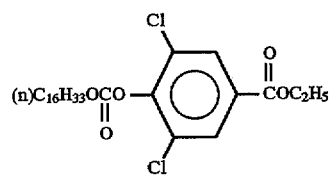
Cpd-13
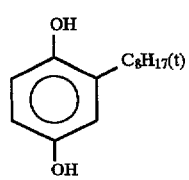
Cpd-14
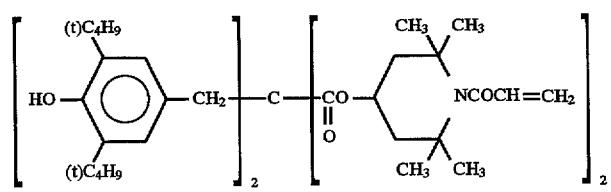

-continued
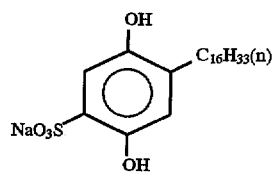
Cpd-15
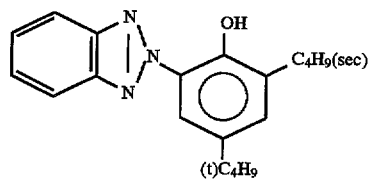
Cpd-16
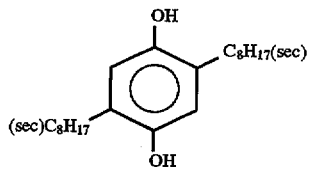
Cpd-17
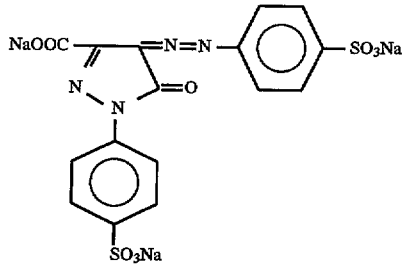
Cpd-18
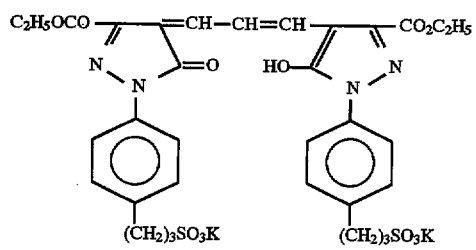
Cpd-19
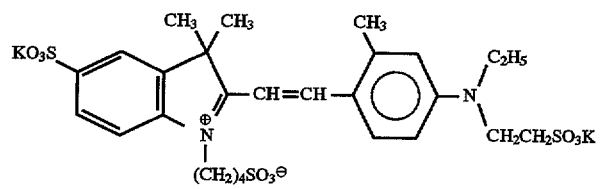
Cpd-20
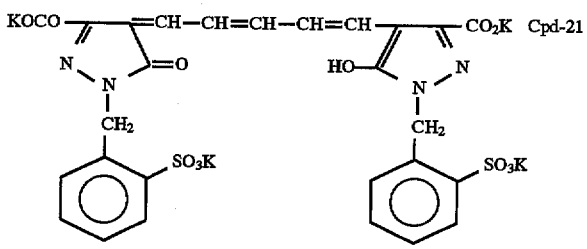
Cpd-21
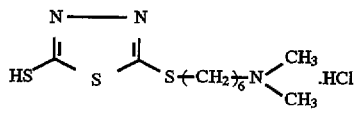
Cpd-22
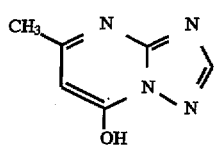
Cpd-23
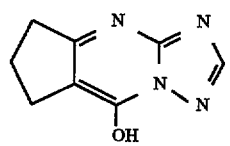
Cpd-24
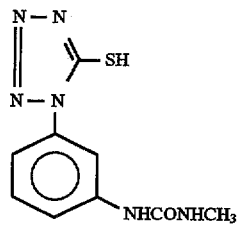
Cpd-25
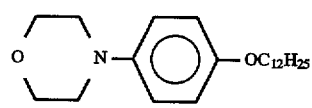
Cpd-26

-continued
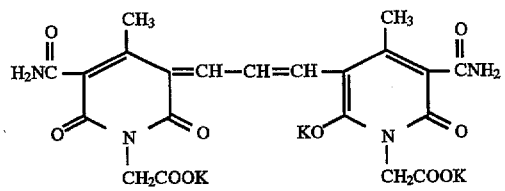 Cpd-27
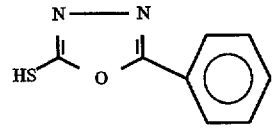 Cpd-28
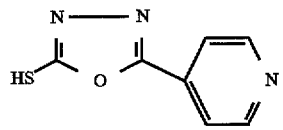 Cpd-29
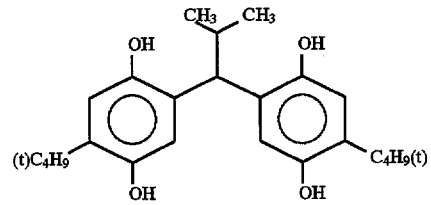 Cpd-30
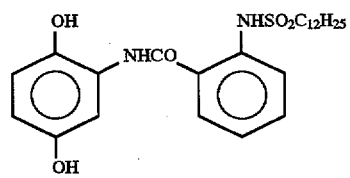 Cpd-31
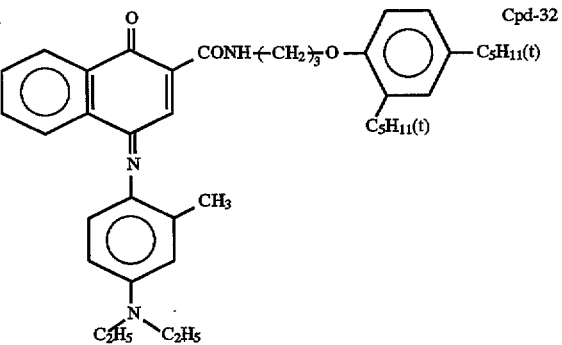 Cpd-32
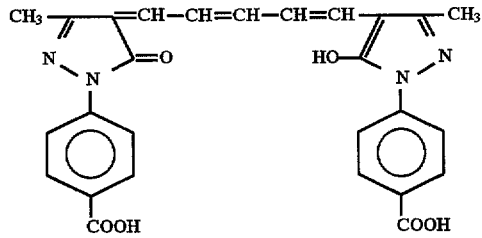 Cpd-33
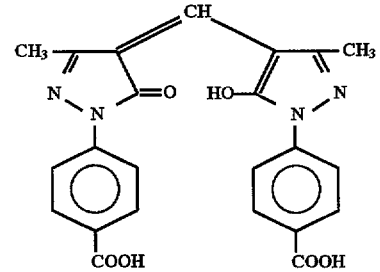 Cpd-34
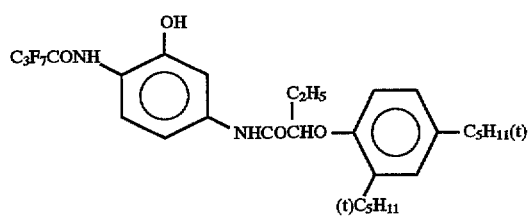 ExC-1
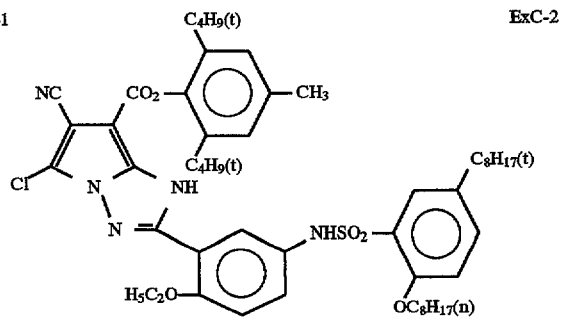 ExC-2
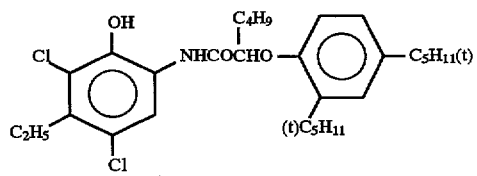 ExC-3

-continued
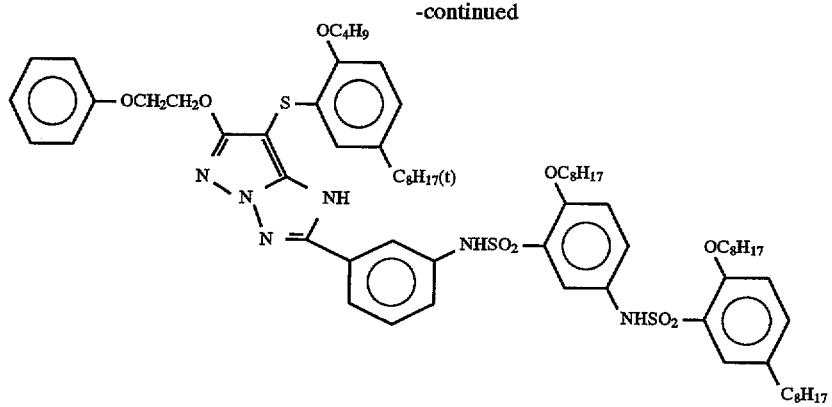
ExM-1
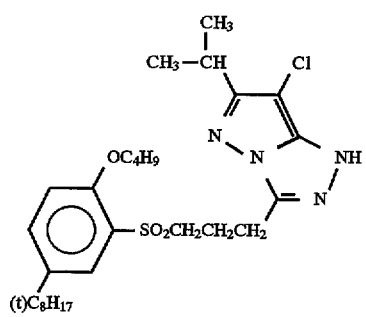
ExM-2
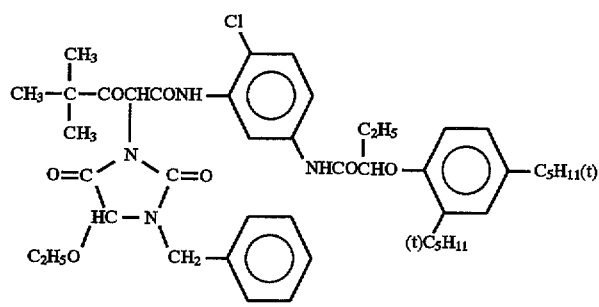
ExY-1
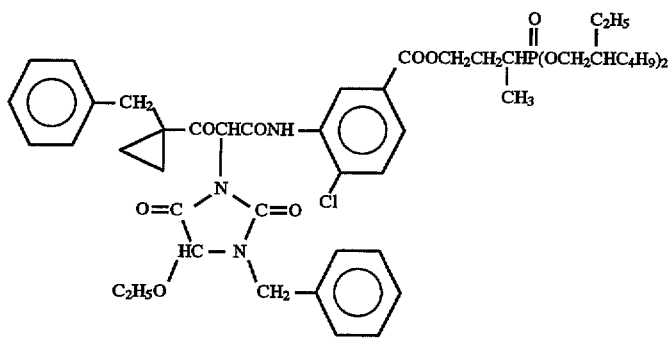
ExY-2
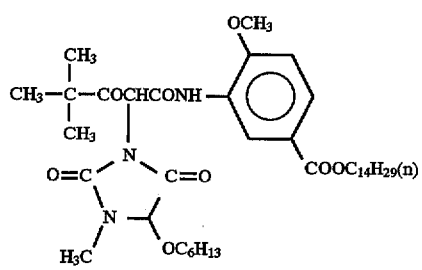
ExY-3
Di(2-ethylhexyl) sebacate     Solv-1:
Trinonyl phosphate     Solv-2:     Di(3-methylhexyl) phthalate     Solv-3:

| | |
|---|---|
| Tricresyl phosphate | Solv-4: |
| Trioctyl phosphate | Solv-6: |
| 1,2-Bis(vinylsulfonylacetamido)ethane | H-1: |
| 7-(3-Ethoxythiocarbonylaminobenzamido)-9-methyl-10-propargyl-1,2,3,4-tetrahydroacridinium trifluoromethanesulfonate | ExZK-1: |
| Dibutyl phthalate | Solv-5: |
| Di(2-ethylhexyl)phthalate | Solv-7: |
| Sodium 4,6-Dichloro-2-hydroxy-1,3,5-triazine | H-2: |

Samples 102 to 105 were prepared in the same manner as for sample 101 except for replacing the nucleating agent ExZK-1 with ExZK-2 or the compound of the invention as shown in Table 6 below.

Each of samples 101 to 105 was imagewise exposed to light using Fine Checker 850H manufactured by Fuji Photo Film Co., Ltd. and continuously processed according to the following procedure until the cumulative amount of the replenisher reached 3 times the respective tank capacity.

| Processing Step | Time (sec) | Temp. (°C.) | Tank Capacity (l) | Rate of Replenishment (ml/m²) |
|---|---|---|---|---|
| Color development | 135 | 38 | 28 | 240 |
| Blix | 40 | 35 | 11 | 320 |
| Washing (1) | 40 | 35 | 7 | — |
| Washing (2) | 40 | 35 | 7 | 320 |
| Drying | 30 | 80 | | |

Replenishment with washing water was a countercurrent replenishing system, in which the washing bath (2) was replenished, and the overflow from the washing bath (2) was led to the washing bath (1). The carry-over of each processing solution to the next bath was 35 ml/m².

Each processing solution used had the following formulation.

| | Tank Solution | Replenisher |
|---|---|---|
| Developer: | | |
| D-Sorbitol | 0.15 g | 0.20 g |
| Sodium naphthalenesulfonate-formalin condensate | 0.15 g | 0.20 g |
| Pentasodium nitrilotris(methanephosphonate) | 1.8 g | 1.8 g |
| Diethylenetriaminepentaacetic acid | 0.5 g | 0.5 g |
| 1-Hydroxyethylidene-1,1-diphosphonic acid | 0.15 g | 0.15 g |
| Diethylene glycol | 12.0 ml | 16.0 ml |
| Benzyl alcohol | 14.0 ml | 18.5 ml |
| Potassium bromide | 0.70 g | — |
| Benzotriazole | 0.005 g | 0.007 g |
| Sodium sulfite | 5.6 g | 7.4 g |
| Hydroxylamine hemisulfate | 4.5 g | 6.0 g |
| Triethanolamine | 6.0 g | 8.0 g |
| 4-[N-Ethyl-N-(β-hydroxyethyl)amino]-aniline sulfate hemihydrate | 4.2 g | 5.6 g |
| Potassium carbonate | 30.0 g | 25.0 g |
| Fluorescent brightening agent (diaminostilbene type) | 1.3 g | 1.7 g |
| Water to make | 1000 ml | 1000 ml |
| pH (25° C.) (adjusted with potassium hydroxide or sulfuric acid) | 10.25 | 10.75 |
| Blix Bath (common to tank solution and replenisher): | | |
| Disodium ethylenediaminetetraacetate dehydrate | 4.0 g | |
| Ammonium (ethylenediaminetetra- | 55.0 g | |

| | Tank Solution | Replenisher |
|---|---|---|
| acetato)iron (III) dehydrate | | |
| Ammonium thiosulfate (750 g/l) | 168 ml | |
| Sodium p-toluenesulfinate | 30.0 g | |
| Ammonium sulfite | 35.0 g | |
| 3-Mercapto-1,2,4-triazole | 0.5 g | |
| Ammonium nitrate | 10.0 g | |
| Water to make | 1000 ml | |
| pH (25° C.) (adjusted with aqueous ammonia or acetic acid) | 6.20 | |
| Wash Bath (common to tank solution and replenisher): | | |
| Sodium chloroisocyanurate | 0.02 g | |
| Deionized water (conductivity: not higher than 5 µs/cm) | 1000 ml | |
| pH | 6.5 | |

The maximum density (Dmax) and minimum density (Dmin) of the resulting image are shown in Table 6 below.

TABLE 6

| Sample No. | Nucleating Agent | | | | | |
|---|---|---|---|---|---|---|
| | Kind | Layer* | Amount (mmol/m²) | Dmax | Dmin | Remarks |
| 101 | ExZK-1 | R | $1.3 \times 10^{-6}$ | 1.75 | 0.30 | Comparison |
| | | G | $1.3 \times 10^{-6}$ | 1.91 | 0.20 | |
| | | B | $0.72 \times 10^{-6}$ | 1.52 | 0.25 | |
| 102 | ExZK-2** | R | $1.5 \times 10^{-5}$ | 1.85 | 0.24 | Comparison |
| | | G | $1.5 \times 10^{-5}$ | 2.01 | 0.22 | |
| | | B | $1.0 \times 10^{-5}$ | 1.75 | 0.24 | |
| 103 | I-1 | R | $1.0 \times 10^{-6}$ | 2.11 | 0.20 | Invention |
| | | G | $1.0 \times 10^{-6}$ | 2.42 | 0.13 | |
| | | B | $0.70 \times 10^{-6}$ | 2.11 | 0.15 | |
| 104 | I-18 | R | $1.0 \times 10^{-6}$ | 2.10 | 0.21 | Invention |
| | | G | $1.0 \times 10^{-6}$ | 2.21 | 0.12 | |
| | | B | $0.85 \times 10^{-6}$ | 2.05 | 0.16 | |
| 105 | I-43 | R | $1.2 \times 10^{-6}$ | 2.24 | 0.20 | Invention |
| | | G | $1.2 \times 10^{-6}$ | 2.40 | 0.11 | |
| | | B | $0.75 \times 10^{-6}$ | 2.00 | 0.12 | |

*R: red-sensitive layer
G: green-sensitive layer
B: blue-sensitive layer
**ExZK-2:

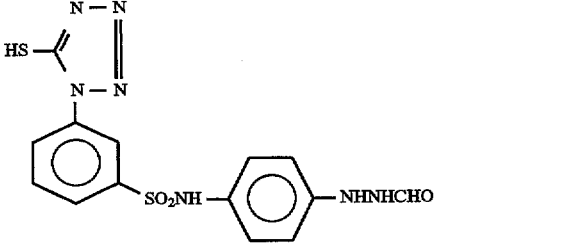

It is seen from Table 6 that the nucleating agents of the invention, as used in multilayer color direct positive light-sensitive materials, exhibit satisfactory performance in reversal processing at reduced amounts.

EXAMPLE 11

The same procedure as in Example 1 was repeated, except for changing the hydrazide compound as shown in Table 7 below. The results of evaluation are shown in Table 7.

formula (2) according to the invention provided light-sensitive materials for helium-neon laser scanning which exhibit high gamma characteristics and satisfactory preservability.

EXAMPLE 13

The alteration effected in Example 3 on the light-sensitive materials of Example 2 was made on the light-sensitive

TABLE 7

| Run No. | Nucleating Agent Kind | Nucleating Agent Amount (mol/m$^2$) | $\gamma$ | Preservability Retention of Nucleating Agent | $\Delta S_{1.5}$ | Remark |
| --- | --- | --- | --- | --- | --- | --- |
| 1 | Cpd. A | $1.0 \times 10^{-5}$ | 7.2 | 83 | 0.05 | Comparison |
| 2 | Cpd. B | " | 7.4 | 83 | 0.05 | " |
| 3 | Cpd. C | " | 8.6 | 82 | 0.06 | " |
| 4 | Cpd. D | " | 7.2 | 80 | 0.07 | " |
| 5 | Cpd. 2E* | $4.0 \times 10^{-6}$ | 16.2 | 61 | 0.16 | " |
| 6 | Cpd. 2F* | " | 7.2 | 95 | 0 | " |
| 7 | Cpd. 2G* | $6.0 \times 10^{-6}$ | 16.0 | 52 | 0.23 | " |
| 8 | Cpd. 2H* | " | 7.6 | 98 | 0 | " |
| 9 | 2-1 | $4.0 \times 10^{-6}$ | 16.2 | 94 | 0 | Invention |
| 10 | 2-3 | " | 15.3 | 93 | 0 | " |
| 11 | 2-4 | " | 16.1 | 94 | 0.01 | " |
| 12 | 2-6 | " | 16.7 | 92 | 0 | " |
| 13 | 2-7 | $5.0 \times 10^{-6}$ | 16.7 | 92 | 0.01 | " |
| 14 | 2-13 | $4.0 \times 10^{-6}$ | 15.8 | 91 | 0.01 | " |
| 15 | 2-14 | " | 15.0 | 94 | 0 | " |
| 16 | 2-31 | $6.0 \times 10^{-6}$ | 16.6 | 91 | 0.02 | " |
| 17 | 2-47 | " | 15.8 | 91 | 0.02 | " |
| 18 | 2-50 | $4.0 \times 10^{-6}$ | 15.0 | 93 | 0 | " |

*Comparative Compound 2E:

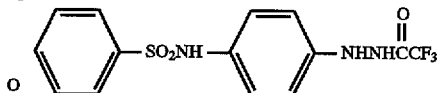

*Comparative Compound 2F:

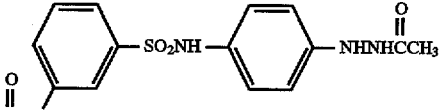

*Comparative Compound 2G:

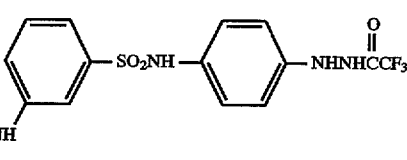

*Comparative Compound 2H:

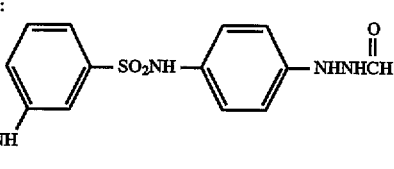

The results in Table 7 prove that the hydrazide compounds of formula (2) according to the invention produce excellent effects.

EXAMPLE 12

The alteration effected in Example 2 on the light-sensitive materials of Example 1 was made on the light-sensitive materials of Example 11. The hydrazide compounds of formula (2) according to the invention provided light-sensitive materials of Example 12. The hydrazide compounds of formula (2) according to the invention provided light-sensitive materials for semiconductor laser scanning which exhibit high gamma characteristics and satisfactory preservability.

EXAMPLE 14

Light-sensitive materials were prepared in the same manner as in Example 4, except for changing the hydrazide compound as shown in Table 8 below. The results of evaluation are shown in the Table.

TABLE 8

| Run No. | Nucleating Agent | | Preservability | | | |
|---|---|---|---|---|---|---|
| | Kind | Amount (mol/m²) | γ | Retention of Nucleating Agent | ΔS$_{1.5}$ | Remark |
| 1 | Cpd. A | $1.0 \times 10^{-5}$ | 7.2 | 83 | 0.06 | Comparison |
| 2 | Cpd. B | $1.0 \times 10^{-5}$ | 7.4 | 83 | 0.06 | Comparison |
| 3 | Cpd. C | $1.0 \times 10^{-5}$ | 8.6 | 82 | 0.07 | Comparison |
| 4 | cpd. D | $1.0 \times 10^{-5}$ | 7.2 | 80 | 0.06 | Comparison |
| 5 | Cpd. 2E | $4.0 \times 10^{-6}$ | 16.2 | 61 | 0.18 | Comparison |
| 6 | Cpd. 2F | $4.0 \times 10^{-6}$ | 7.2 | 95 | 0 | Comparison |
| 7 | Cpd. 2G | $6.0 \times 10^{-6}$ | 16.0 | 52 | 0.29 | Comparison |
| 8 | Cpd. 2H | $6.0 \times 10^{-6}$ | 7.6 | 98 | 0 | Comparison |
| 9 | 2-1 | $4.0 \times 10^{-6}$ | 16.7 | 94 | 0 | Invention |
| 10 | 2-3 | $4.0 \times 10^{-6}$ | 15.6 | 93 | 0 | Invention |
| 11 | 2-4 | $4.0 \times 10^{-6}$ | 16.1 | 92 | 0.02 | Invention |
| 12 | 2-6 | $4.0 \times 10^{-6}$ | 16.6 | 94 | 0 | Invention |
| 13 | 2-7 | $5.0 \times 10^{-6}$ | 16.4 | 92 | 0.01 | Invention |
| 14 | 2-13 | $4.0 \times 10^{-6}$ | 16.1 | 91 | 0.02 | Invention |
| 15 | 2-14 | $4.0 \times 10^{-6}$ | 15.2 | 94 | 0 | Invention |
| 16 | 2-31 | $6.0 \times 10^{-6}$ | 16.4 | 91 | 0.02 | Invention |
| 17 | 2-47 | $6.0 \times 10^{-6}$ | 15.8 | 91 | 0.02 | Invention |
| 18 | 2-50 | $4.0 \times 10^{-6}$ | 15.5 | 93 | 0 | Invention |

It can be seen from Table 8 that the hydrazide compounds of formula (2) according to the invention provide light-sensitive materials for photographing which exhibit high gamma characteristics and satisfactory preservability.

EXAMPLE 15

Coated samples were prepared by basically following the formulation described in Example 5 of JP-A-7-43867 and using the hydrazide compound of formula (2) according to the present invention. The coated samples were processed and evaluated in the same manner as in Example 4. As a result, the light-sensitive materials for photographing were proved to exhibit high gamma characteristics and satisfactory preservability.

EXAMPLE 16

The same procedure as in Example 6 was repeated, except for changing the hydrazide compound as shown in Table 9 below. The results of evaluation are shown in the Table.

TABLE 9

| Run No. | Nucleating Agent | | Preservability | | | |
|---|---|---|---|---|---|---|
| | Kind | Amount (mol/m²) | γ | Retention of Nucleating Agent | ΔS$_{1.5}$ | Remark |
| 1 | Cpd. A | $3.0 \times 10^{-5}$ | 5.6 | 83 | 0.03 | Comparison |
| 2 | Cpd. B | $3.0 \times 10^{-5}$ | 5.4 | 84 | 0.03 | Comparison |
| 3 | Cpd. C | $3.0 \times 10^{-5}$ | 6.2 | 82 | 0.04 | Comparison |
| 4 | cpd. D | $3.0 \times 10^{-5}$ | 5.4 | 80 | 0.06 | Comparison |
| 5 | Cpd. 2E | $8.0 \times 10^{-6}$ | 11.2 | 61 | 0.18 | Comparison |
| 6 | Cpd. 2F | $8.0 \times 10^{-6}$ | 5.6 | 95 | 0 | Comparison |
| 7 | Cpd. 2G | $1.5 \times 10^{-5}$ | 11.0 | 52 | 0.29 | Comparison |
| 8 | Cpd. 2H | $1.8 \times 10^{-5}$ | 5.6 | 98 | 0 | Comparison |
| 9 | 2-1 | $8.0 \times 10^{-6}$ | 11.1 | 94 | 0 | Invention |
| 10 | 2-3 | $8.0 \times 10^{-6}$ | 10.9 | 93 | 0 | Invention |
| 11 | 2-4 | $8.0 \times 10^{-6}$ | 10.6 | 92 | 0.02 | Invention |
| 12 | 2-6 | $8.0 \times 10^{-6}$ | 10.7 | 94 | 0 | Invention |
| 13 | 2-7 | $1.0 \times 10^{-5}$ | 11.1 | 92 | 0.01 | Invention |
| 14 | 2-13 | $8.0 \times 10^{-6}$ | 10.7 | 91 | 0.02 | Invention |
| 15 | 2-14 | $8.0 \times 10^{-6}$ | 10.6 | 94 | 0 | Invention |
| 16 | 2-31 | $1.2 \times 10^{-5}$ | 9.6 | 91 | 0.02 | Invention |
| 17 | 2-47 | $1.2 \times 10^{-5}$ | 9.8 | 91 | 0.02 | Invention |
| 18 | 2-50 | $8.0 \times 10^{-6}$ | 10.8 | 93 | 0 | Invention |

It is seen from Table 9 that the hydrazide compounds of formula (2) according to the invention provide light-sensitive material for dot-to-dot work to be processed in a lighted room which exhibit high gamma characteristics and satisfactory preservability.

EXAMPLE 17

The light-sensitive materials prepared in Example 11 to 16 were processed in the same manner as in the respective Example except for replacing developer A with developer B or C described in Example 7. As a result, it was proved that satisfactory results can be obtained even with developers B and C as well.

EXAMPLE 18

The same procedure as in Example 8 was repeated, except for changing the hydrazide compound as shown in Table 10 below. The results of evaluation are shown in Table 10.

TABLE 10

| Nucleating Agent | Amount (mmol/mol-Ag) | Dmax | Dmin | Remark |
|---|---|---|---|---|
| none | — | 0.07 | 0.07 | Comparison |
| 2-1 | 0.05 | 1.82 | 0.06 | Invention |
| 2-13 | 0.05 | 1.61 | 0.05 | Invention |
| 2-31 | 0.05 | 1.71 | 0.07 | Invenetion |
| Cpd. J | 0.4 | 1.24 | 0.07 | Comparison |

It can be seen from Table 10 that the hydrazide compounds of formula (2) exhibit satisfactory performance in reversal processing when used in a smaller amount than the comparative compound.

EXAMPLE 19

The same procedure as in Example 9 was repeated, except for changing the hydrazide compound as shown in Table 11 below. The results of evaluation are shown in Table 11.

TABLE 11

| Nucleating Agent | Amount (mmol/mol-Ag) | Dmax | Dmin | Remark |
|---|---|---|---|---|
| none | — | 0.04 | 0.04 | Comparison |
| 2-1 | 0.095 | 1.91 | 0.0 | Invention |
| 2-4 | 0.095 | 1.83 | 0.03 | Invention |
| 2-14 | 0.095 | 1.72 | 0.02 | Invention |
| 2-47 | 0.095 | 1.91 | 0.04 | Invention |
| Cpd. J | 1.0 | 1.54 | 0.04 | Comparison |
| Cpd. K | 1.0 | 1.77 | 0.05 | Comparison |
| Cpd. M | 1.0 | 1.72 | 0.04 | Comparison |

It can be seen from Table 11 that the hydrazide compounds of formula (2) exhibit satisfactory performance in reversal processing even with a developer having a low pH when added in a smaller amount than the comparative nucleating agents.

EXAMPLE 20

The same procedure as in Example 10 was repeated except for changing the hydrazide compound as shown in Table 12 below. The results obtained are shown in the Table.

TABLE 12

| Sample No. | Kind | Layer | Amount (mmol/m$^2$) | Dmax | Dmin | Remarks |
|---|---|---|---|---|---|---|
| 101 | ExZK-1 | R | $1.3 \times 10^{-6}$ | 1.75 | 0.30 | Comparison |
|  |  | G | $1.3 \times 10^{-6}$ | 1.91 | 0.20 |  |
|  |  | B | $0.72 \times 10^{-6}$ | 1.52 | 0.25 |  |
| 102 | ExZK-2 | R | $1.5 \times 10^{-5}$ | 1.85 | 0.24 | Comparison |
|  |  | G | $1.5 \times 10^{-5}$ | 2.0 | 0.22 |  |
|  |  | B | $1.0 \times 10^{-5}$ | 1.75 | 0.24 |  |
| 103 | 2-1 | R | $5.0 \times 10^{-6}$ | 2.10 | 0.20 | Invention |
|  |  | G | $5.0 \times 10^{-6}$ | 2.41 | 0.17 |  |
|  |  | B | $0.90 \times 10^{-6}$ | 2.12 | 0.18 |  |

TABLE 12-continued

| Sample No. | Kind | Layer | Amount (mmol/m$^2$) | Dmax | Dmin | Remarks |
|---|---|---|---|---|---|---|
| 104 | 2-7 | R | $5.0 \times 10^{-6}$ | 2.41 | 0.21 | Invention |
|  |  | G | $5.0 \times 10^{-6}$ | 2.73 | 0.19 |  |
|  |  | B | $0.75 \times 10^{-6}$ | 2.32 | 0.12 |  |
| 105 | 2-31 | R | $5.0 \times 10^{-6}$ | 2.04 | 0.20 | Invention |
|  |  | G | $5.0 \times 10^{-6}$ | 2.23 | 0.11 |  |
|  |  | B | $0.75 \times 10^{-6}$ | 2.00 | 0.13 |  |

It is seen from Table 12 that the hydrazide compounds of formula (2), as used in multilayer color direct positive light-sensitive materials, exhibit satisfactory performance in reversal processing at reduced amounts.

EXAMPLE 21

The same procedure as in Example 1 was repeated except for changing the hydrazide compound as shown in Table 13 below. The results obtained are shown in Table 13.

TABLE 13

| | Nucleating Agent | | | Preservability | | |
|---|---|---|---|---|---|---|
| Run No. | Kind | Amount (mol/m$^2$) | $\gamma$ | Retention of Nucleating Agent | $\Delta S_{1.5}$ | Remark |
| 1 | Cpd. A | $1.0 \times 10^{-5}$ | 7.2 | 83 | 0.05 | Comparison |
| 2 | Cpd. B | " | 7.4 | 83 | 0.05 | " |
| 3 | Cpd. C | " | 8.6 | 82 | 0.06 | " |
| 4 | Cpd. D | " | 7.2 | 80 | 0.07 | " |
| 5 | Cpd. 3E* | " | 14.3 | 72 | 0.10 | " |
| 6 | Cpd. 3F* | " | 7.2 | 95 | 0 | " |
| 7 | Cpd. 3G* | " | 13.2 | 70 | 0.11 | " |
| 8 | 3-1 | " | 15.1 | 94 | 0 | Invention |
| 9 | 3-2 | " | 14.8 | 93 | 0 | " |
| 10 | 3-5 | " | 14.6 | 92 | 0.01 | " |
| 11 | 3-9 | " | 14.9 | 94 | 0 | " |
| 12 | 3-14 | " | 14.7 | 92 | 0.01 | " |
| 13 | 3-17 | " | 14.0 | 91 | 0.02 | " |
| 14 | 3-22 | " | 15.0 | 94 | 0 | " |
| 15 | 3-24 | " | 15.0 | 92 | 0.02 | " |
| 16 | 3-28 | " | 15.1 | 92 | 0.01 | " |
| 17 | 3-30 | " | 14.4 | 93 | 0 | " |
| 18 | 3-32 | $5.0 \times 10^{-6}$ | 15.3 | 92 | 0.02 | " |
| 19 | 3-35 | $1.0 \times 10^{-6}$ | 14.7 | 92 | 0.02 | " |
| 20 | 3-36 | " | 13.4 | 90 | 0.03 | " |

*Comparative Compound 3E:

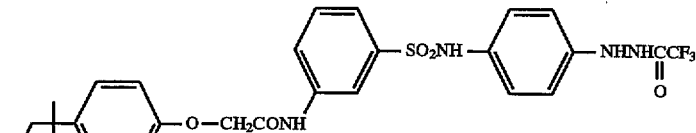

*Comparative Compound 3F:

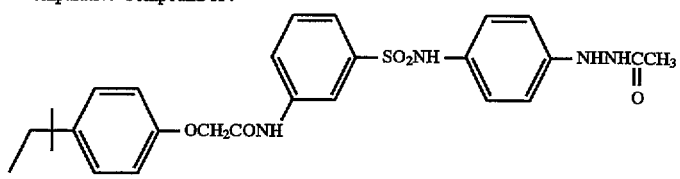

TABLE 13-continued

*Comparative Compound 3G:

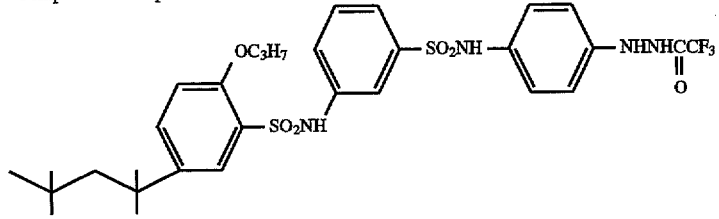

It is seen from Table 13 that the hydrazide compounds of formula (3) according to the invention show excellent effects.

EXAMPLE 22

The alteration effected in Example 2 on the light-sensitive materials of Example 1 was made on the light-sensitive materials of Example 11. As a result, the hydrazide compounds of formula (3) according to the invention provided light-sensitive materials for helium-neon laser scanning which exhibit high gamma characteristics and satisfactory preservability.

EXAMPLE 23

The alteration effected in Example 3 on the light-sensitive materials of Example 2 was made on the light-sensitive materials of Example 12. As a result, the hydrazide compounds of formula (3) according to the invention provided light-sensitive materials for semiconductor laser scanning which exhibit high gamma characteristics and satisfactory preservability.

EXAMPLE 24

The same procedure as in Example 4 was repeated except for changing the hydrazide compound as shown in Table 14 below. The results obtained are shown in Table 14.

TABLE 14

| Run No. | Nucleating Agent Kind | Amount (mol/m$^2$) | $\gamma$ | Preservability Retention of Nucleating Agent | $\Delta S_{1.5}$ | Remark |
|---|---|---|---|---|---|---|
| 1 | Cpd. A | $1.0 \times 10^{-5}$ | 7.3 | 83 | 0.06 | Comparison |
| 2 | Cpd. B | $1.0 \times 10^{-5}$ | 7.4 | 83 | 0.06 | Comparison |
| 3 | Cpd. C | $1.0 \times 10^{-5}$ | 8.5 | 82 | 0.06 | Comparison |
| 4 | Cpd. D | $1.0 \times 10^{-5}$ | 7.3 | 80 | 0.08 | Comparison |
| 5 | Cpd. 3E | $1.0 \times 10^{-5}$ | 13.8 | 71 | 0.12 | Comparison |
| 6 | Cpd. 3F | $1.0 \times 10^{-5}$ | 7.2 | 95 | 0 | Comparison |
| 7 | Cpd. 3G | $1.0 \times 10^{-5}$ | 13.0 | 68 | 0.13 | Comparison |
| 8 | 3-1 | $1.0 \times 10^{-5}$ | 13.9 | 94 | 0 | Comparison |
| 9 | 3-2 | $1.0 \times 10^{-5}$ | 13.6 | 93 | 0 | Comparison |
| 10 | 3-5 | $1.0 \times 10^{-5}$ | 13.2 | 92 | 0.01 | Comparison |
| 11 | 3-9 | $1.0 \times 10^{-5}$ | 12.9 | 94 | 0 | Comparison |
| 12 | 3-14 | $1.0 \times 10^{-5}$ | 13.1 | 92 | 0.01 | Comparison |
| 13 | 3-17 | $1.0 \times 10^{-5}$ | 12.6 | 89 | 0.04 | Comparison |
| 14 | 3-22 | $1.0 \times 10^{-5}$ | 13.2 | 94 | 0 | Comparison |
| 15 | 3-24 | $1.0 \times 10^{-5}$ | 13.1 | 92 | 0.02 | Comparison |
| 16 | 3-28 | $1.0 \times 10^{-5}$ | 13.4 | 92 | 0.02 | Comparison |
| 17 | 3-30 | $1.0 \times 10^{-5}$ | 13.5 | 93 | 0 | Comparison |
| 18 | 3-32 | $5.0 \times 10^{-6}$ | 14.0 | 92 | 0.02 | Comparison |
| 19 | 3-35 | $1.0 \times 10^{-5}$ | 13.7 | 92 | 0.02 | Comparison |
| 20 | 3-36 | $1.0 \times 10^{-5}$ | 12.2 | 90 | 0.03 | Comparison |

It is seen from Table 14 that the hydrazide compounds of formula (3) according to the invention provide light-sensitive materials for photographing which exhibit high gamma characteristics and satisfactory preservability.

EXAMPLE 25

Coated samples were prepared by basically following the formulation described in Example 5 of JP-A-7-43867 and using the hydrazide compound of formula (3) according to the present invention. The coated samples were processed and evaluated in the same manner as in Example 4. As a result, the light-sensitive materials for photographing were proved to exhibit high gamma characteristics and satisfactory preservability.

EXAMPLE 26

The same procedure as in Example 6 was repeated except for changing the hydrazide compound as shown in Table 15 below. The results obtained are shown in Table 15.

TABLE 15

| Run No. | Nucleating Agent Kind | Amount (mol/m$^2$) | $\gamma$ | Preservability Retention of Nucleating Agent | $\Delta S_{1.5}$ | Remark |
|---|---|---|---|---|---|---|
| 1 | Cpd. A | $3.0 \times 10^{-5}$ | 5.6 | 83 | 0.03 | Comparison |
| 2 | Cpd. B | $3.0 \times 10^{-5}$ | 5.4 | 83 | 0.03 | Comparison |
| 3 | Cpd. C | $3.0 \times 10^{-5}$ | 6.2 | 82 | 0.04 | Comparison |
| 4 | Cpd. D | $3.0 \times 10^{-5}$ | 5.4 | 80 | 0.06 | Comparison |
| 5 | Cpd. 3E | $3.0 \times 10^{-5}$ | 11.3 | 71 | 0.10 | Comparison |
| 6 | Cpd. 3F | $3.0 \times 10^{-5}$ | 5.3 | 95 | 0 | Comparison |
| 7 | Cpd. 3G | $3.0 \times 10^{-5}$ | 11.2 | 68 | 0.11 | Comparison |
| 8 | 3-1 | $3.0 \times 10^{-5}$ | 10.6 | 94 | 0 | Invention |
| 9 | 3-2 | $3.0 \times 10^{-5}$ | 11.1 | 93 | 0 | Invention |
| 10 | 3-5 | $3.0 \times 10^{-5}$ | 10.1 | 92 | 0.01 | Invention |
| 11 | 3-9 | $3.0 \times 10^{-5}$ | 10.9 | 94 | 0 | Invention |
| 12 | 3-14 | $3.0 \times 10^{-5}$ | 10.3 | 92 | 0.01 | Invention |

TABLE 15-continued

| | Nucleating Agent | | | Preservability | | |
|---|---|---|---|---|---|---|
| Run No. | Kind | Amount (mol/m$^2$) | γ | Retention of Nucleating Agent | $\Delta S_{1.5}$ | Remark |
| 13 | 3–17 | $3.0 \times 10^{-5}$ | 9.6 | 89 | 0.02 | Invention |
| 14 | 3–22 | $3.0 \times 10^{-5}$ | 11.0 | 94 | 0 | Invention |
| 15 | 3–24 | $3.0 \times 10^{-5}$ | 10.7 | 92 | 0.02 | Invention |
| 16 | 3–28 | $3.0 \times 10^{-5}$ | 10.6 | 92 | 0.01 | Invention |
| 17 | 3–30 | $3.0 \times 10^{-5}$ | 10.5 | 93 | 0 | Invention |
| 18 | 3–32 | $1.5 \times 10^{-5}$ | 10.0 | 92 | 0.02 | Invention |
| 19 | 3–35 | $3.0 \times 10^{-5}$ | 10.7 | 92 | 0.02 | Invention |
| 20 | 3–36 | $3.0 \times 10^{-5}$ | 9.5 | 90 | 0.03 | Invention |

It is seen from Table 15 that the hydrazide compounds of formula (3) according to the invention provide light-sensitive materials for dot-to-dot work to be processed in a lighted room which exhibit high gamma characteristics and satisfactory preservability.

EXAMPLE 27

The light-sensitive materials prepared in Example 11 to 16 were processed in the same manner as in the respective Example except for replacing developer A with developer B or C described in Example 7. As a result, similarly satisfactory results were obtained with developers B and C.

EXAMPLE 28

The same procedure as in Example 8 was repeated, except for changing the hydrazide compound as shown in Table 16 below. The results of evaluation are shown in Table 16.

TABLE 16

| Nucleating Agent | Amount (mmol/mol-Ag) | Dmax | Dmin | Remark |
|---|---|---|---|---|
| none | — | 0.07 | 0.07 | Comparison |
| 3–1 | 0.040 | 1.63 | 0.06 | Invention |
| 3–3 | 0.040 | 1.90 | 0.08 | Invention |
| 3–12 | 0.040 | 1.71 | 0.07 | Invention |
| Cpd. J | 0.4 | 1.24 | 0.07 | Comparison |

It can be seen from Table 16. that the compounds of formula (3) exhibit satisfactory performance in reversal processing even when added in a smaller amount than the comparative compound.

EXAMPLE 29

The same procedure as in Example 9 was repeated, except for changing the hydrazide compound as shown in Table 17 below. The results of evaluation are shown in Table 17.

TABLE 17

| Nucleating Agent | Amount (mmol/mol-Ag) | Dmax | Dmin | Remark |
|---|---|---|---|---|
| none | — | 0.04 | 0.04 | Comparison |
| 3–1 | 0.50 | 1.92 | 0.04 | Invention |
| 3–3 | 0.50 | 1.81 | 0.03 | Invention |
| 3–12 | 0.50 | 2.01 | 0.04 | Invention |

TABLE 17-continued

| Nucleating Agent | Amount (mmol/mol-Ag) | Dmax | Dmin | Remark |
|---|---|---|---|---|
| 3–35 | 0.25 | 1.97 | 0.04 | Invention |
| Cpd. J | 1.0 | 1.54 | 0.04 | Comparison |
| Cpd. K | 1.0 | 1.77 | 0.05 | Comparison |
| Cpd. M | 1.0 | 1.72 | 0.04 | Comparison |

It can be seen from Table 17 that the hydrazide compounds of formula (3) exhibit satisfactory performance in reversal processing even with a developer having a low pH when added in a smaller amount than the comparative compounds.

EXAMPLE 30

The same procedure as in Example 10 was repeated except for changing the hydrazide compound as shown in Table 18 below. The results obtained are shown in the Table.

TABLE 18

| | Nucleating Agent | | | | | |
|---|---|---|---|---|---|---|
| Sample No. | Kind | Layer | Amount (mmol/m$^2$) | Dmax | Dmin | Remarks |
| 101 | ExZK-1 | R | $1.3 \times 10^{-5}$ | 1.75 | 0.30 | Comparison |
| | | G | $1.3 \times 10^{-5}$ | 1.91 | 0.20 | |
| | | B | $0.72 \times 10^{-5}$ | 1.52 | 0.25 | |
| 102 | ExZK-2 | R | $1.5 \times 10^{-5}$ | 1.85 | 0.24 | Comparison |
| | | G | $1.5 \times 10^{-5}$ | 2.01 | 0.22 | |
| | | B | $1.0 \times 10^{-5}$ | 1.75 | 0.24 | |
| 103 | 3-1 | R | $5.0 \times 10^{-6}$ | 2.11 | 0.20 | Invention |
| | | G | $5.0 \times 10^{-6}$ | 2.42 | 0.13 | |
| | | B | $3.0 \times 10^{-6}$ | 2.11 | 0.15 | |
| 104 | 3-12 | R | $5.0 \times 10^{-6}$ | 2.46 | 0.21 | Invention |
| | | G | $5.0 \times 10^{-6}$ | 2.71 | 0.12 | |
| | | B | $2.6 \times 10^{-6}$ | 2.31 | 0.16 | |
| 105 | 3-35 | R | $2.5 \times 10^{-6}$ | 2.04 | 0.20 | Invention |
| | | G | $2.5 \times 10^{-6}$ | 2.21 | 0.11 | |
| | | B | $1.2 \times 10^{-6}$ | 2.00 | 0.12 | |

It is seen from Table 18 that the hydrazide compounds of formula (3), as used in multilayer color direct positive light-sensitive materials, exhibit satisfactory performance in reversal processing at reduced amount.

While the invention has been described in detail and with reference to specific examples thereof, it will be apparent to one skilled in the art that various changes and modifications can be made therein without departing from the spirit and scope thereof.

What is claimed is:

1. A silver halide photographic material comprising at least one hydrazide compound represented by formula (1), (21) or (3):

$$X_1-(R_3)_{m3}-(L_2-R_2)_{m2}-L_1-A_1-NHNH-CO-R_1 \qquad (1)$$

wherein $R_1$ represents an unsubstituted difluoromethyl group or an unsubstituted monofluoromethyl group;

$A_1$ represents a divalent aromatic group;

$X_1$ represents a group accelerating adsorption to silver halide;

$R_2$ and $R_3$ each represents a divalent aliphatic or aromatic group;

$L_1$ and $L_2$ each represents a divalent linking group; and $m_2$ and $m_3$ each represents 0 or 1,

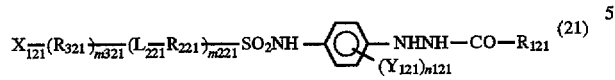

wherein $X_{121}$ represents an alkylthio group, an arylthio group, a heterocyclic thio group, a quaternary ammonium group, a nitrogen-containing heterocyclic group containing a quaternarized nitrogen atom, an alkoxy group containing an ethyleneoxy or propyleneoxy unit, or a saturated heterocyclic group containing a sulfide or disulfide linkage;

$R_{121}$ represents an unsubstituted difluoromethyl group or an unsubstituted monofluoromethyl group;

$R_{221}$ and $R_{321}$ each represents a divalent aliphatic or aromatic group;

$L_{221}$ represents a divalent linking group;

$m_{221}$ and $m_{321}$ each represents 0 or 1;

$Y_{121}$ represents a substituent; and $n_{121}$ represents an integer of 0 to 4;

provided that the hydrazide compound represented by formula (21) is represented by the following formula (22) when $X_{121}$ represents an alkylthio group,

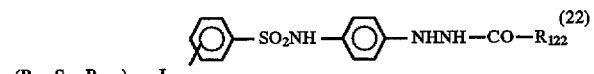

wherein $R_{122}$ represents an unsubstituted difluoromethyl group or an unsubstituted monofluoromethyl group;

$R_{422}$ represents an alkylene group;

$L_{322}$ represents a group linking to the benzene ring selected from the group consisting of an acylamino group, a carbamoyl group, a ureido group, an oxycarbonyl group and a sulfonamido group; when $L_{322}$ represents an acylamino group, oxycarbonyl group or sulfonamido group, $m_{422}$ represents 1; when $L_{322}$ represents a carbamoyl group or a ureido group, $m_{422}$ represents 1 or 2; when $m_{422}$ represents 1, $R_{522}$ represents an unsubstituted alkyl group having 7 or more carbon atoms, a substituted alkyl group having 1 to 18 carbon atoms in total or a cycloalkyl group having 3 or more carbon atoms in total; when $m_{422}$ is 2, $R_{522}$ represents a substituted or unsubstituted alkyl group having 1 to 18 carbon atoms in total or a cycloalkyl group having 3 or more carbon atoms in total;

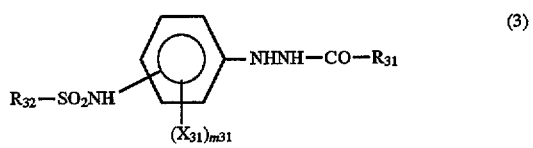

wherein $R_{31}$ represents an unsubstituted difluoromethyl group or an unsubstituted monofluoromethyl group;

$R_{32}$ represents an aliphatic group, an aromatic group or a heterocyclic group, provided that a substituted phenyl group which may be represented by $R_{32}$ does not contain an aralkylamino group as a substituent, and provided that $R_{32}$ does not contain a group accelerating adsorption to silver halide, an alkylthio group, an arylthio group, a heterocyclic thio group, a quaternary ammonium group, a nitrogen-containing heterocyclic group containing a quaternarized nitrogen atom, an alkoxy group containing an ethyleneoxy or propyleneoxy unit, or a saturated heterocyclic group containing a sulfide or disulfide linkage;

$X_{31}$ represents a substituent; and $m_{31}$ represents an integer of 0 to 4.

2. The silver halide photographic material as claimed in claim 1, wherein the hydrazine compounds represented by formula (1) are represented by the following formula (11):

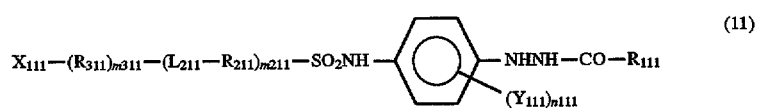

wherein $X_{111}$, $R_{111}$, $R_{211}$, $R_{311}$, $L_{211}$, $m_{211}$, and $m_{311}$ have the same meaning as $X_1$, $R_1$, $R_2$, $R_3$, $L_2$, $m_2$, and $m_3$ of formula (1), respectively;

$Y_{111}$ represents a substituent; and $n_{111}$ represents an integer of 0 to 4.

3. The silver halide photographic material as claimed in claim 1, wherein the hydrazine compound represented by formula (3) is a compound in which $R_{32}$ is a phenyl group having a nondiffusion group as a substituent.

4. The silver halide photographic material as claimed in claim 1, wherein the hydrazine compound is represented by formula (1) and wherein $X_1$ represents a thioamido group, a mercapto group or a 5- or 6-membered nitrogen-containing heterocyclic group.

* * * * *